(12) United States Patent
Zadini et al.

(10) Patent No.: US 6,296,653 B1
(45) Date of Patent: Oct. 2, 2001

(54) CARDIAC RESUSCITATION DEVICE FOR PERCUTANEOUS DIRECT CARDIAC MASSAGE

(76) Inventors: Filiberto P. Zadini, 16814 Rayen St., North Hills, CA (US) 91343; Giorgio C. Zadini, 2237 Hilltop La., Camarillo, CA (US) 93012

( * ) Notice: Subject to any disclaimer, the term of this patent is extended or adjusted under 35 U.S.C. 154(b) by 0 days.

(21) Appl. No.: 09/428,139

(22) Filed: Oct. 26, 1999

Related U.S. Application Data

(63) Continuation of application No. 08/555,985, filed on Nov. 13, 1995, now Pat. No. 5,931,850, which is a continuation-in-part of application No. 08/100,573, filed on Jul. 30, 1993, now abandoned, which is a continuation-in-part of application No. 07/924,301, filed on Aug. 3, 1992, now Pat. No. 5,466,221.

(51) Int. Cl.[7] .................................................. A61M 29/00
(52) U.S. Cl. .................... 606/192; 604/500; 604/509; 604/104
(58) Field of Search ..................... 606/192, 191, 606/194; 604/200, 502, 507, 509, 511, 523, 532, 96.01, 97.01, 98.01, 100.01, 104, 107

(56) References Cited

U.S. PATENT DOCUMENTS

| 471,850 | 3/1892 | Bonis . |
| 1,177,388 | 3/1916 | Crane . |

(List continued on next page.)

FOREIGN PATENT DOCUMENTS

| 256694 | 8/1948 | (CH) . |
| 314482 | 7/1956 | (CH) . |
| 848 234 | 9/1952 | (DE) . |
| 1271895 | 7/1968 | (DE) . |
| 3401522 A1 | 7/1985 | (DE) . |
| 0 791 330A2 | 8/1997 | (EP) . |
| WO 97/21461 | 6/1997 | (WO) . |
| WO 97/34532 | 9/1997 | (WO) . |
| WO 97/37701 | 10/1997 | (WO) . |
| WO 98/04314 | 2/1998 | (WO) . |

OTHER PUBLICATIONS

Anstadt, M.P. et al., "Direct Mechanical Ventricular Actuation for Cardiac Arrest in Humans, A Clinical Feasibility Trial," (1991) *Chest* 100:86–92.

Anstadt, M.P. et al., "Pulsatile Reperfusion After Cardiac Arrest Improves Neurologic Outcome," (1991) *Ann. Surg.*, vol. 214, No. 4, pp. 478–490.

Anstadt, M.P. et al., "Mechanical cardiac actuation achieves hemodynamics similar to cardiopulmonary bypass," (1990) *Surgery*, vol. 108, No. 2, pp. 442–451.

Anstadt, G.L. et al., "Prolonged circulatory support by direct mechanical ventricle assistance," (1966) *Trans. Amer. Soc. Artif. Int. Organs*, vol. XII, pp. 72–79.

(List continued on next page.)

*Primary Examiner*—Manuel Mendez
(74) *Attorney, Agent, or Firm*—Townsend and Townsend and Crew LLP

(57) ABSTRACT

An apparatus and method for cardiac resuscitation wherein the apparatus has an expandable member carried by a rigid stem and placeable inside the chest cavity adjacent to the heart by the tip end of the stem to effect pumping of the heart by applying and releasing pressure to the expandable member via a rigid stem from outside the chest cavity through the chest wall so as to alternately compress and decompress the heart and further includes numerous safety mechanisms to prevent injuries to the intrathoracic organs and mishaps. Compression and decompression may be achieved by moving the expanded expandable member toward the heart and away from it, or by alternatively expanding and contracting said expandable member to effect pumping of the heart.

9 Claims, 35 Drawing Sheets

U.S. PATENT DOCUMENTS

| | | |
|---|---|---|
| 1,242,806 | 10/1917 | Hoein . |
| 2,587,913 | 3/1952 | Smith . |
| 2,612,892 | 10/1952 | Beatman . |
| 2,782,786 | 2/1957 | Krasno . |
| 2,815,523 | 12/1957 | Fink . |
| 2,826,193 | 3/1958 | Vineberg . |
| 2,912,976 | 11/1959 | Grund . |
| 3,204,469 | 9/1965 | Spillers . |
| 3,216,039 | 11/1965 | McNelley, Sr. et al. . |
| 3,371,662 | 3/1968 | Heid et al. . |
| 3,389,703 | 6/1968 | Criswell et al. . |
| 3,455,298 | 7/1969 | Anstadt . |
| 3,496,932 | 2/1970 | Prisk et al. . |
| 3,613,672 | 10/1971 | Schiff . |
| 3,747,594 | 7/1973 | Bishop . |
| 3,753,267 | 8/1973 | Johnson, Sr. . |
| 4,048,990 | 9/1977 | Goetz . |
| 4,192,293 | 3/1980 | Asrican . |
| 4,429,688 | 2/1984 | Duffy . |
| 4,439,185 | 3/1984 | Lundquist . |
| 4,448,190 | 5/1984 | Freeman . |
| 4,508,107 | 4/1985 | Strom et al. . |
| 4,536,893 | 8/1985 | Parravicini . |
| 4,690,134 | 9/1987 | Snyders . |
| 4,731,076 | 3/1988 | Noon et al. . |
| 4,747,396 | 5/1988 | Richardson et al. . |
| 4,753,226 | 6/1988 | Zheng et al. . |
| 4,915,395 | 4/1990 | Chun . |
| 4,934,360 | 6/1990 | Heilbron et al. . |
| 4,940,459 | 7/1990 | Noce . |
| 4,962,758 | 10/1990 | Lasner et al. . |
| 5,084,060 | 1/1992 | Freund et al. . |
| 5,169,381 | 12/1992 | Snyders . |
| 5,224,469 | 7/1993 | Mocny . |
| 5,263,962 | 11/1993 | Johnson et al. . |
| 5,279,281 | 1/1994 | Harvey . |
| 5,484,391 | 1/1996 | Buckman, Jr. et al. . |
| 5,496,345 | 3/1996 | Kieturakis et al. . |
| 5,514,153 | 5/1996 | Bonutti . |
| 5,540,711 | 7/1996 | Kieturakis et al. . |
| 5,571,074 | 11/1996 | Buckman, Jr. et al. . |
| 5,573,517 | 11/1996 | Bonutti et al. . |
| 5,582,580 | 12/1996 | Buckman, Jr. et al. . |
| 5,593,418 | 1/1997 | Mollenauer . |
| 5,601,581 | 2/1997 | Fogarty et al. . |
| 5,601,589 | 2/1997 | Fogarty et al. . |
| 5,601,590 | 2/1997 | Bonutti et al. . |
| 5,607,443 | 3/1997 | Kieturakis et al. . |
| 5,618,287 | 4/1997 | Fogarty et al. . |
| 5,624,381 | 4/1997 | Kieturakis . |
| 5,653,726 | 8/1997 | Kieturakis . |
| 5,667,479 | 9/1997 | Kieturakis . |
| 5,667,520 | 9/1997 | Bonutti . |
| 5,685,826 | 11/1997 | Bonutti . |
| 5,690,668 | 11/1997 | Fogarty et al. . |
| 5,694,951 | 12/1997 | Bonutti . |
| 5,702,416 | 12/1997 | Kieturakis et al. . |
| 5,702,417 | 12/1997 | Hermann . |
| 5,707,390 | 1/1998 | Bonutti . |
| 5,716,325 | 2/1998 | Bonutti . |

OTHER PUBLICATIONS

Bartlett, R.L. et al., "Comparative: Closed–Chest, Open–Chest Manual, and Direct Mechanical Ventricular Assistance," (1984) *Annals of Emergency Medicine*, 13:9, pp. 773–777.

Coogan, P.S. et al., "Direct Mechanical Ventricular Assistance," (1969) *Arch Path*, vol. 87, pp. 423–431.

Goldfarb, D. "Mechanical Circulatory Assistance in the Treatment of Cardiac Failure," (1969) *Progress in Cardiovascular Diseases*, vol. XII, No. 3, pp. 221–242.

Kolff, W.J. et al., "Mechanical Assistance of the Circulation: The Principle and the Methods," (1969) *Progress in Cardiovascular Diseases*, vol. XII, No. 3, pp. 243–270.

Kolobow, T. et al., "Biventrical Cardiac Assistance Energized by Suction Actuated Recoil of a Single Constricting Rubber Ventricle," (1965) *Trans. Amer. Soc. Artif. Organs*, pp. 57–64.

Rassman, W. et al., "An implantable intrathoracic total and partial circulatory support system," (1968) *Journal of Thoracic and Cardiovascular Surgery*, vol. 56, No. 6, pp. 858–868.

Safar, P. et al., "Emergency Cardiopulmonary Bypass for Resuscitation From Prolonged Cardiac Arrest," (1990) *American Journal of Emergency Medicine*, vol. 8, No. 1, pp. 55–67.

Schiff, P. et al., "Synchronization of Direct Mechanical Ventricular Assistance to the Electrocardiogram," (1969) *Trans. Amer. Soc. Artif. Int. Organs*, vol. XV, pp. 424–429.

Skinner, D.B., "Experimental and Clinical Evaluations of Mechanical Ventricular Assistance," (1971) *The American Journal of Cardiology*, vol. 27, pp. 146–154.

Wolcott, M.W. et al., "A Mechanical Heart Massager: A Preliminary Report," (1960) *Surgery*, vol. 18, No. 5, pp. 903–906.

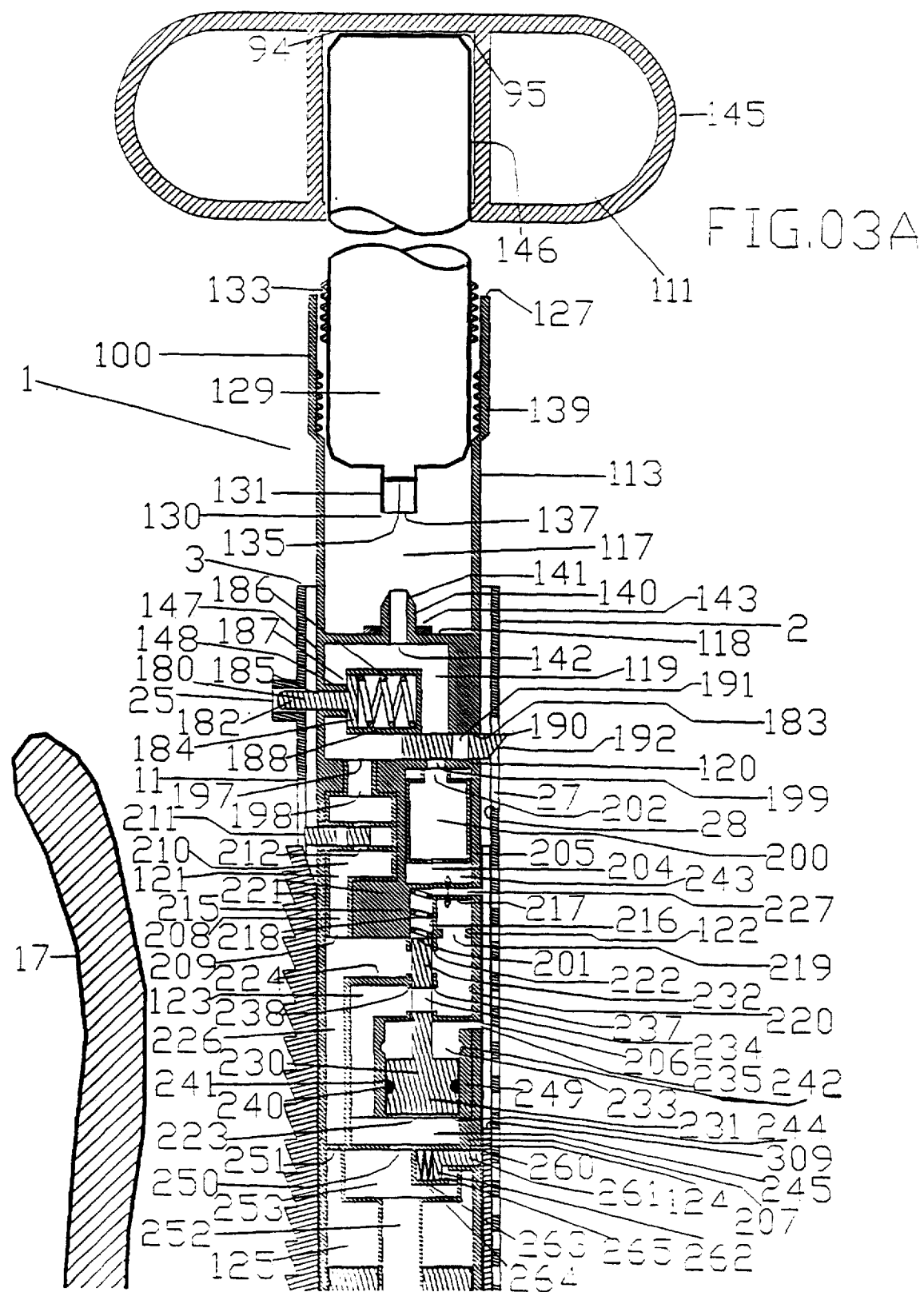

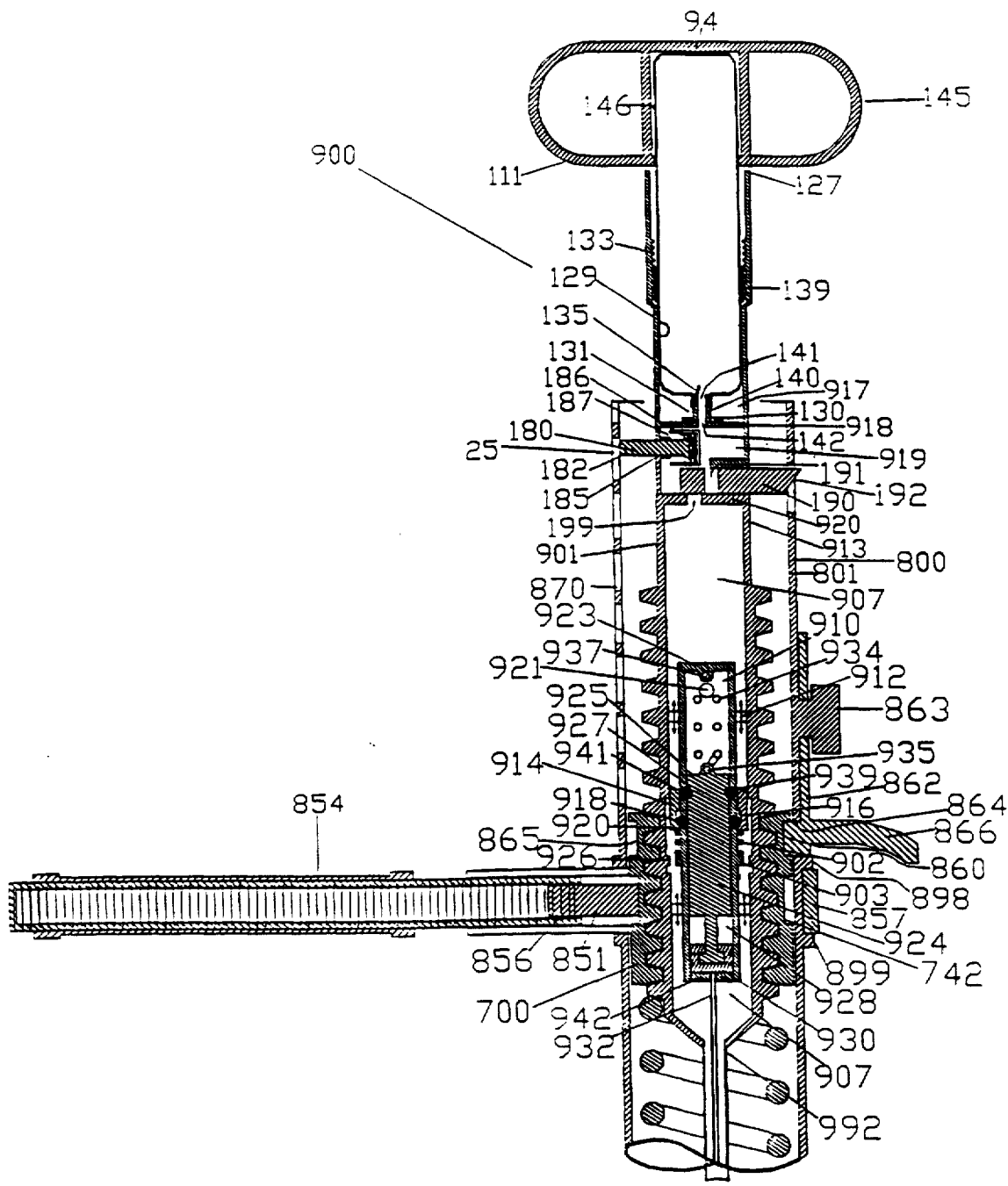
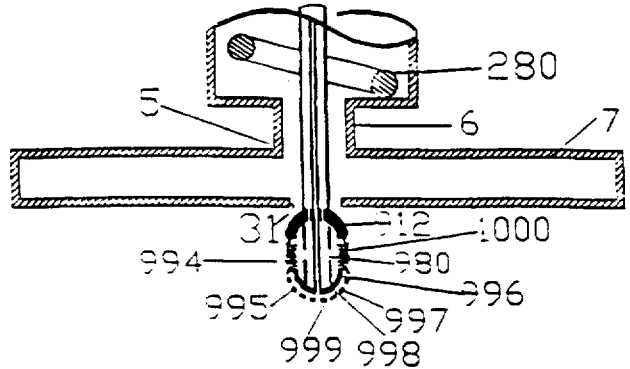
FIG.15

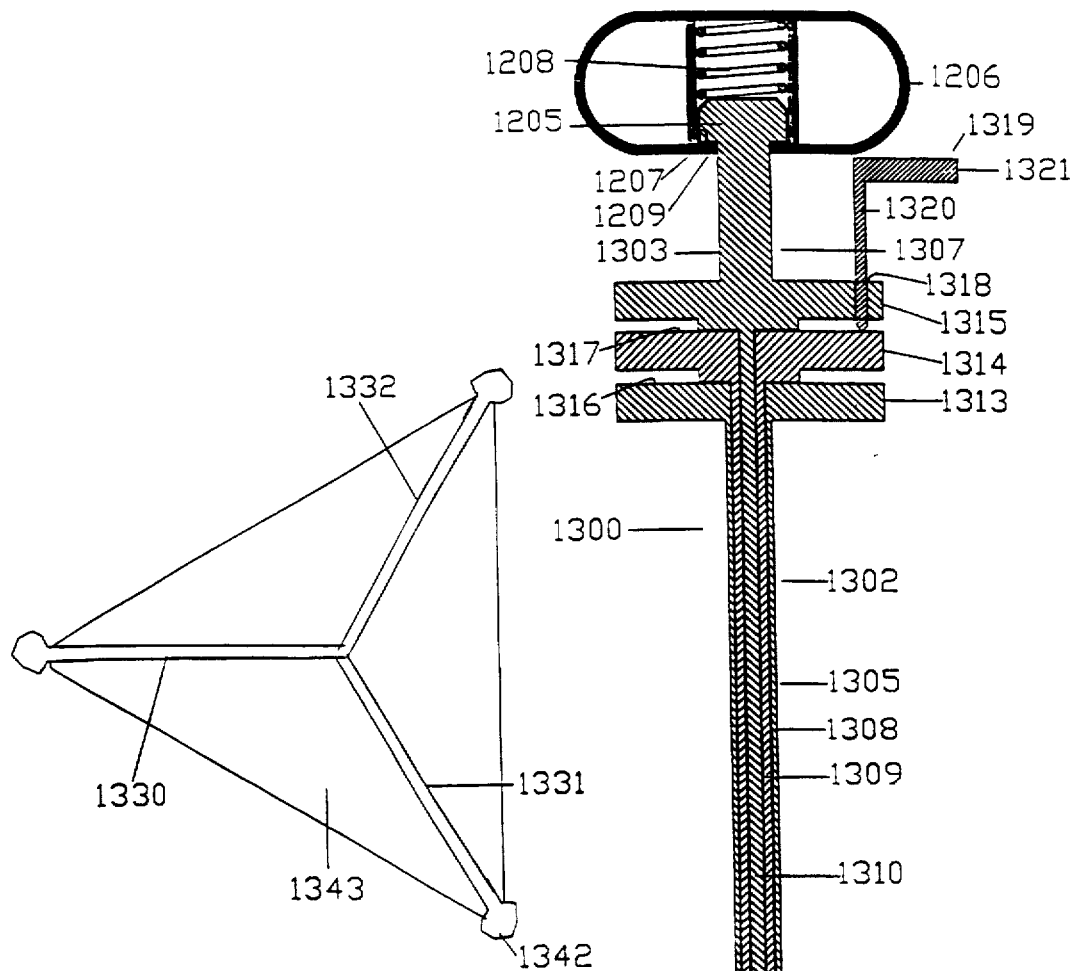
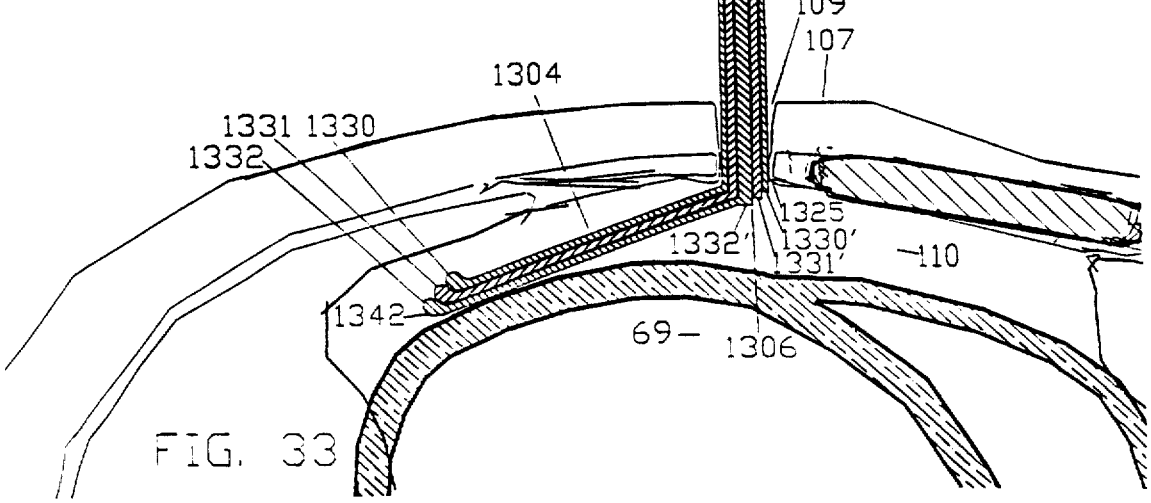
FIG. 34
FIG. 33

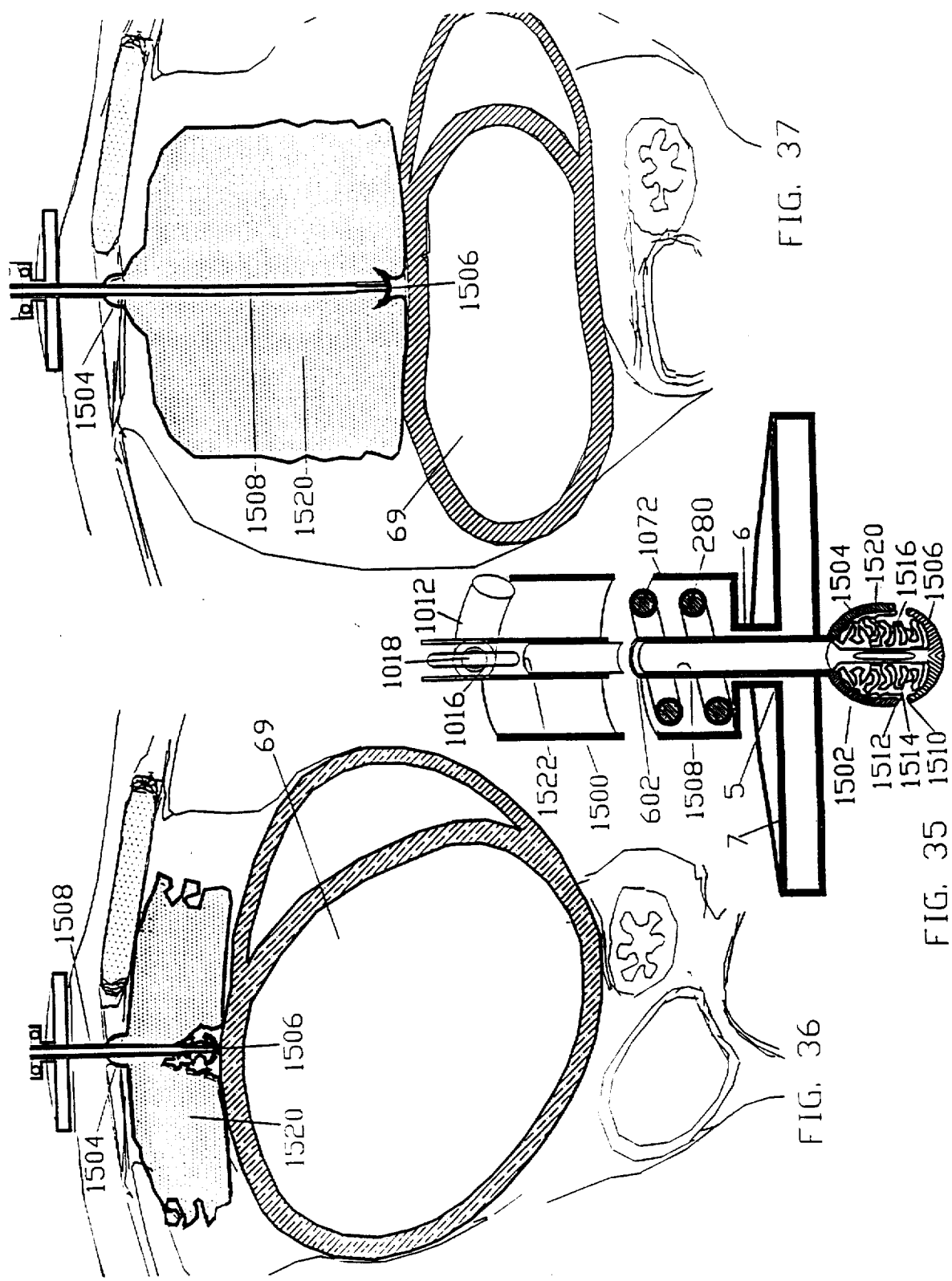

CARDIAC RESUSCITATION DEVICE FOR PERCUTANEOUS DIRECT CARDIAC MASSAGE

CROSS-REFERENCES TO RELATED APPLICATIONS

This application is a continuation of application Ser. No. 08/555,985, filed Nov. 13, 1995, now U.S. Pat. No. 5,931,850 which is a continuation-in-part of patent application Ser. No. 08/100,573, filed on Jul. 30, 1993, now abandoned, which is a continuation-in-part of application Ser. No. 07/924,301 filed on Aug. 3, 1992, now U.S. Pat. No. 5,466,221. The subject mater of this application may be related to the subject matter of U.S. application Ser. No. 09/287,231 filed on Apr. 6, 1999, and now abandoned. The full disclosures of each of these applications are incorporated herein by reference.

BACKGROUND OF THE INVENTION

1. Field of the Invention

This invention relates to methods and apparatus for cardiopulmonary resuscitation and is particularly directed to improved methods and apparatus for performing direct heart massage.

2. Description of the Background Art

In order to resuscitate a patient victim of a cardiac arrest, it is necessary to provide an adequate artificial circulation of oxygenated blood to the vital organs by reestablishing the pumping function of the heart at values as close as possible to the physiological prearrest condition. Such a cardiac pumping function must be instituted at the earliest possible stage. It is documented that a cardiac arrest results in irreversible brain death if a sufficient blood flow is not reestablished within a critical period of time from the moment of the cardiac arrest. Such a period of time is measured ranging between four and six minutes.

In order to reestablish the pumping function of the heart, two methods of cardiopulmonary resuscitation have been used heretofore: external or closed cardiac massage, and internal or open cardiac massage. Closed cardiac massage consists of applying pressure on the anterior chest wall and alternately releasing such pressure. In the vast majority of cases, closed chest compressions produce a severe low flow state, Raymond E. Jackson: *Basic Cardiopulmioniary Resuscitation; Emergency Medicine*, American College of Emergency Physicians. Open chest cardiopulmonary, resuscitation improves hemodynamics, resuscitation and the chance of surviving cardiac arrest.

Cerebral blood flow achieved with open chest techniques has been shown to be near normal physiological values. There are several case reports of patients who have been resuscitated with direct cardiac massage when attempts with closed chest cardiopulmonary resuscitation have been unsuccessful, *Advanced Cardiac Life Support Textbook*, American Heart Association, page 42. However, few physicians today are skilled in the technique of direct cardiac massage. Since most cardiac arrests occur outside of a hospital and since most patients cannot be brought to a facility where a thoracotomy and direct cardiac massage can be performed in less that 15 minutes of total arrest time, the applicability of direct cardiac massage has been limited ACLS textbook, page 42. In addition to that, this technique is often characterized by many physicians as a rather grossly traumatic procedure, often seen as a desperate terminal attempt to resuscitate an arrested heart.

The aforementioned drawbacks of the two prior art techniques of heart massage have been recognized by Prisk and Johnson, who proposed a new method and apparatus for which they obtained a patent, U.S. Pat. No. 3,496,932, issued Feb. 24, 1970. The method and apparatus described by Prisk and Johnson includes an inflatable bladder, insertable through the subxyphoideal region into a space between the sternum and the heart via a trocar-cannula assembly. In order to accommodate the inflatable bladder and its stem, the sharp three-sided tip of the trocar must have a comparably large diameter, as illustrated in FIG. 4 of the Prisk and Johnson patent. However, the larger the sharp three-sided trocar tip, the more likely are injuries to the heart, coronaries or surrounding organs. In addition to the risk inherent in the size of the sharp tip of the trocar, the blind advancement of a trocar with a sharp tip in the thoracic cavity has been proposed by Prisk and Johnson. Such blind advancement carries extremely high risk of puncturing and/or lacerating the heart, coronary vessels or the surrounding structures, with devastating consequences. Prisk and Johnson's proposed position of blindly inserting the trocar between the sternum and the pericardial sac is, indeed, an extremely risky procedure; this space being very narrow, while it is virtually impossible to insert the trocar into the other designated position, i.e., within the pericardial sac, this space being only virtual, since the visceral and parietal pericardium are in contact, separated only by a thin film of pericardial fluid. Furthermore, the device proposed by Prisk and Johnson lacks any mechanism for locating the position of the sharp tip of the trocar and lacks any safety mechanisms to prevent or avoid injuries, such as puncturing of the heart or coronary vessels. Moreover, an inflatable bladder with a laterally flexible stem, as proposed by Prisk and Johnson, lacks the required stability for maintaining its central position to effectively compress the heart. Also, the proposed inflatable-deflatable bladder has no guidance, thus lacking the ability to properly impress direction of the compressions toward the vertebral column, allowing the heart to be displaced during the phase of compression laterally to the column, and not maintaining the heart in position between the vertebral column and the sternum, as required for effective pumping and resulting in ineffective compression of the heart. Given the individual variability in the size and depth of the thoracic cage, the device of Prisk and Johnson is inadequate in that it has no means to adapt to the various depths of the thoracic cavity and ignores the variability in the distance between the sternum and the vertebral column. Finally, the method of insertion of the Prisk and Johnson bladder is a multistep manual procedure, which is necessarily time-consuming and conflicts with the need for a rapid institution of cardiopulmonary resuscitation.

Buckman and Badellino in their PCT Application No. PCT/US 93/06886 with international filing date Jul. 20, 1993, describe a plunger-like apparatus for intrathoracic direct substemal heart massage comprising a heart contacting member having a surface which is at least partially concave for contacting the heart and handle means attached to the heart for manually manipulating the apparatus.

With regard to the critical issue of entering the chest cavity to use their plunger like device, in a way that prevents injuries to the intrathoracic organs, and is more practical than a traditional thoracotomy. Buckman and Badellino disclose a "small thoracotomy" which they describe as a full thickness incision by sharp dissection, from side to side of the chest wall, of a width ranging from about three and a half inch to about one inch.

Although a thoracotomy of such a reduced size is indeed an improvement over a traditional thoracotomy, because it is more expedite, still it is not the solution to the problem of entering the chest cavity safely to introduce means for heart compression on a patient with cardiac arrest. Buckman's reduced thoracotomy still cannot prevent the occurrence of pneumothorax, i.e., the collapsing of the lungs. As a matter of fact, with the incision size required by the sizes of the devices as described by Buckman and with the incision sizes actually disclosed by Buckman, pneumothorax is an unavoidable occurrence associated with Buckman's devices. Pneumothorax is obviously a non-acceptable complication in a patient in cardiac arrest who has a critical need for oxygen. A pneumothorax requires the placement of a chest tube to re-expand the lungs, which is another invasive surgical procedure, and adds problems to problems and morbidity to morbidity, and which cannot be practically performed for instance on the field at the site of a cardiac arrest if the cardiac arrest, as most of them do, has occurred outside a hospital setting.

In reality, in prior art, such as in Prisk's invention, an incision of one inch or so is required, and possibly the introduction of the inflatable-deflatable balloon by Prisk may even require a smaller incision than the incisions disclosed by Buckman and Badellino. With that regard, the device proposed by Buckman and Badellino hardly seems to offer a real advantage or be an improvement over Prisk. Yet quite an emphasis is placed in the minimized dimension of the surgical incision required to pass Buckman's device into the chest cavity, to the extent that the procedure of chest massage is named by Buckman and Badellino as minimally invasive.

On the contrary, the drawbacks of even a small thoracotomy such as the one proposed by Buckman, which still causes pneumothorax, are completely overcome with this invention, which resolves the problem of introducing a heart massaging member into the chest cavity without causing pneumothorax. The width of passage through the chest wall needed to insert the heart massaging members disclosed in parent application Ser. No. 07/921,301 by Zadini et al. in application Ser. No. 08/100,573 by Zadini et al. and in this present application can be much smaller than the sizes reported by Buckman and Badellino. Due to the very small width of the passage through the chest wall the devices disclosed in parent application Ser. No. 07/921,301 by Zadini et al., application Ser. No. 08/100,573 by Zadini et al., and in this present application can take advantage of a location for entry into the chest cavity in the left parasternal region in a skin area corresponding to the intrathoracic anatomical area designated "sine pleura." The choice of the area "sine pleura" prevents precisely the insurgence of pneumothorax, i.e., collapsing of the lung, which inevitably occurs every time the pleural cavity is inadvertently entered. With regard to the occurrence of pneumothorax, due to the fact that the area "sine pleura" is a substantially restrictive area, the choice of such area is only meaningful if the opening passage through the chest wall is significantly small, such as it can be achieved with all the embodiments described in parent application Ser. No. 07/921,301 by Zadini et al., application Ser. No. 08/100,573 by Zadini et al., and in this present Application. Being the width of the area "sine pleura" such a small area, only the Zadini's devices can enter the chest safely without causing collapsing of the lungs.

With regard to another critical issue, i.e., the problem of avoiding injuries to other intrathoracic organs besides the pleural cavity and the lungs, when entering the chest cavity, such as the heart, which is laying just beneath the anterior chest wall, Buckman's disclosed method of entry into the chest cavity is of an entry by sharp dissection with sharp surgical instruments. No different from Prisk's entry by sharp dissection with a trocar.

In particular, Prisk, page 2, lines 68–69, discloses "a trocar and cannula assembly" which "are used as tools to expedite the placement of the bladder within the chest." Prisk's bladder is equivalent to Buckman's plunger-like heart massaging member. Such tools for the placement of the bladder within the chest are precisely the equivalent of the Buckman's "sharp surgical instrument." Buckman's device, no differently from and no better than Prisk's device, is inserted into the chest after a passage is opened through the chest wall and entry by sharp dissection into the chest cavity is carried out by the sharp tip or edge of a surgical instrument such as a surgical blade, as clearly and unequivocally is repeatedly disclosed by Buckman in the specification and also in his claims. For instance, page 1, line 8, "a heart massager which is introduced through a relatively small surgical incision made in the chest wall;" page 8, lines 30, 31, and page 9, lines 1 and 2, "The instant invention is related to massagers and a particular method for their usage that allows each massager to be inserted through a small surgical opening made in the chest wall, so as to allow to directly contact the antero-lateral surface of the human heart;" page 9, lines 30, 31, and page 10, lines 1 through 4, "In its operation and in general manner, the massager is inserted into the left chest via small surgical incision. The massager has a heart contacting member that is subcutaneously inserted through the incision and into the interior of the chest so that the now substernal massager may be placed on the anterior and lateral surface of the ventricular chambers of the heart." Page 6, lines 19 through 20, "surgically separating the intercostal space inserting the heart massages through the intercostal space, etc." Page 27, lines "after a surgical incision is made a sharp surgical instrument is used to provide sharp dissection preferably in the fourth intercostal space, thereby allowing for the entrance of the finger of the operator which is used to locate, by finger palpation, the apex region of the heart."

Therefore the first entry into the chest cavity, in front of the underlying heart, is of a sharp tip or of a razor-like blade of a surgical knife, and is no different from the sharp, razor-like tip of the Prisk trocar. The chances of injuring the underlying heart, which is in contact with the anterior chest wall are still there either that the razor-like blade of a surgical knife is used or a sharply tipped trocar is used.

Notwithstanding the fact that Buckman's entry into the chest is by sharp dissection, no less and no better than Prisk's, Buckman and Badellino at page 3, lines 23–24 of their application seem to favorably compare their method of inserting the device into the chest cavity over Prisk's method by stating: "it is desired that the heart massager not only be devoid of a pointed tip, etc." There seems to be suggested that, unlikely Buckman's heart massaging member which is devoid of a pointed tip, Prisk's heart massaging member does have pointed tips, etc. However, Prisk's heart massaging member, being an inflatable-deflatable bladder has no pointed tips nor sharp edges at all.

In particular Prisk's balloon is "devoid of any sharp tip that may unnecessarily and inadvertently damage body elements" no more and no less than Buckman's and Badellino's heart massaging member.

Buckman and Badellino do not disclose an entry by blunt dissection into the chest cavity but only of inserting a blunt heart massaging member, or more precisely, of inserting a heart contacting member devoid of pointed tips or sharp edges, through a passage already opened through the chest wall by sharp means.

However the absence of any pointed tips or share edges in heart massaging members is no novelty. In fact other heart contacting members for cardiac massage as well, such as all the well-known Direct Mechanical Ventricular Assisting Devices described by Anstadt, and many others, are indeed devoid of any sharp tips or sharp edges and are inserted into the chest cavity devoid of any sharp tips and sharp edges after a thoracotomy, i.e., after a full thickness incision of the chest wall carried out by sharp instruments, which is precisely the method used also by Buckian and Badellino, G. L. Anstadt et al., *Trans. Amzer. Soc. Artif Int. Organs*, Vol. XII. 1966; Mark P. Anstadt et al., *Chest*, 1991 Vol. 100; Mark W. Wolcott et al., *Surgery*, 1960 Vol. 48 No. 5; Theodor Kolobow et al., *Trans. Amer. Soc. Artif. Int. Organs*, Vol. XI. 1965; W. Rassman et al., *Journal of Thoracic and Cardiovascular Surgery*, 1968. Vol. 56. No. 6; David Goldfarb, *Prog. Cardiovase. Dis.*, 1969, Vol. 12. No. 3; W. J. Kola, *Progress in Cardiovascular Diseases*, 1969, Vol. XII. No. 3; Peter Schiffet al., *Trans. Amer. Soc. Artif Int. Organs*, Vol. XV, 1969; W. Rassman et al., and Peter Schiffet al., R. Bartlett et al., *Ann. Emerg. Med.*, 13 Part 2 1984; M. Anstadt et al., *Resuscitation*, 21, 1991; P. Safar et al., *Am. J Emerg. Med.* 8, 1990. As far as Prisk is concerned, Prisk teaches precisely to introduce into the chest cavity, through a passage already opened by sharp means, such as his trocar is, his heart massaging member which includes a flexible tube with a closed round distal end and a deflated bladder around the tube. Prisk therefore teaches to enter the chest cavity by the means of sharp dissection then to introduce a heart massaging member which is devoid of any sharp tips or sharp edges. That is precisely the method disclosed by Buckman.

With regard to the further advancement of the heart contacting member within the chest cavity into the substernal region between sternum and heart, after entry into the chest cavity is accomplished with sharp means, it is quite obvious that no sharp means is needed after a passage has been opened through a wall delimiting the chest cavity. No sharp means is needed to advance further into the chest cavity, because the chest cavity where the heart massaging member has to be placed, i.e., the substernal space, is devoid of any structure that needs to be cut through. Therefore, not having to cut through anything, it is obvious that a heart massaging member be devoid of any pointed tips or sharp edges in its transit within the chest cavity. Furthermore the heart massaging member does not have to travel within the chest cavity because the heart is just there, in contact with the internal surface of the thoracic cavity.

Therefore, besides the fact that inserting a heart contacting member being "devoid of sharp tip that may unnecessarily and inadvertently damage body elements," as disclosed by Buckman is not at all, as it will be shown, the problem that needs to be resolved, the introduction into the chest cavity of a heart contacting member which is "devoid of share tip that may unnecessarily and inadvertedly damage body elements" is not novel over Prisk's invention itself and over others' prior art such as the Direct Mechanical Ventricular Actuation Devices of Anstadt and others.

No matter how blunt or how well devoid of sharp tips and edges is the heart massaging member inserted for the purpose of direct cardiac compression, it is precisely the problem of first entry, i.e., of opening the way to access the chest cavity by means of a safe method, which constitutes the main unresolved problem by the prior art, and which Buckman and Badellino fail to resolve. In Buckman and Badellino it is the cutting blade which cuts the deepest layer of the chest wall, that surfaces and makes first its access into the chest cavity. No matter how small can the penetration be into the chest cavity of such a sharp blade or tip, and how carefully can be carried out by the operator, still the entry into a chest cavity in Buckman and Badellino is not an entry by blunt dissection. Indeed the heart massager of Buckman and Badellino is and can only and solely be inserted after a full thickness incision is made through the chest wall including the last layer of tissue lining the chest cavity.

Buckman and Badellino do not disclose in their application any means for blunt dissection, nor entry by blunt dissection. In fact they call for "sharp dissection" provided by a "sharp surgical instrument" after a first surgical incision of the skin is made. Nowhere in their specification is disclosed entry into the chest cavity either by a blunt instrument opening its way into the chest cavity or by a digital blunt dissection. Entrance of the finger of the operator is allowed only after a sharp dissection of the chest wall by a sharp surgical instrument is carried out, and is used for the purpose of locating the apex of the heart.

The main issue of a safe entry is not to make a skin incision to pass the superficial layer represented by the skin and or the subcutaneous tissue, but to avoid a sharp surgical dissection of the chest wall, because the sharp dissection of the chest wall may inadvertedly lead to cutting injuries of intrathoracic organs. Particularly, what has to be avoided is a sharp dissection which separates the deepest final layer of chest wall so as to avoid accessing the chest cavity and entering with a sharp surgical instrument into the chest cavity.

All the embodiments disclosed in Buckman and Badellino preclude the possibility that their devices are advanced and/or entered into the chest cavity by blunt dissection through the chest wall because they are too wide to allow blunt dissection. More specifically, such dimensions are just less than about three inches for the device of FIGS. 1–8, page 12, lines 25–26, and just less than about one inch for the device of FIGS. 9–11, page 12, line 30. In fact, at page 20, lines 10–11, it is acknowledged that this umbrella-like embodiment is inserted through the chest wall by a surgical incision of less than about one inch.

The key issue is not so much to insert into the chest cavity a heart massager devoid of any sharp tips, which is not novel over Prisk, but is to introduce a massager of said characteristics via a safely made entry into the chest cavity via blunt means, not by potentially highly risky means such as a pointed tip or a razor-like surgical blade. In view of the obviously critical status of a patient in a cardiac arrest and the need for performing urgently and safely, Buckman's device does not represent any advantage over Prisk's device. Buckman's device is only an alternative way of pumping the heart. The claimed advantage by Buckman of performing a minimally invasive by a small surgical incision is already present in Prisk and therefore not novel over Prisk.

If direct cardiac massage can be of any practical utility and be performed by paramedics in the field, at the site where cardiac arrests occur, the specific issue of entry into the chest cavity safely and expeditiously is the main issue to be resolved, and this problem is indeed resolved with this invention.

By disclosing means and methods of entering the chest cavity by blunt dissection, this invention resolves the key problem of implementing direct cardiac massage without causing pneumothorax, or other injuries to the intrathoracic organs including the heart.

Thus, none of the prior art methods and apparatus for cardiac pulmonary resuscitation have been entirely satisfactory. A device having features for safe entry into the chest such as a blunt entry into the chest for the purpose of direct cardiac compression and a method of inserting a heart massager into the chest after a safe entry such as a blunt entry into the chest has never been described in any prior art and is subject matter of this invention.

SUMMARY OF THE INVENTION

The disadvantages of the device of Prisk and Johnson, as well as those of closed and open cardiac massage, are overcome with the present invention and an improved method and apparatus for performing cardiopulmonary resuscitation is provided which permits direct cardiac massage without the risks inherent in massive opening of the thoracic cavity, as required in performing a thoracotomy.

It is a general object of our invention to provide a method and apparatus for cardiac massage which combines the hemodynamic effectiveness of direct heart massage with the rapidity of institution of closed heart massage, thus satisfying the two fundamental conditions required to restitute a human being to life and intact mental functions. Special attention was paid to the construction of a device which offers a satisfactory degree of safety in every phase of its operation. A safe device positively effects its effectiveness and its rapidity of application and, therefore, its usefulness.

More specifically, it is a main object of this invention to provide a heart assisting device which is hemodynamically effective in providing coronary arteries, cerebral arteries and systemic circulation with sufficient blood flow. In order to achieve hemodynamic effectiveness, the method of the present invention calls for insertion through the chest wall, in a designated area in front of the heart, of an expandable member such as an inflatable balloon via a blunt stem. The expandable member, fixed to the intrathoracic end of the blunt stem, is inserted via a rigid stem with a blunt tip through the thickness of the chest wall into the chest cavity adjacent to the heart.

In a first type of embodiments, the expandable member is then expanded, and while it is maintained expanded, a mechanical force is then periodically applied to the extrathoracic end of the stem, causing the expandable member to alternately compress the heart against the thoracic spine and releasing such compression to effect pumping of the heart and generate artificial circulation.

In a second type of embodiments, the expandable member is alternatively inflated and deflated to alternatively compress and decompress the heart against the thoracic spine, to generate artificial circulation.

The stem also serves the purpose of guiding the direction of the expandable member as it moves in the first type of embodiments and as it expands and contracts in the second type of embodiments. We are convinced that the device of the present invention grants hemodynamic effectiveness because the direction of compression is guided and the depth of compression and rate of pumping are adjustable.

It is also an object of the present invention to make the installation of a heart assisting device inside the chest cavity an extremely rapid operation. To accomplish such rapid installation, the device is constructed in such a way that its implementation does not require specialized medical knowledge and, consequently, the device of the present invention may be applied by semi-skilled persons, such as paramedic personnel and the like. This will ultimately effect its rapidity of installation and, hence, its usefulness. Moreover, the device of the present invention can safely be applied not only in a hospital by physicians but also in the field, at the site of the cardiac arrest, out of the hospital setting. This feature of rapid and easy installation is achieved by applying the device to an easily accessible and easily identifiable designated area either on the anterior chest wall or on the subxyphoideal region, by the use of a small gauge stem and by the automation of most of the operations of the device, except those controlling the depth and rate of compression, which are preferably left to the discretion of the operator of the device to permit such variations as are desirable to obtain optimal blood flow.

The device performs the cardiopulmonary resuscitation through a small hole in the chest wall, i.e., a thoracostomy, not through the highly traumatic thoracotomy. Furthermore, no pneumothorax is caused by the device and no chest tube placement is required, thus avoiding the high morbidity of both thoracotomy and chest tube placement.

An additional object of the present invention is to construct a device which is as safe as possible in every phase of its operation. Such safety is achieved by a number of features, such as:

1) Use of a disposable sterile unit as that part of the device which will enter the chest cavity to prevent transmission of infections.
2) Use of a bluntly tipped stem to prevent accidental punctures.
3) Use of an inserting mechanism for the inflatable expandable member which grants controlled insertion of the tip of the stem into the chest cavity through the chest wall.
4) Use of an inserting mechanism for the inflatable expandable member which grants control and preservation of the angle of insertion of the stem so that the inflatable expandable member is properly directed in front of the heart to ensure that compression of the heart is directed against the thoracic spine.
5) Use of a feature which grants automatic arrest of the stem advancement into the chest wall, as soon as the tip of the stem has entered the chest cavity, to prevent possible damage to the heart during the insertion of the stem.
6) Use of an automatic and rapid sequence of preparatory steps leading to the inflation of the expandable member in front of the heart.

In general the automation of the preparatory steps should be regarded as a features provided for the purpose of safety, besides rapidity of implementation, because such automation tends to eliminate the possibility of afflicting the operation with human errors, a calamitous inconvenience, but the most likely to occur in a highly rushed situation, such as a cardiac resuscitation attempt.

It is also an object of the present invention to provide an alternative method of safe insertion of an expandable member within the chest cavity, an automatically intervening alternative, in case of malfunctioning of part of the device, arranging for arrest of the operations, easy and rapid extraction of the defective device, and untroubled reinsertion of a replacement device.

These and other objects and features of the present invention will be apparent from the following detailed description, taken with reference to the figures of the accompanying drawings.

BRIEF DESCRIPTION OF THE DRAWINGS

FIG. 15 is a vertical section of a further alternative form of the cardiac pump.

FIG. 33 is a cross-sectional view of an alternative form of the device of FIG. 1 shown after stem tip penetration of the chest cavity.

FIG. 34 is a detail of FIG. 33, precisely of the fully expanded expanding member viewed from below.

FIG. 35 is a cross-sectional view of a detail of an alternative form of the device of FIG. 24.

FIG. 36 is a cross-sectional view of a detail of FIG. 35 showing the device at an early stage of operation.

FIG. 37 is a cross-sectional view of a detail of FIG. 35 showing the device at a subsequent early stage of operation.

DESCRIPTION OF THE SPECIFIC EMBODIMENTS

All the embodiments encompassed in the following specifications share the common features of placing an expandable member inside the chest cavity through a small opening, a small thoracostomy, "not a thoracotomy," in the chest wall in a position adjacent to the heart. Such a placement is carried out in a safe, controlled, largely automatized and expedite fashion by a bluntly tipped member of the device, with minimum invasiveness, and virtually with no possibility of injury to intrathoracic organs and without causing pneumothorax and without requiring chest tubes which are unavoidable in any thoracotomy of whichever size. These features are absolutely critical to the implementation of a device that has to perform not only in the controlled environment of emergency departments and operated by physicians, but also and especially on the field where the cardiac arrest occurs, outside the hospital, where this device can be operated by paramedics and the like.

Restating that all the embodiments share the common denominator of features described above, two distinct types of embodiments have been described on the basis of mechanism of pumping the heart. In one type, type A, the pumping of the heart is accomplished by positioning said expandable member adjacent to the heart, expanding said expandable member, then by displacing said member forward and backward to compress and decompress the heart against the vertebral column by alternatively applying and releasing pressure on a rigid stem connected to said expandable member.

In the other type, type B, of embodiments, the pumping of the heart is accomplished by positioning said expandable member adjacent to the heart, then inflating and deflating said expandable member to compress and decompress the heart.

All the embodiments can be inserted into the chest cavity via means of blunt dissection separately constructed from the actual heart compressing device, although it is preferable to incorporate the means for blunt dissection and the means for performing the heart massage. The blunt dissection can also be accomplished by the method of digital dissection by the operator after a slight skin incision.

TYPE A EMBODIMENTS

Embodiment I

Figure 1:
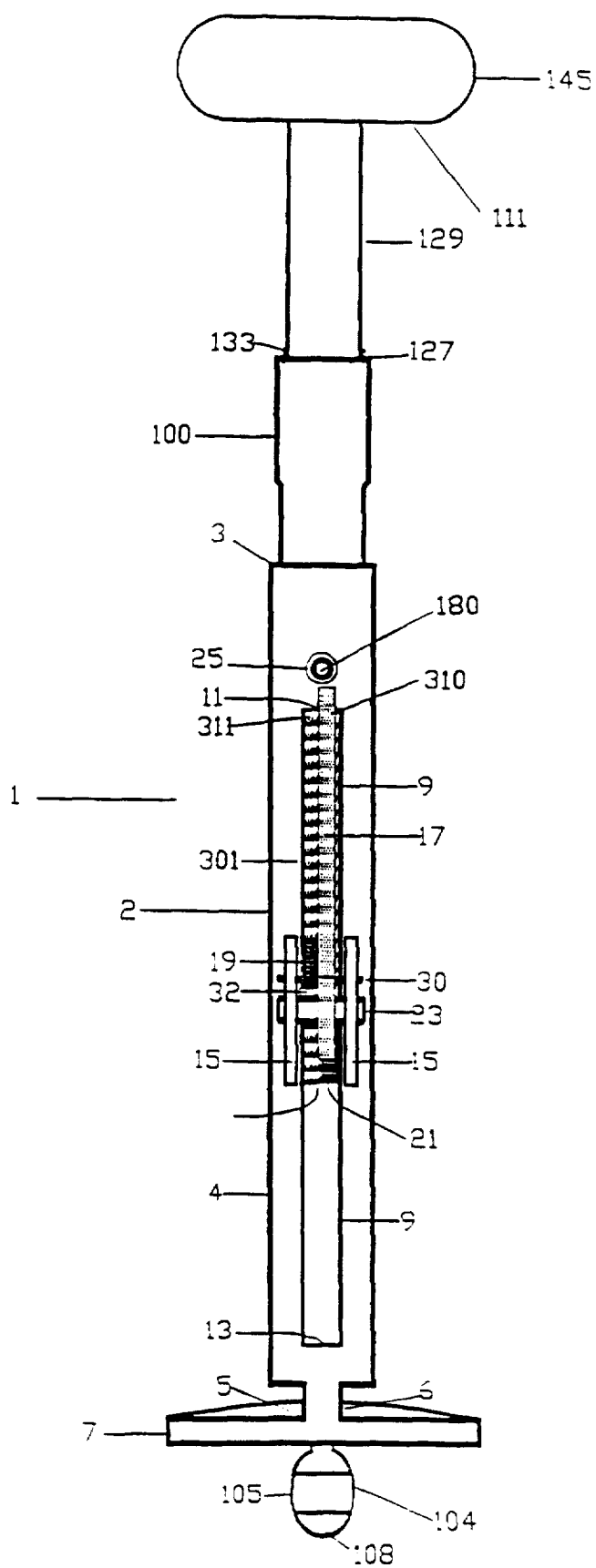
FIG. 1 is a front view of a cardiac pump embodying the present invention.
Figure 2:
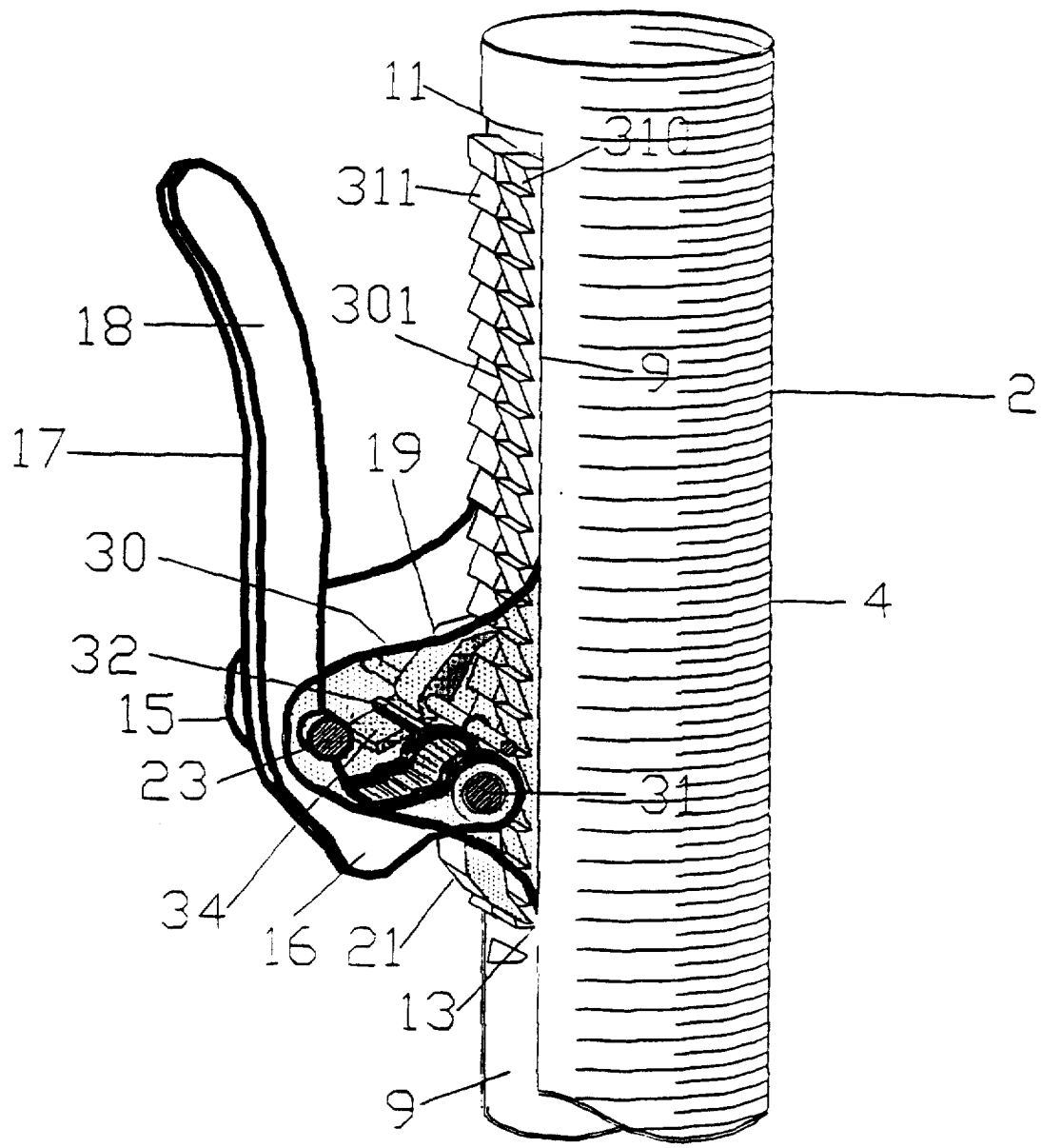
FIG. 2 is tridimensional view of the lever-double rack mechanism of advancement, shown in front view in FIG. 1.
Figure 3B:
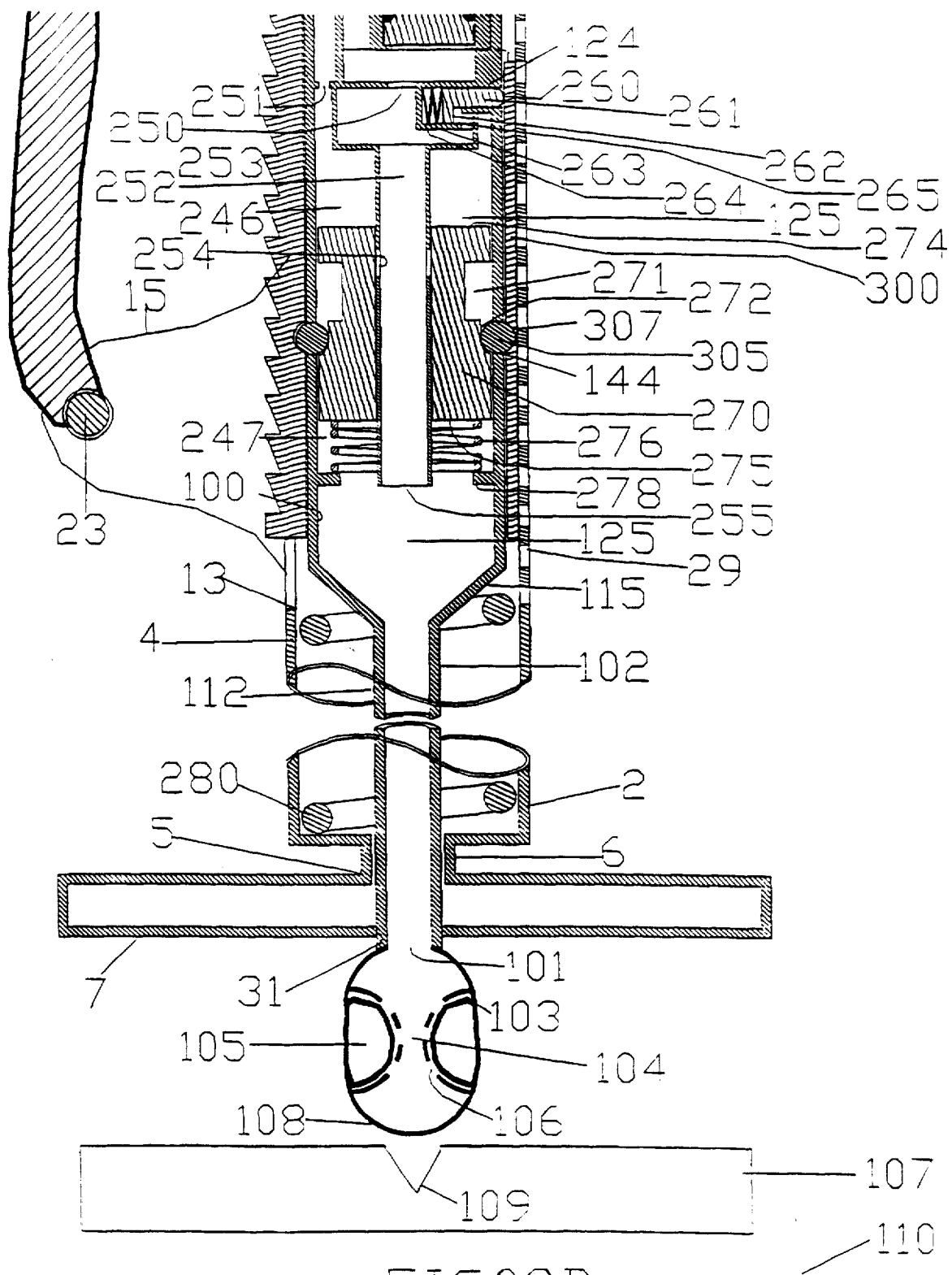
FIG. 3 is a vertical section through the cardiac pump of FIG. 1, showing the cardiac pump is its normal rest position.

In that form of the present invention chosen for purposes of illustration in FIGS. 1–10, a percutaneous cardiac pump, indicated generally at 1, is shown with the actuating mechanism shown in the normal rest position. As best seen in FIG. 3, the cardiac pump 1 is composed of three main components, each of generally cylindrical shape and essentially coaxially mounted: an outer, generally cylindrical, component or support case, indicated generally at 2; an inner, generally cylindrical, component or stem member, or main unit, or stem unit, indicated generally at 100; and an intermediate member, also of generally cylindrical shape, indicated generally at 300, interposed between the stem member 100 and the support case 2.

The support case 2 is hollow and is of generally tubular, cylindrical shape having an open proximal end 3, a body 4 and a distal end 5, including a narrow neck 6, and a flat, circular base 7. The base 7 is preferably formed of transparent material to enable the operator to better visualize the actual position of the pump 1 on the anterior chest of the patient. Also, base 7 is formed with a central opening 31 to allow passage therethrough of stem 102 of the stem member 100, as seen in FIGS. 1 and 3 and more fully described below. The body 4 of the support case 2 has a longitudinal slit 9 extending from its proximal end 11 to a distal end 13, as best seen in FIG. 1 and FIG. 2.

As best seen in FIG. 2, two parallel ears 15 are attached to the body 4 of the support case 2 and protrude outwardly adjacent each side of the slit 9. Ear 15, located on the right side in FIG. 2, is drawn transparent for the purpose of showing the parts located between the ears. Lever 17, with dogs 19 and 21, is interposed between the ears 15 and is pivotally secured to the ears 15 by suitable means, such as pin 23, to form a fulcrum for the lever 17. A double rack 301 is mounted on the intermediate member 300 and projects through the slit 9 for engagement by dogs 19 and 21 of the lever 17. Dog 21 is pivotally secured to lever 17 by pin 31, while dog 19 with its tail 34 is pivotally secured to ears 15 via pin 30. Displacing rod 32, which protrudes from one end of pin 31, seats on tail 34 of dog 19.

The intermediate member 300 as seen in FIG. 3 is generally tubular and is interposed between the support case 2 and the stem member 100. As noted above, the double rack 301, represented in FIGS. 1, 2, and 3, is mounted on the intermediate unit 300, as best seen in FIG. 3, and projects through slit 9 of the support case 2, as best seen in FIGS. 1 and 2. As best seen in FIG. 2, the double rack 301 comprises a first rack 310, having teeth 8 oriented downward, and a second rack 311, having teeth 11 oriented upward. The intermediate member 300 has a slit 309, seen on the right side of FIG. 3. In the starting or rest position, the lower end of the slit 309 is positioned slightly above and in line with pin 260 of the stem member 100. Intermediate member 300 is locked to the stem member 100, in the rest position, by balls 305 which seat in receptacles 307 of the intermediate unit 300 and are partly engaged in holes 144 of stem member 100. The inner, generally cylindrical, component or stem member 100 is mounted essentially coaxially within (located centrally within the support member 2 and) the just described intermediate member 300.

Stem member 100 is a rigid hollow cylinder composed of three parts: handle 111, body 113 and stem 102. As noted above, stem 102 protrudes from the distal end 115 of body 113 and projects through opening 31 in the base 7 of the support member 2. At the upper end of the stem member 100 is a generally T-shaped handle 111, having a transverse bar 145 mounted on the upper end of an elongated, cylindrical gas-filled or fluid-filled bottle 129. Interposed between base 95 of gas container 129 and bottom wall 94 of cavity 146 formed within handle 145 is spring or resilient means 90.

Figure 4:
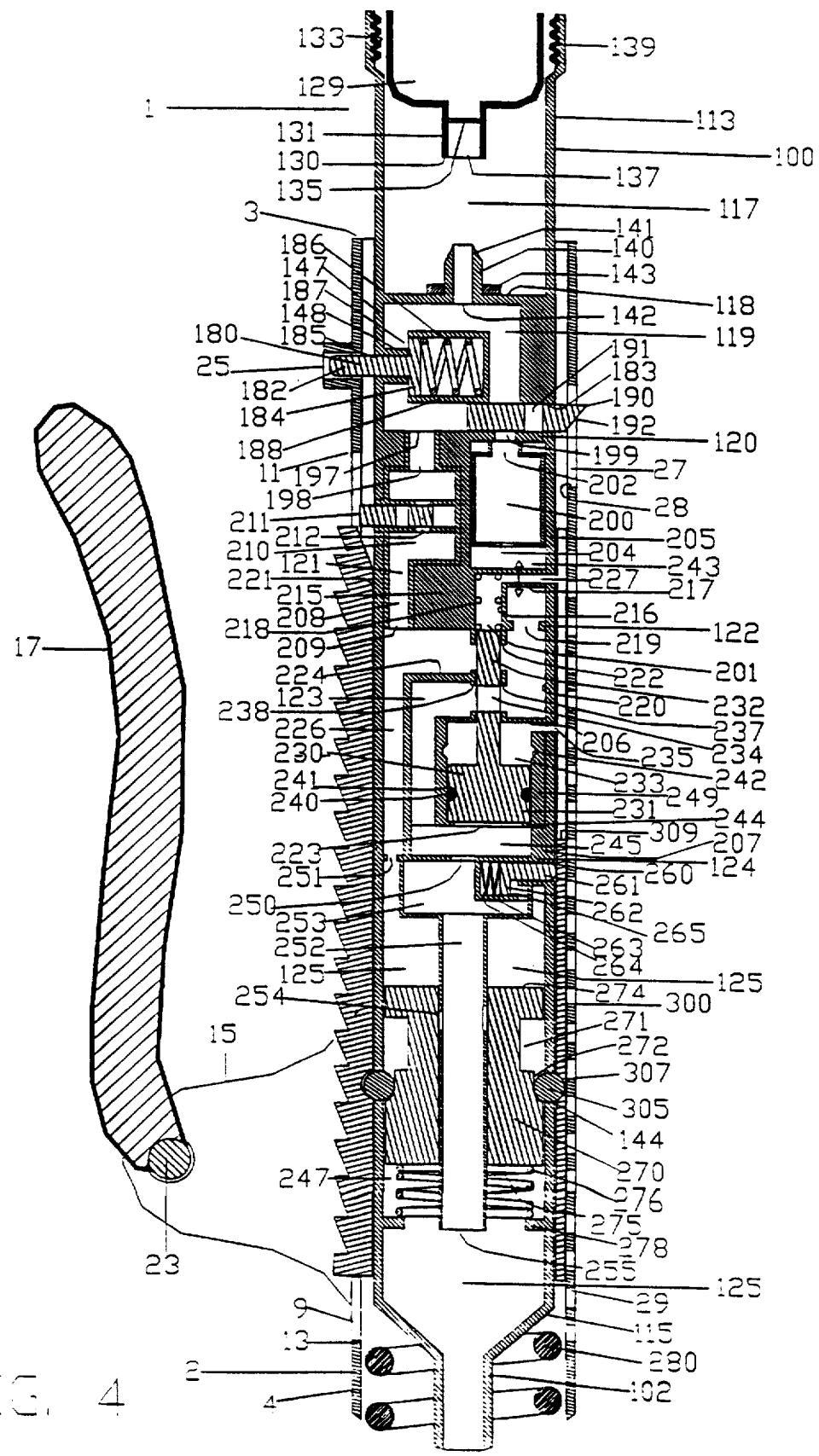
FIG. 4 is an enlarged detail view of the central portion of FIG. 3.
Figure 5:
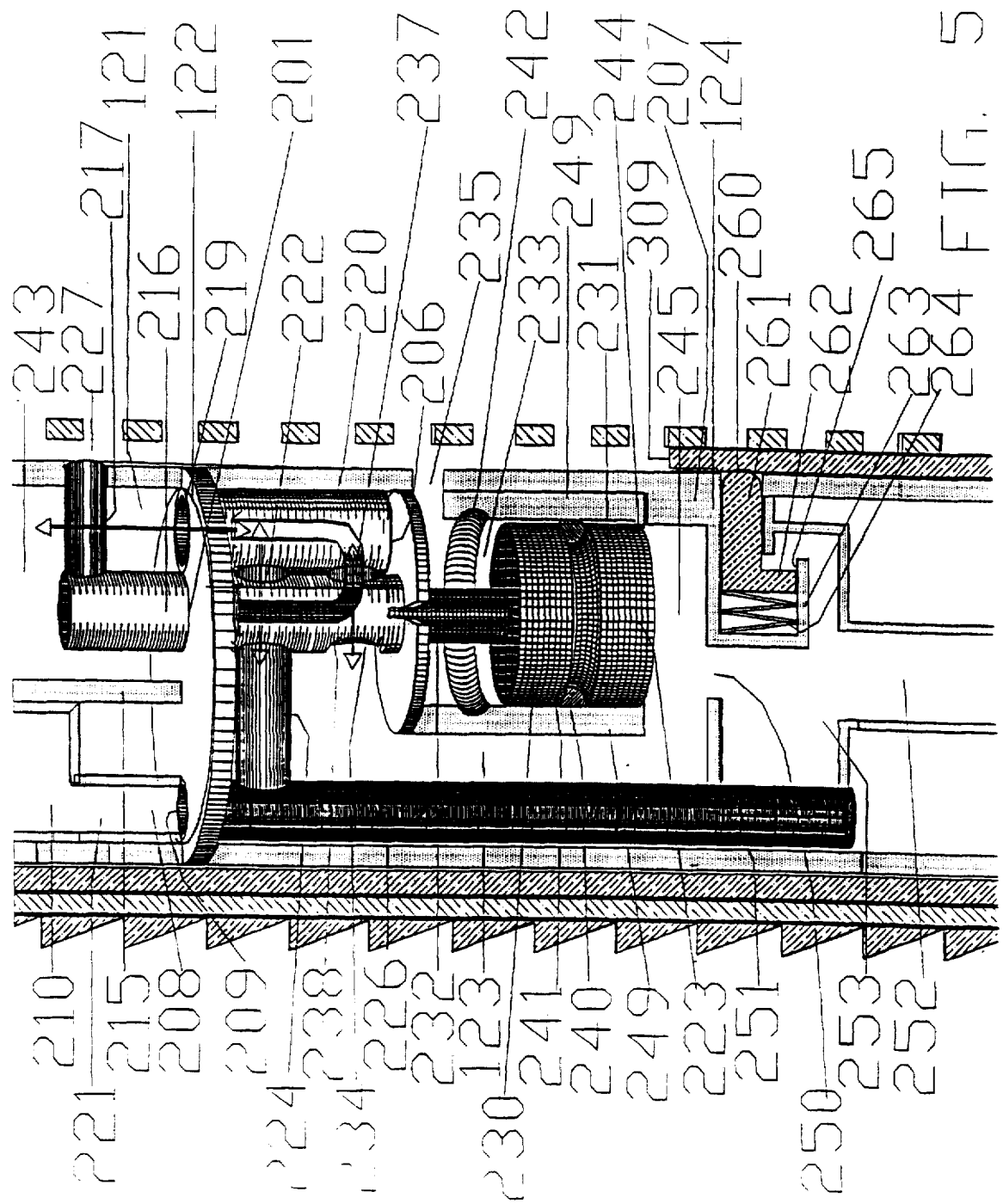
FIG. 5 is a tridimensional representation of a portion of the stem member of the cardiac pump of FIG. 1.

Tooth 91 projecting from side wall or gas container 129 engages longitudinal slit 93 of side wall of cavity 146. Said tooth allows vertical but non-rotatory movement of handle bar 145 in respect to gas container 129 and in respect of the device when gas container 129 is locked to it. The bottle 129 carries an externally threaded portion, as seen at 133 in FIG. 3, and contains a quantity of compressed gas such as air, or fluid under pressure, which is retained within bottle 129 by a suitable seal 135 mounted in nozzle 131 of the bottle 129. The body 113 comprises five chambers 117, 119, 121, 123 and 125. As best seen in FIG. 3, chamber 117 is located adjacent the upper end of the body 113 and has an open end 127 which receives the nozzle 131 of the air bottle 129 and has a diaphragm 118 defining the boundary between chamber 117 and chamber 119. Chamber 117 also has an internally threaded portion 139, which is matable with the external threads 133 of the air bottle 129. Also within chamber 117, a hollow needle 140, having a needle tip 141, is mounted on the diaphragm 118, as by gasket 143. As best seen in FIG. 4, chamber 119 extends between diaphragm 118, at its upper end, and diaphragm 120, at its lower end. Within the chamber 119, is a pin 180 having a pin shaft 182 projecting laterally from pin head 184, which is slidably mounted within a cylindrical pin case 188 and is urged by suitable means, such as spring 186 mounted within the pin case 188, to project through opening 25 of the support case 2, when the cardiac pump 1 is in the rest position. As best seen in FIG. 4, the pin shaft 182 projects, in air-tight manner, through window 185 of side wall 147 of chamber 119. Diaphragm 118 is formed with a central opening 142 which communicates with the interior of hollow needle 141. Also within chamber 119, below the pin case 188, a shutter 190 is mounted for lateral sliding movement through window 183 of the stem member 100 and window 27 of the support case 2. Shutter 190 has a downwardly and inwardly slanted outer end 192 and is provided with an opening 191 located eccentrically and extending vertically through the shutter 190. In the rest position, shutter 190 covers and seals opening 199 of lower diaphragm 120, while uncovering opening 197 of diaphragm 120. Within chamber 121, as best seen in FIG. 4, the opening 199 is connected to inlet 202 of pressure valve 200, while opening 197 communicates with inlet 198 of shut-off valve 210. Pressure valve 200 also has an outlet 204. Shut-off valve 210 also has an outlet 208 and contains a shutter 21 1, which controls passage of air through the outlet 208 and which is movable through opening 212 of shutoff valve 210 to project into slit 9 of the support case 2 above the upper end of the double rack 301. Diaphragm 122, as best seen in FIGS. 4 and 5, defines the boundary between chamber 121, above, and chamber 123, below, and is formed with opening 209, communicating with outlet 208 of shut-off valve 210, and with openings 201 and 219. Opening 201 is connected to pipe 216, which communicates with chamber 123, but projects above diaphragm 122, into space 243 below the pressure valve 200, and is connected to exit pipe 217, which exits through opening 227 of side wall 205 of chamber 121. Chamber 123 is defined by upper diaphragm 122 and lower diaphragm 124 and is best understood from FIGS. 3, 4 and 5. As shown, a pipe 226 extends completely through chamber 123, between opening 209 in upper diaphragm 122 and opening 251 in lower diaphragm 124. Pipe 220 extends downward from opening 219 of upper diaphragm 122, parallel to pipe 216, and terminates at plate 206, which defines the upper end of piston chamber 233. A transverse opening 222 communicates the interior of pipe 216 with that of pipe 220. Similarly, transverse pipe 224 communicates the interior of pipe 216 with that of pipe 226. Below the transverse pipe 224, pipe 216 has a second transverse opening 237 communicating with the interior of pipe 220 and an additional transverse opening 238 which opens to into chamber 121. The piston chamber 233 is enclosed by a cylindrical wall 249 and has a piston 230 slidably retained therein. Piston 230 has a piston head 231 and a piston shaft 232, which extends slidably into the lower end of pipe 216. As seen in FIG. 4, a spring 218 is located within pipe 216, above the end of piston shaft 232, and bears against the end of piston shaft 232 to urge the piston 230 downward to seat against annular retainer 244. The piston shaft 232 is formed with a transverse opening 234 which, in the rest position, is aligned with opening 237 of pipe 220 and with transverse pipe 224, which communicates with pipe 226. Piston 230 is also formed with an annular recess 241, which seats piston ring 240. Also, the cylindrical wall 249 of the piston chamber 233 has an annular recess 242, formed adjacent the upper end thereof, which serves to receive piston ring 240 to releasably lock the piston 230 in its upper position, as more fully described below, and has a lateral opening 235 communicating with the exterior of the cardiac pump 1 above recess 242. Below piston 230, space 245 separates the lower surface 223 of piston 230 from lower diaphragm 124 of chamber 123. As noted above, diaphragm 124 has an opening 251, which receives pipe 226, and has a central opening 250 which communicates with the expanded proximal end 253 of pipe 252 in subjacent chamber 125. Chamber 125 extends between diaphragm 124, at the upper end, and the open lower end 115 of body 113 of the stem member 100. Within the expanded upper end 253 of pipe 252 is a pin case 263, containing a pin 261, having a pin head 262, and having a spring 264 mounted within the pin case 263, behind the pin head 262, to normally urge the pin 261 laterally outward to project through opening 260 on the wall of the stem member 100 pressing against the wall of the intermediate member 300, just below slit 309 of intermediate member 300.

Figure 6:
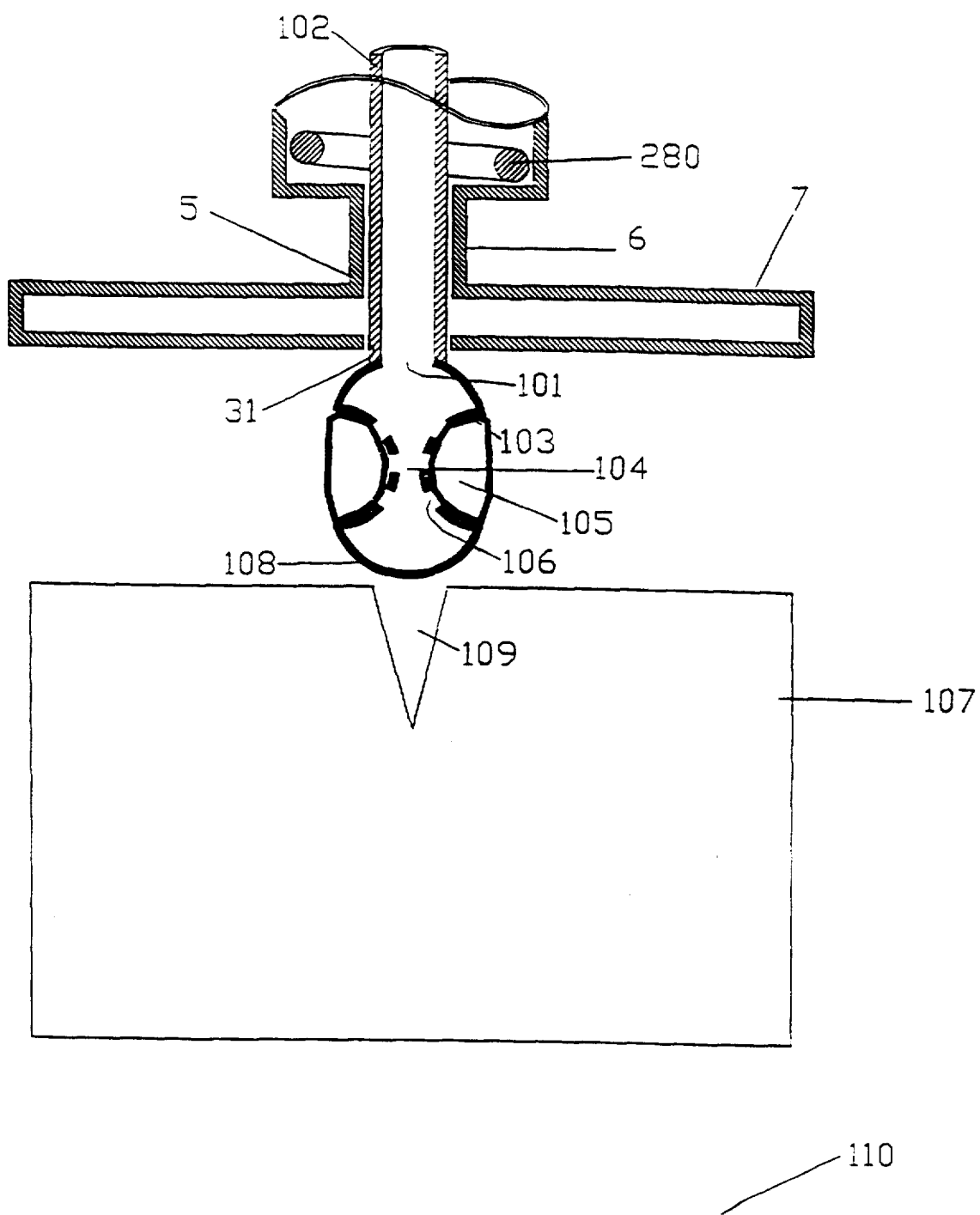
FIG. 6 is an enlarged vertical section of the lower tip of the cardiac pump of FIG. 1.

Pipe 252 extends downwardly within chamber 125 and terminates at the level of flange 275, which serves as a seat for piston 270. Piston 270 is sliceable mounted about pipe 252 and, in the rest position, is located to close transverse openings 254 of pipe 252. Piston 270 is formed with an annular recess 271 with a subjacent annular receptacle 272. In the rest position, balls 305 sit in window 144 of stem member 100 and are retained between receptacle 272 of piston 270 and receptacle 307 of the intermediate member 300 to releasably lock the stem member 100 to the intermediate member 300. Spring 276 is seated on flange 278 and serves to normally urge the piston 270 upward to cause receptacle 272 to retain the balls 305 in their "locked" position. As best seen in FIG. 3, a large spring 230 is located within the lower end of the support case 2 and bears against the lower end 115 of the stem member 100 to urge the stem member 100 upward. As seen in FIGS. 3 and 6, an elongates hollow stem 102 extends downward from the lower end 115 of the stem member 110 and exits through opening 31 of the flat base 7 of the support case 2 to support a blunt end 104 of spheroid shape having a circular groove 103 which contains an expandable member such as balloon 105, which is folded when the cardiac pump 1 is in its rest position.

The stem end, or stem tip, 104 is blunt in order to avoid injuries such as puncture wounds and lacerations to the intrathoracic organs. The relatively small size of the stem end meets little resistance from the chest wall structures that it has to transpass in order to reach the chest cavity, once a skin incision is done, as it will be described below. Stem 102 communicates with the interior of stem end 104 through opening 101 and communicates with balloon 105 through openings 106 within groove 103. Stem end 104 has a blunt end 108 and is generally in the form of a hollow dome, FIG. 6 also diagrammatically shows the anterior thoracic wall 107, with the skin incised at 109, together with the underlying chest cavity 110 containing the heart 69.

Description of the Operation of Embodiment I

To apply the cardiac pump 1, the operator makes a small incision 109 in the patient's skin adjacent the 4th or 5th intercostal space along the left sternal border of the patient or in the subxyphoideal region.

Figure 7:
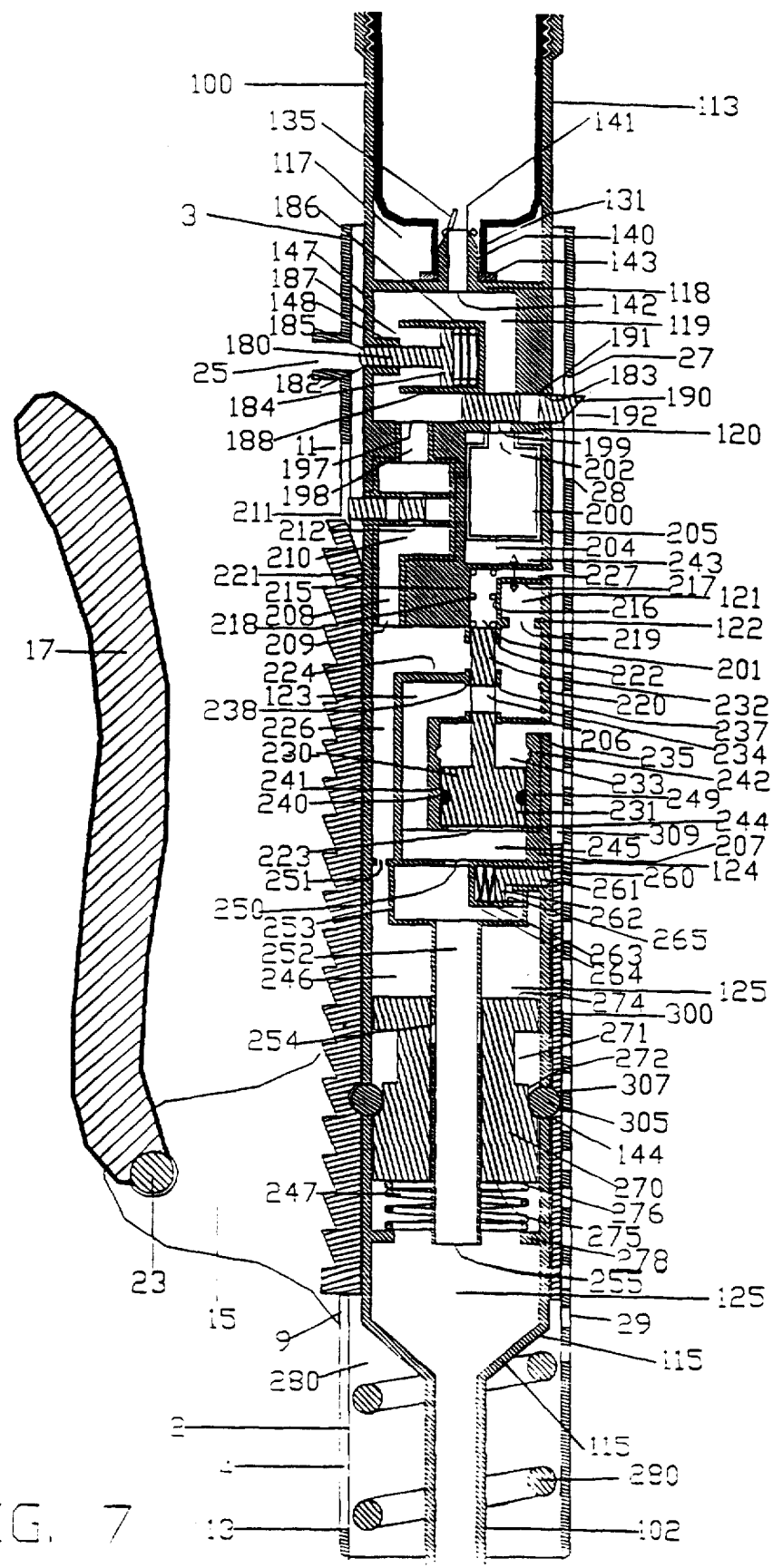
FIG. 7 is a view, similar to that of FIG. 4, showing the cardiac pump of FIG. 1 in its second stage of operation.

The skin incision is carried out with a suitable surgical instrument such a lancet, or surgical knife, preferably provided with an arrest: to prevent deep penetration. After appropriate sterilization, the cardiac pump 1 is placed on the patient's chest with the tip 104 of stem 102 inserted into the incision 109. When this is done, the stem tip 104 will be partially buried under the patient's skin within the thoracic wall 107, but will not have entered the chest cavity 110, and base 7 of the support case 2 will be seated on the appropriate area of the chest wall 107. Next, the operator rotates handle bar 145, causing threads 133 of the air bottle 129 to engage threads 139 of upper chamber 117 of the stem member 100, and drawing the adapter 131 of the air bottle 129 toward needle 141 until the needle tip 140 of needle 141 enters the adapter 131 and pierces seal 135, as seen in FIG. 7, allowing the compressed air contained within the air bottle 129 to flow through needle 141 and opening 142 in diaphragm 118 into chamber 119 of the stem member 100. The operator continues to screw the handle 145 until a tight seal is obtained by the adapter edges 130 pressing firmly against gasket 143. As the compressed air enters chamber 119, the air pressure will bear against pin head 184 of pin 180, driving pin 180 medially against spring 186 to remove pin shaft 182 from projecting through window 25 of support case 2 and, thus, unlocking the main unit 100 from the support case 2.

If the air pressure is insufficient, or if a leak allows the air to escape, pin shaft 182 of pin 180 will not disengage from window 25 and the stem member 100 will remain locked to the support case 2, thereby preventing further operation of the cardiac pump 1. If the air pressure is adequate to actuate pin 180 and, hence, to unlock the stem member 100 from the support case 2, the operator will grab the device at level of the proximal end of the support case, and, while exercising down pressure upon the handle of the stem member, he will repeatedly press lever 17, causing the dogs 19 and 21 to act on the racks 311 and 310, respectively, and to displace the double rack 301 downward.

More precisely, a displacement of handle 18 of lever 17 toward double rack 301 will cause a downward movement of dog 2 pivoted on pin 31 of arm 16 of lever 17: the downward movement of dog 21 which is engaged in rack 310, with upwardly oriented teeth, will result in a downward displacement of rack 310. While aim 16 of lever 17 moves downward, pin 32, protruding from one end of pin 31 will displace tail 34 of dog 19 toward rack 311, releasing dog 19 from rack 311, with downwardly oriented teeth, just before downward movement of rack 310 is initiated, and locking rack 311 immediately after downward advancement of rack 310. Downward advancement of rack 310 in turn will carry intermediate member 300 and stem member 100 downward, due to the interlocking performed by balls 305 sitting in windows 144 of the stem member 100 and in receptacle 307 of intermediate member 300. Balls 305 are retained in windows 144 and receptacle 307 by the annular receptacles 272 of piston 270, which is urged to its upward position by spring 275 acting between flange 278 of the stem member 100 and the lower surface 275 of piston 270.

As it can be understood from FIG. 7, after the intermediate member 300 and stem member 100 are advanced a predetermined the length with respect to the support case 2, preferably about ½ centimeter, by the operator acting on the lever 17, shutter 190 will be displaced medially, due to the edge 28 of window 27 bearing against the slanted end 192 of shutter 190. This displacement of shutter 190 will permit the compressed air to enter pressure valve 200 by passing through opening 199 of diaphragm 120 and inlet 202 of the pressure valve 200. The compressed air will exit, through outlet 204 of pressure valve 200, at a preestablished pressure and will travel through opening 219 of diaphragm 122 connected pipe 220, opening 237, window 234 of piston shaft 232, then into chamber 123, opening 250 of diaphragm 124, expanded end 253 of pipe 252, through pipe 252, space 247 below piston 270, through the elongated hollow stem 102 and opening 101 into tip 104 and will attempt to pass through openings 106 to inflate balloon 105. However, balloon 105 will be presented from inflating due to the inextensibility of the surrounding chest wall structure 107. As a result, the air pressure within the pathway, just described, will quickly reach equilibrium with the pressure at outlet 204 of the pressure valve 200. As this occurs, the air pressure within this pathway will act upon the lower surface 223 of piston 230 and will force piston 230 to move upward, against the urging of spring 218, until piston ring 240 becomes seated in annular recess 242 of piston chamber 233, locking piston 230 against further upward movement and aligning opening 234 of the piston shaft 232 with window 222 of pipes 216 and 220. This movement of piston 230 and piston shaft 232 will close opening 237 and, hence, will force the compressed air from pressure valve 200 to flow through lateral pipe 224, vertical pipe 226, opening 251 of diaphragm 124 and into space 246 above piston 270. At this point, the air pressure in space 246, above piston 270, and in space 247, below piston 270 will be equal. Consequently, piston 270 will be urged into its upward position by the action of spring 276. Moreover, pressure valve 200 serves to regulate the air pressure below the pressure valve 200 and to assure that the air pressure in balloon 105 and in the various pathways between the balloon 105 and pressure valve 200 is less than the air pressure within the air bottle 129. This is a second safety feature and assures that the air pressure within the balloon 105 will be insufficient to cause disruption of the chest wall structure 107. The automatic arming of the cardiac pump 1 is now completed, within a few seconds of initiation of the operation, and the cardiac pump 1 is ready for further operation.

Figure 8A:
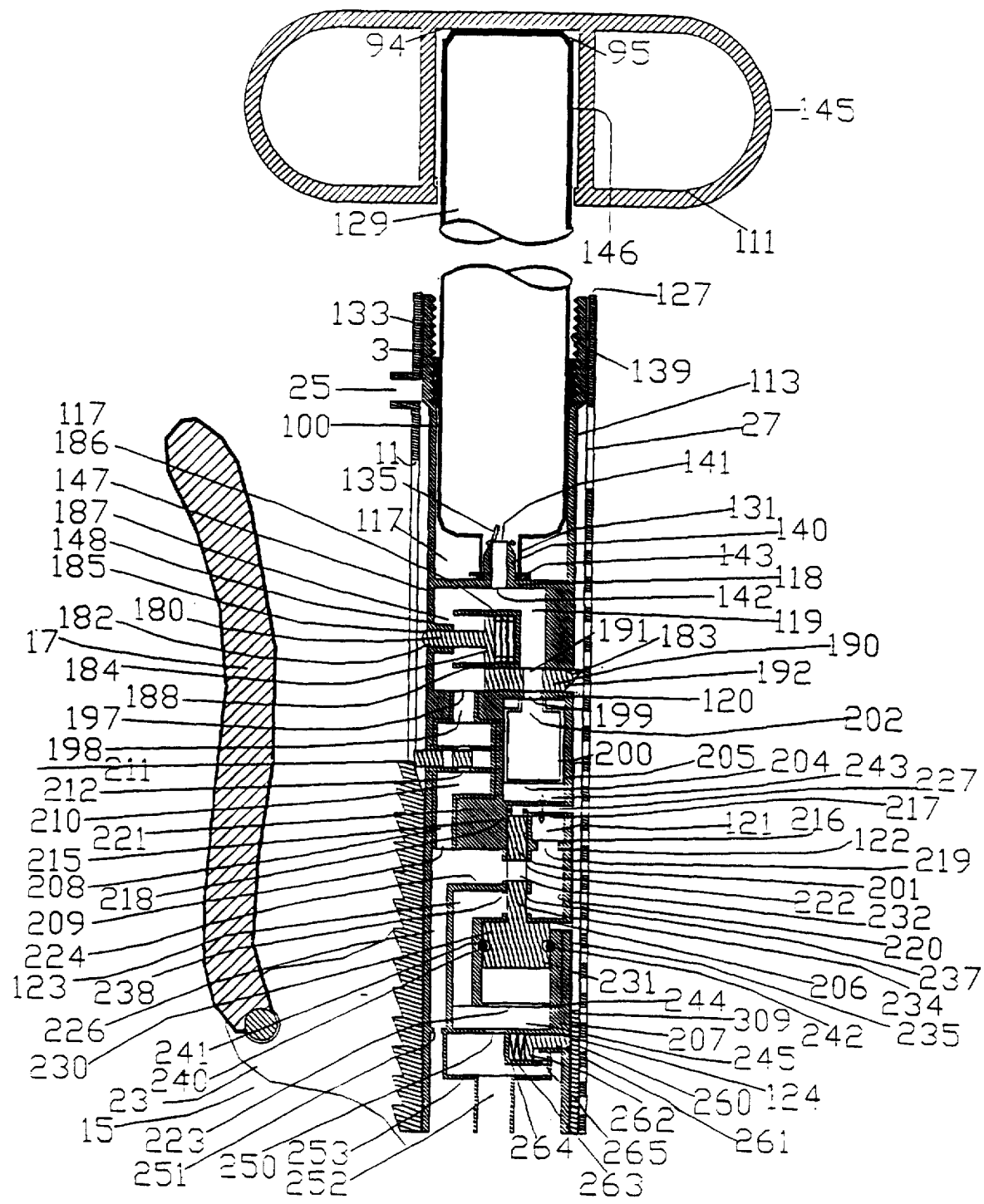
FIG. 8 is a view, similar to that of FIG. 3, showing the stem tip of the cardiac pump of FIG. 1 at the instant it enters the patient's chest cavity.
Figure 8B:
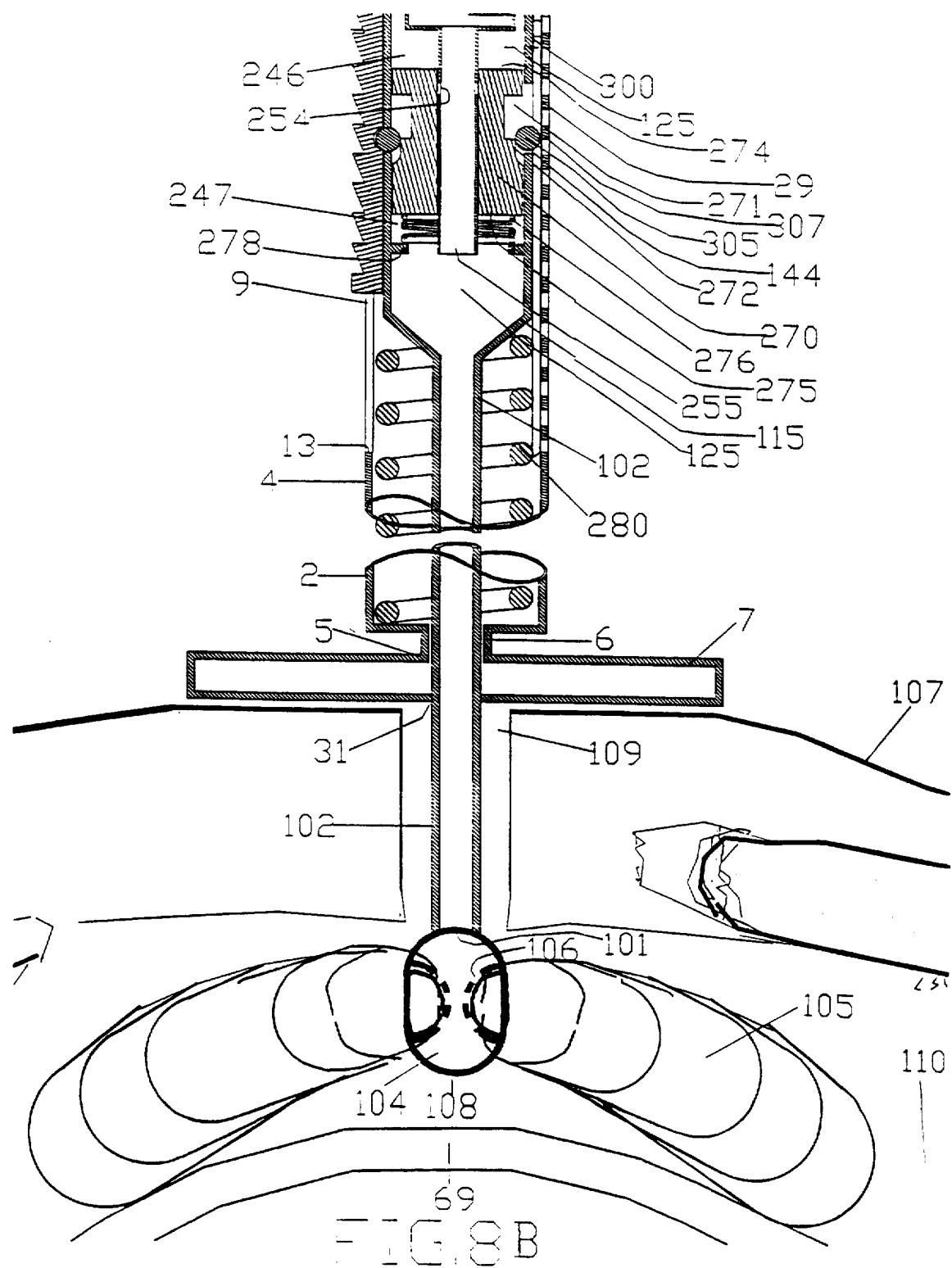

In the next stage of the operation, the operator continues actuating lever 17, causing further advancement of the stem tip 104 through the chest wall structure 107 toward the chest cavity 110. As seen in FIG. 8, the instant that the stem tip 104 passes out of the chest wall structure 107 into the chest cavity 110, the balloon 105 will expand, due to the fact that the balloon 105 is no longer enclosed by the chest wall structure 107 and the compressed air within the stem 102 is able to pass through openings 106 into the balloon 105. The expansion of the balloon 105 will result in a pressure drop within space 247, below piston 270. Because piston 230 has been forced to its upward position, as described above, air can no longer flow through opening 234 of piston 230 to re-supply space 247. Consequently, the air pressure in space 246, above piston 270, will exceed the air pressure in space 247, below, piston 270, and will drive piston 270 downward, against the urging of spring 276. As piston 270 is driven downward toward flange 278, it will expose windows 254 of pipe 252, permitting air form space 246, above piston 270, to pass into pipe 252 and, thus, through stem 102 to further inflate the balloon 105.

The forward movement of the piston 270 also causes balls 305 to be transferred from the recesses 272 into the larger recess 271 of piston 270, which allows the balls 305 to disengage from windows 144 of the stem member 100 and, thus, unlocks the stem member 100 from the intermediate member 300, which prevents lever 17 and double rack 301 from causing any further advancement of the tip 104 into the chest cavity 110. Simultaneous with the unlocking of the stem member 100 from the intermediate member 300, spring 280 acts between the distal end 5 of the support case 2 and the lower end 115 of the stem member 100, forcing the stem member 100 to move upward relatively to support case 2 and to intermediate member 300, which, at this stage, are interlocked one to the other. Intermediate member is locked, at this stage, to support case 2, being prevented to slide upward relatively to support case 2 by dog 21, said dog 21 being anchored to support case 2 and engaged to rack 310 of intermediate member 300. As a consequence of the upward movement of the stem member 100 in respect to the intermediate member 300, pin 261, which is part of, and is anchored to, stem member 100, will align with opening, or slit, 309 formed in intermediate member 300. When pin 261, which is constantly urged outwardly by compression spring 264, aligns with opening 309 of intermediate member 300, being no longer retained in its retracted position by the wall of the intermediate member 300, pin 261 will promptly engage in said opening 309, by gaining access to it. By gaining access to slit 309 of intermediate member 300, pin 261, which continues being urged outwardly by spring 264, will project against the vertical series of holes, or openings, 29 formed in the wall of support case 2, said vertical series of openings being so located to face the vertical slit 309 of the intermediate member. Stem member 100 will continue to move upward in respect to intermediate member 300 and support case 2 in response to action of spring 280, until its pin 261, after gaining access into slit 309 of intermediate member 300 and being forced to press against the wall of the support case 2 by spring 264, finally engages into the first available hole of the series of holes 29 formed in the wall of the support case 2 in correspondence of vertical slit 309 of intermediate member 300. As soon as pin 261 of stem member 100 engages into one of said holes 29 of support case 2, stem member 100 will stop its upward movement, and will lock to support case 2. Of course, although the above sequence is descriptively time consuming, it should require just a fraction of a second or so to complete as a device operation.

This serves to prevent accidental advancement of the stem 104 of the stem member 100 prior to full inflation of the balloon 105. Also, the unlocking of the stem member 100 from the intermediate member 300 renders lever 17 ineffective, which provides a tactile indication to the operator that the stem member 100 has been unlocked from the intermediate member 300 and is now locked to the support case 2. In response to this tactile signal, the operator presses the shutter 211 of the shut-off valve 210 inwardly to allow high pressure air from air bottle 129 to pass through outlet 208 of the shut-off valve 210 and through stem 102 and tip 104 to produce full inflation of the balloon 105, thus bypassing the pathway of pressure valve 200.

The balloon fully inflated will assume a cup or dome shape in order to embrace the heart. This high pressure air will also flow into the expanded end 253 of pipe 252 and will bear against the head 262 of pin 261, driving pin 261 inward, against the urging of spring 264, to cause pin 261 to withdraw from opening 29 of the support case 2 and, hence, unlocking the stem member 100 from the support case 2 to permit the pumping operation.

Figure 9:
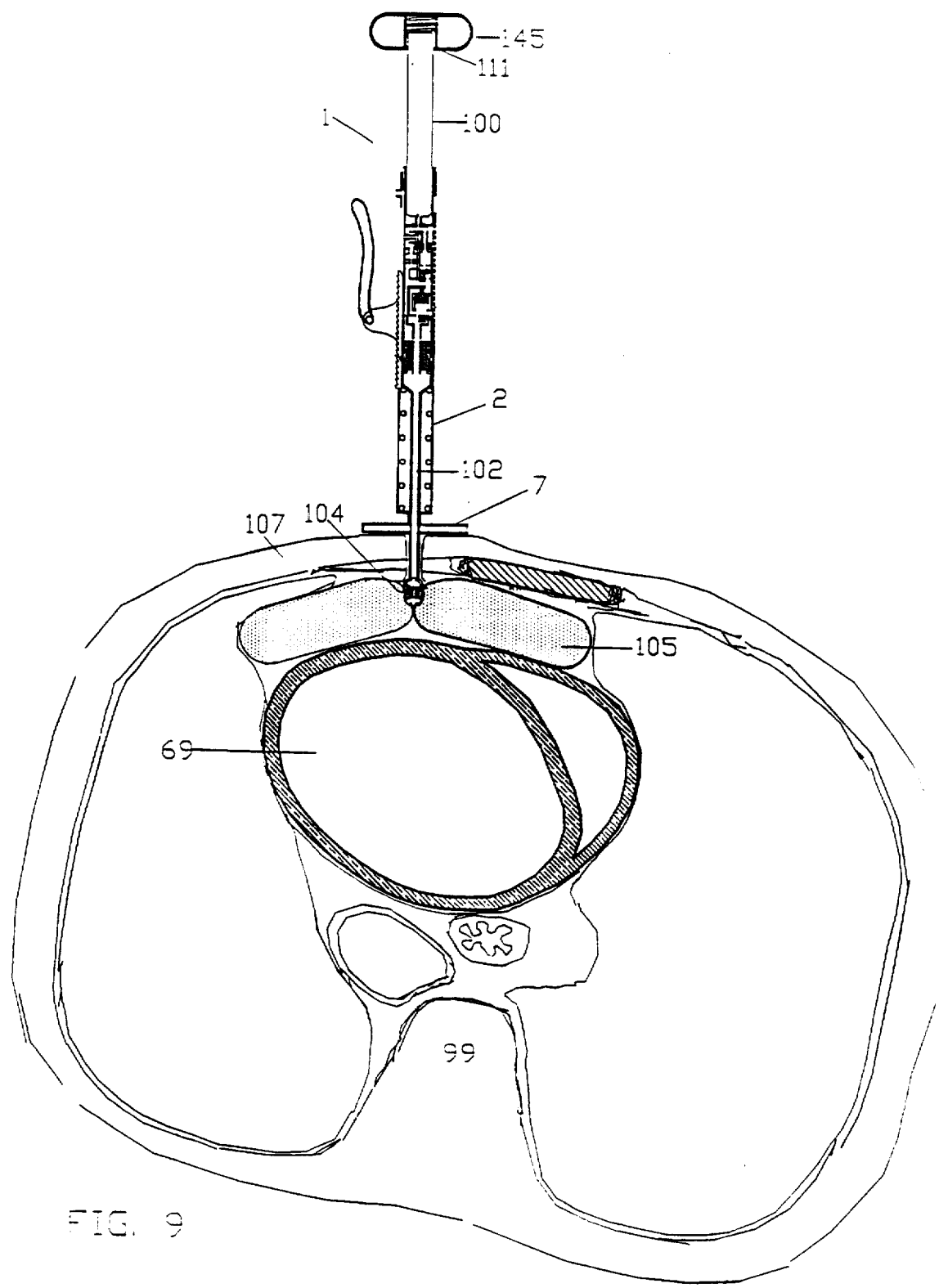
FIG. 9 is a view similar to that of FIG. 3 showing the stem tip of the cardiac pump of FIG. 1 with the expandable member fully inflated prior to compression of the heart.
Figure 10:
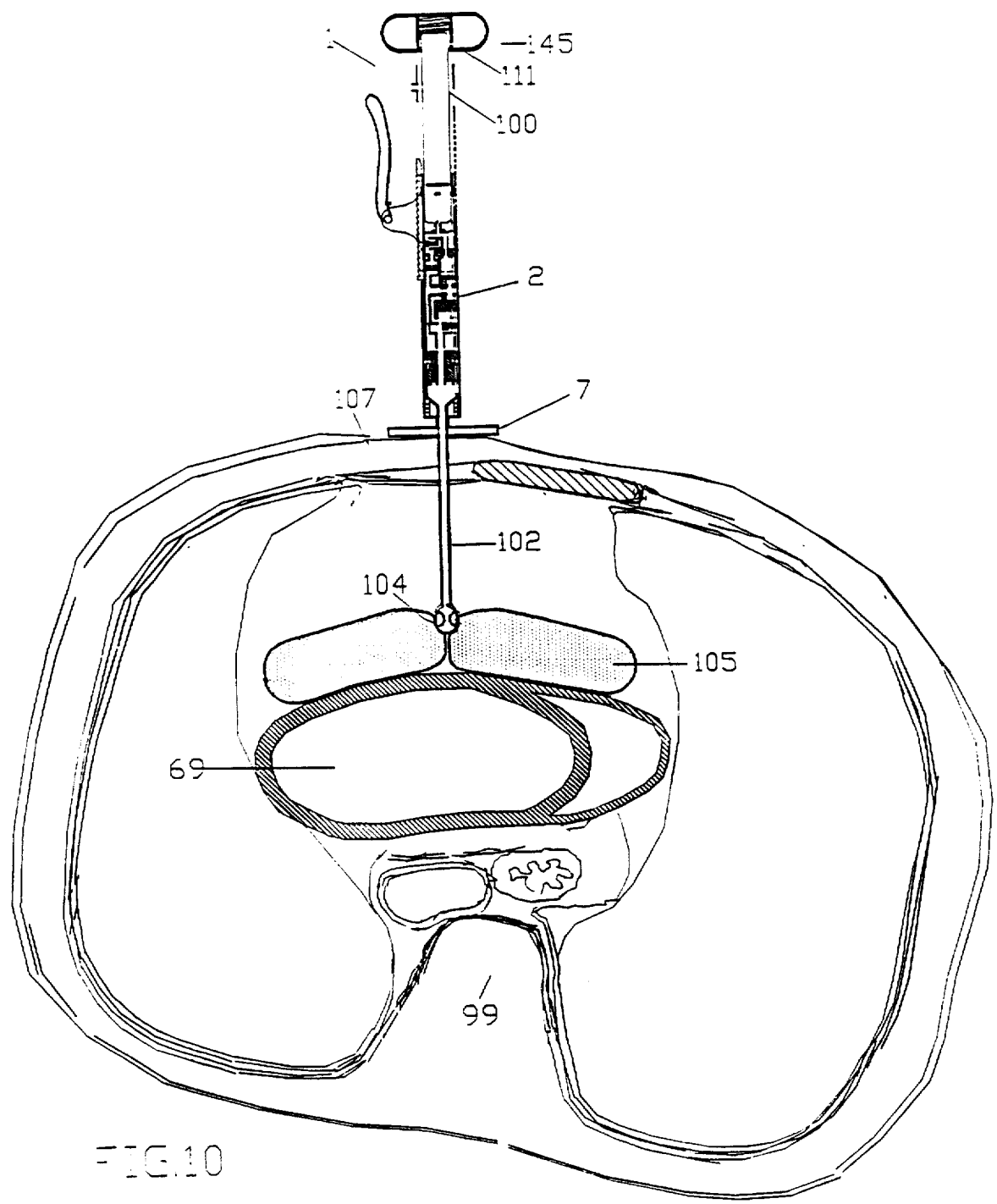
FIG. 10 is a view similar to that of FIG. 9 in a further stage showing the actual the compression of the heart against the vertebral column.

As shown in FIGS. 9 and 10, to perform the pumping operation, the operator alternately applies downward pressure to the handle 145 and releases such pressure. Since the stem member 100 is now unlocked from both the intermediate member 300 and from the support case 2, downward pressure on the handle 145 will be carried through the stem member 100 and will be applied through stem 102 to the balloon 105, causing the balloon 105 to be pressed against the heart 11 and, as pressure is applied to the balloon 105, to compress the heart 11 against the thoracic spine 13. Contraction of spring 90 will prevent injury to the heart if excessive pressure is applied after full compression of the heart against the thoracic spine. Furthermore, since the handle 145 and tip 104 are both integral parts of the stem member 100, the operator receives tactile signals through the structure of the stem member 100 from which, with experience, he can determine the location of the balloon 105 with respect to the heart 11 and the direction and effect of the pressure applied thereto. If the balloon 105 during the pumping operation deflates accidentally, the pressure surrounding pin head 262 will fall allowing spring 264 to urge pin 261 to engage one of the openings 29 of support member 2, thus arresting the pumping operation and signaling to the operator that the handle has to be unscrewed from the device to let the balloon to deflate completely and thus the entire device to be removed and replaced.

When the resuscitation operation has been completed, the operator unscrews and removes the air bottle 129, which allows the balloon 105 to deflate and permits the stem tip 104 and balloon 105 to be easily withdrawn from the chest cavity 110.

Embodiment II

Figure 11:
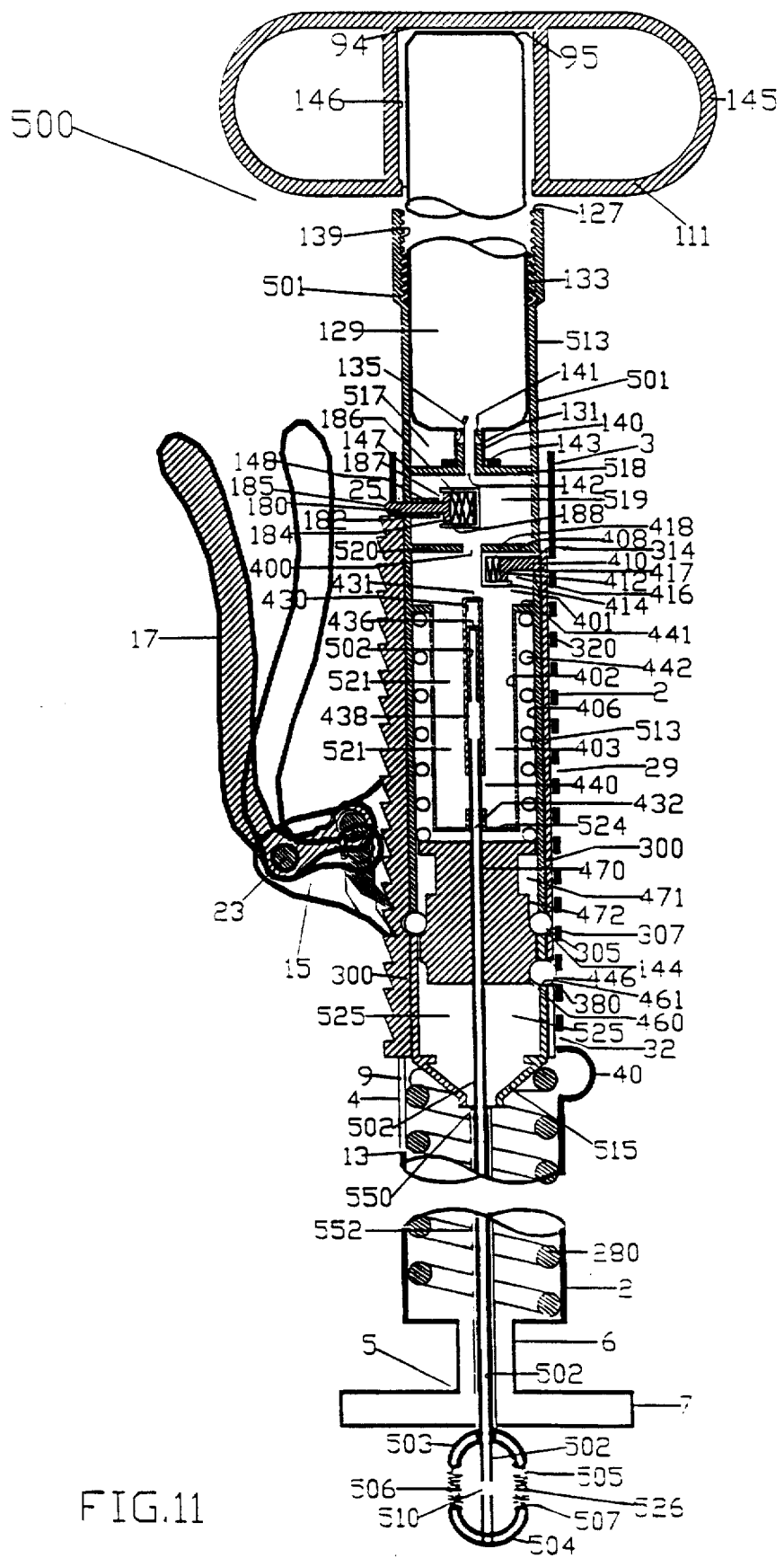
FIG. 11 is a vertical section of an alternative form of the cardiac pump.

FIG. 11 shows an alternative form, indicated generally at 500 of the cardiac pump 1 of FIGS. 1–10. The cardiac pump 500 of FIG. 11 differs from cardiac pump 1 of FIGS. 1–10 mainly in the structure and function of the stem unit generally indicated at 501, as it will be outlined below. The support case 2 and intermediate member 300 are basically the same as those of the cardiac pump 1 of FIGS. 1–10 and the same numbers have been used to identify the corresponding components thereof. The stem member 501 of the cardiac pump 500 is composed of three parts: handle 111, body 513, and stem 502, projecting from the distal end 515 of the body 513. Handle 111 is identical to handle of the cardiac pump 1 of FIGS. 1–10.

The body 513 of stem member 501 of cardiac pump 500 is divided into four chambers: an upper chamber 517, a second chamber 519, a third chamber 521, and a lower chamber 525. The upper chamber 517 is identical to chamber 117 of FIGS. 1–10. As such it has an open upper end 127 to receive the compressed air bottle 129. The lower end of chamber 517 is defined by diaphragm 518, which is also identical to diaphragm 118 of the cardiac pump 1 of FIGS. 1–10. The second chamber 519 extends between diaphragm 518 and diaphragm 520, which is substantially identical to diaphragm 120 of the cardiac pump 1 of FIGS. 1–10, but has only a single central opening 400. Chamber 519 is basically the same as chamber 119 of FIGS. 1–10 and includes pin 180 and related structures as described in cardiac pump 100 of FIGS. 1–10. Shutter 190 of FIGS. 1–10 is no longer present in cardiac pump 500.

Chamber 521 extends between diaphragm 520 and lower diaphragm 524 and is enclosed by side walls 402. Chamber 521 is composed of two adjoining compartments; upper compartment 401 and lower compartment 403. The upper end of side wall 402 is connected by annular flange 441 to the side walls 406 of body 513. Within the upper compartment 401, is a pin case 414 containing a pin 408, having a pin shaft 410 projecting laterally from a pin head 412 and urged outwardly of the pin case 414 by suitable means, such as spring 418, to cause the pin shaft 410 to project outwardly to engage in opening 417 of stem member 501. Pin shaft 410 is retained from further projecting outwardly by upper edge 314 of the wall of intermediate member 300. Pin case 414 also has a window 416 communicating with compartment 401.

A pipe 430 extends axially through compartment 403 of chamber 521 and connects to opening 432, located centrally of diaphragm 524, and the closed upper end 436 of stem 502 is slidably mounted within and concentric with the pipe 430. Inner stem 502 extends downwardly through opening 432 of diaphragm 524 and continues, through lower chamber 525, and passes through opening 550 in the distal end 515 of chamber 525 to reach stem tip 526 continuing in its convex apex 504 of stem tip 526. Inner stem 502 is encircled by outer stem 552 which projects from distal end 515 of chamber 525 of stem member 501 and exits through opening 31 of flat base 7 of support case 2 to continue in tip base 503 of tip 526.

Inner stem 502 is slidably mounted within outer stem 552.

Adjacent its upper end 436, stem 502 is provided with windows 438, while pipe 430 is formed with windows 440, which are normally out of alignment with the windows 438 of stem 502, but which, when aligned, as described hereinafter, allow gas or fluid flow between compartment 403 and the interior of the stem 502. A spring 442 is located between the side wall 402 of compartment 403 and the side wall 406 of body 513, between flange 441 and the upper surface of piston 470. In passing through chamber 525, stem 502 extends axially through piston 470 and is secured to the piston 470 for movement therewith. Piston 470 is formed with an aimular recess 471, having an annular extension 472. In the rest position, balls 305 are seated in extension 472 of piston 470 and project through opening 144 in wall 406 of the body 513 of the stem member 501 to seat in receptacle 307 of the intermediate member 300 to rcleasably lock the stem member 501 to the intermediate member 300. Also, ball 446 seats in an annular recess 460, at the lower end of piston 470, and projects through opening 461 in wall 406 of the body 513 of stem member 501 to scat in window 380 of the intermediate member 300 to prevent downward movement of the piston 470 and, hence, of stem 502.

The stem tip 526 has the same overall shape of stem tip 104 of the cardiac pump 1 of FIGS. 1–10, however it is structurally and functionally different. Stem tip 526 is composed of tip base 503 which, as outlined above, is in continuity with outer stem 552 and a convex apex 504 which, as outlined above, is in continuity with inner stem 502. Between edges 505 of tip base 503 and cdge 507 of convex apex 504 is contained folded expandable member such as balloon 506. Also, the lower end of inner stem 502 is formed with windows 510 which allow air to pass out of inner stem 502 to inflate the balloon 506, when appropriate.

The support case 2 is formed with a receptacle 473, located adjacent the lower end 550 of the body-513 of the stem member 501 when the cardiac pump 500 is in the rest position, for receiving the ball 446, as described hereinafter.

Description of the Operation of Embodiment II

In operation, the cardiac pump 500 of FIG. 11 is placed within skin incision 109, in the same manner as cardiac pump 1 of FIGS. 1–10, with stem tip 526 partially buried under the patient's skin. Compressed air bottle 129 is, then, screwed into chamber 517, causing penetration of seal 135 by needle tip 141 of needle 140, and allowing air to pass through opening 400 into chambers 519 and 521. The air pressure in chamber 519 will result in lateral withdrawal of pin 180, against the urging of spring 186, unlocking the stem member 501 and intermediate member 300 from support case 2 for downward movement with respect to the support case 2, due to the action of lever 17 and the double rack 301, in the same manner as described above with respect to cardiac pump 1 of FIGS. 1–10.

When lever 17 and the double rack 301 have advanced the stem member 501 and intermediate member 300 by a predetermined distance, preferably approximately ½ centimeter, ball 446 will enter receptacle 40 of the support case 2, releasing piston 470 for downward movement by spring 442. However, such downward movement is prevented, at this time, since the tip apex 504 is engaging the inextensible structure of the chest wall 107 and, thus, seraes to prevent downward movement of stem 502 and piston 470. Continued operation of lever 17 on the double rack 301 will, eventually, cause the stem tip 526 to penetrate into the chest cavity 110, whereupon downward movement of the stem tip 526 is no longer impeded by the structure of the chest wall 107. The instant such penetration of the chest cavity 110 occurs, spring 442 will drive piston 470 and stem 502 downward, causing windows 438 of stem 502 to align with windows 440 of pipe 430 and allowing air to pass from chamber 521, through stem 502 and windows 510 to inflate the balloon 506. The downward movement of piston 470 also allows balls 305 to be moved out of extension 472 of piston 470, to enter recess 471 of piston 470 and to disengage from receptacle 307 of the intermediate member 300 and, thus, to unlock the stem member 501 from the intermediate member 300. However, prior to full inflation of the balloon 506, pin shaft 410 of pin 408 will be urged by spring 418 to project through longitudinal slit above edge 314 of the intermediate member 300 into one of the openings 29 of the support case 2 to prevent forward movement of the stem member 501. When the balloon 506 is fully inflated, the air pressure in chamber 521 will rise, causing pin head 412 to drive pin 408 inwardly, against the urging of spring 418, withdrawing pin shaft 410 through slit above edge 314 of the intermediate member 300, out of opening 29 of support case 2, to fully release the stem member 501 for the pumping operation, which is performed in the mamner described above with respect to the cardiac pump 1 of FIGS. 1–10. In case balloon 506 during the pumping operation deflates accidentally, pressure surrounding pin head 412 of pin 408 will fall, allowing spring 418 to urge pin 408 outwardly to engage one of the openings 29 of support member 2. When the resuscitation operation has been completed, the operator unscrews and removes the air bottle 129, which allows the balloon 506 to deflate and permits the stem tip 526 and balloon 506 to be easily withdrawn from the chest cavity 110.

Embodiment III

Figure 12:
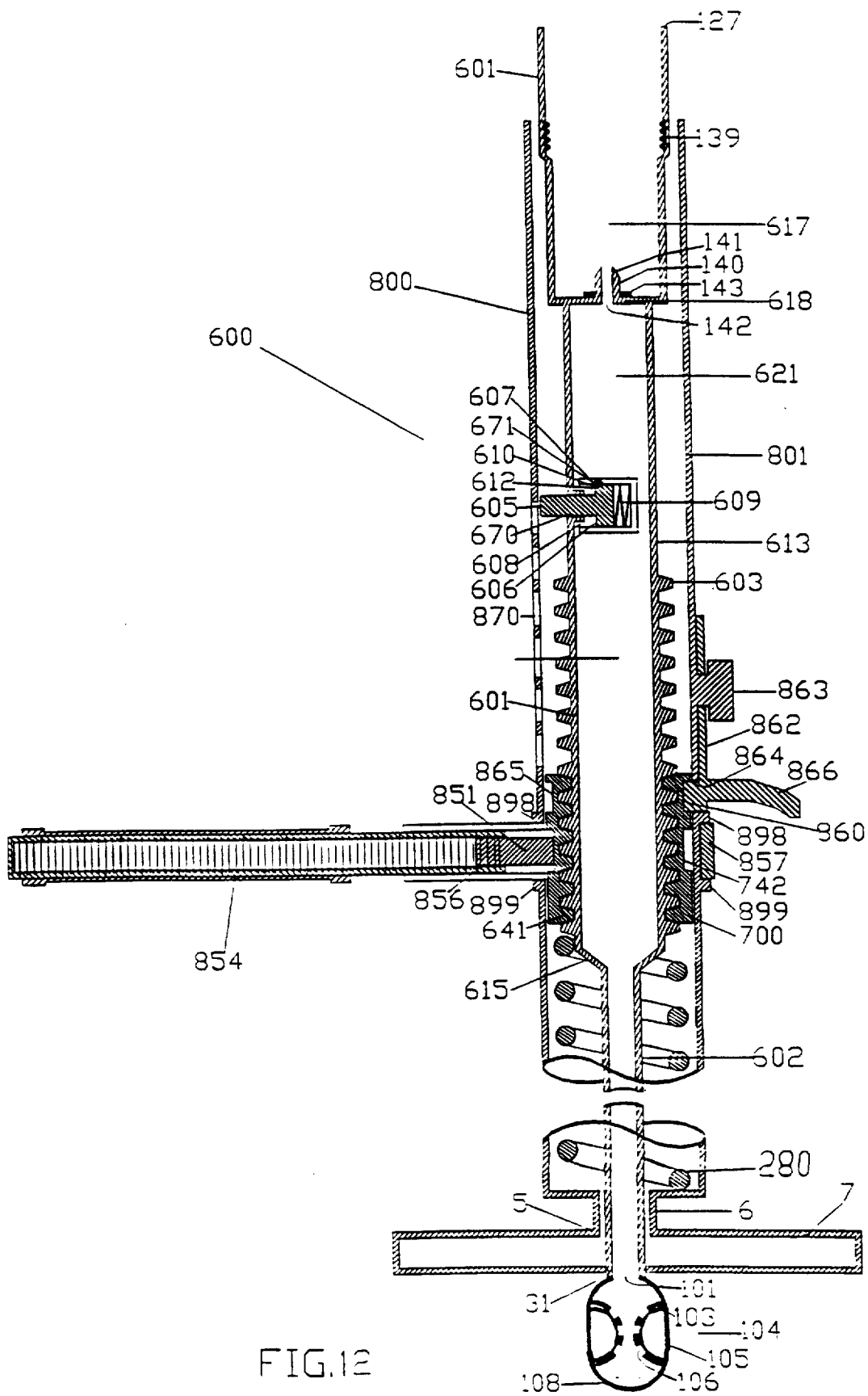
FIG. 12 is a vertical section of another alternative form of the cardiac pump.
Figure 14:
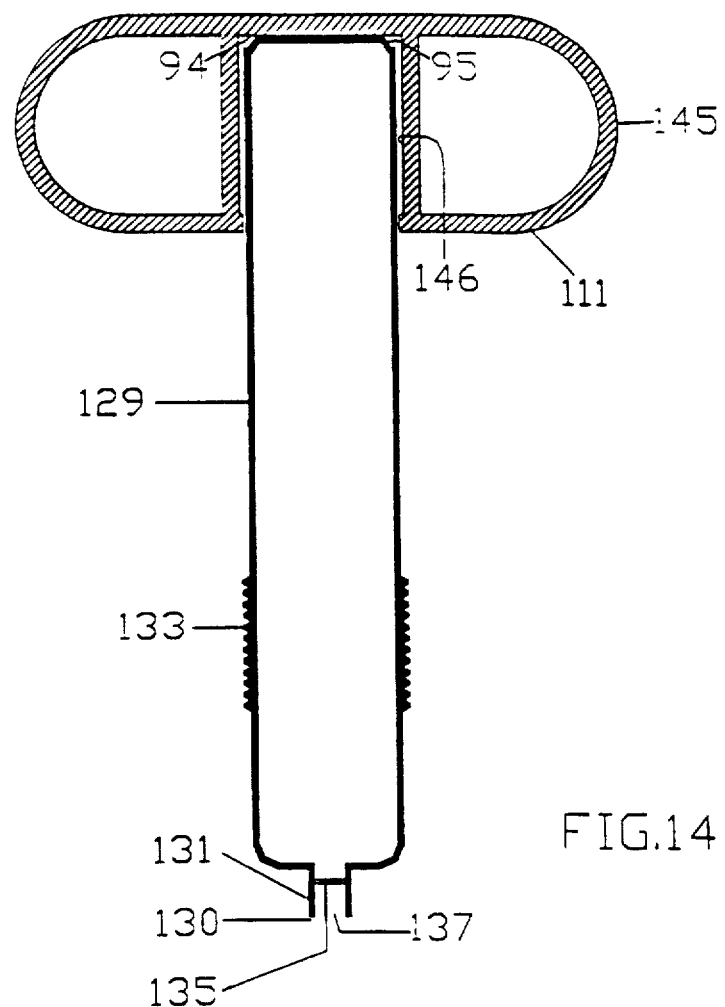
FIG. 14 shows a top view of the lever of the device of FIG. 12.
Figure 13:
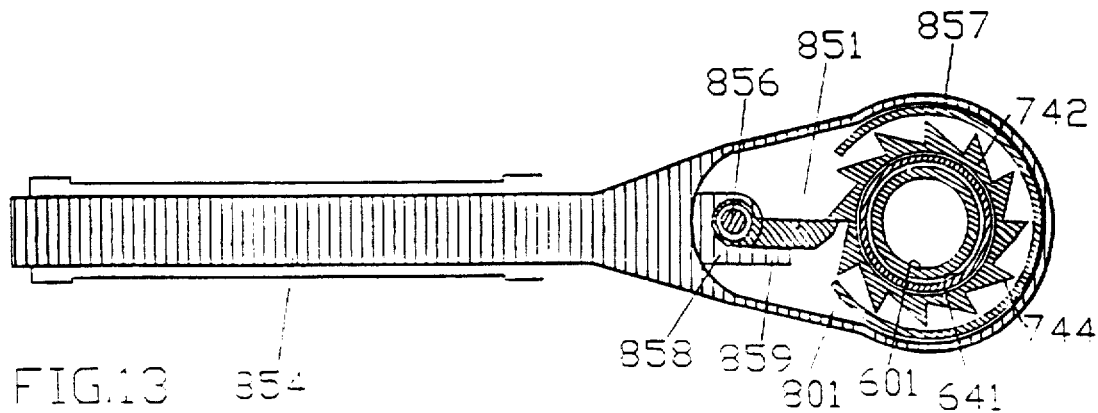
FIG. 13 is a vertical section through the handle portion of the cardiac pump of FIG. 12.

FIGS. 12, 13, and 14, show a further alternative form, indicated generally at 600, of the cardiac pump 1 of FIGS. 1–10, having a support case 800, which is similar to the support case 2 of the cardiac pump 1 of FIGS. 1–10; a stem member 601, and an intermediate member 700. The stem member 601 as shown in FIG. 13, comprises a handle 111, a body 613 and a stem 602 projecting from end 615 of body 613. Handle is mounted atop a compressed air bottle 129, which is threadedly attached to the upper end of a generally cylindrical body 613 of stem member 601. Handle 111, as shown in FIG. 14, is identical in structure and function to handle 111 described for the device shown in FIG. 1 to 10 and to handle of device shown in FIG. 11. Body 613 is divided into upper chamber 617 and lower chamber 621. Chamber 617 is identical to chamber 517 of the cardiac pump 500 of FIG. 11. Diaphragm 618 separates chambers 617 and 621 and has a central opening 142, surrounded by hollow needle 140 which has pointed end 141 and is identical with hollow needle 140 of the cardiac pump 1 of FIGS. 1–10. Chamber 621 extends between diaphragm 618 and the distal end 615 of the body 613, while hollow stem 602 communicates with end 615 of the body 613 and projects through the base 7 of the support case 800 to communicate with stem tip 104, which is identical with the stem tip 104 of the cardiac pump 1 of FIGS. 1–10. Within chamber 621 is a pin case 607 having a window 608 and containing a pin 605 which projects through opening 670 of the wall of body 613 and is formed with a head 606 that is normally urged laterally outward by a spring 609 contained within the pin case 607. However, the action of spring 609 causes the pin head 606 to bear against ball 610, which is seated in receptacle 671 of the pin case 607 and prevents outward movement of the pin 605 until the ball 610 is released as described hereinafter. The exterior of the body 613 is provided with a male threaded portion 603 which mates with the female threaded portion 641 of the intermediate member 700. The intermediate member 700 is interposed between the stem member 601 and the support case 800 and is of generally cylindrical shape, with the female threaded portion 641 located approximately midway of the length of the intermediate member 700, and has an annular rack 742 extending about the exterior of the middle of the intermediate member 700, provided with a plurality of outwardly projecting teeth 744. The support case 800 has a generally hollow, cylindrical body 801 encircling the intermediate member 700 and the stem member 601 and the upper portion of the body 801 of support case 800 is provided with a vertical row of small openings 870 for receiving the pin 605 of the stem member 601.

Lever 854 encircles with its expanded head 857 support member 800 at its midportion and is held in that midportion by the presence of two annular rails 898 and 899.

Lever 854 carries a dog support 858 to which a dog 851 is pivotally secured via a pin 856 and is provided with dog arrest 859 for dog 851. Dog 851 projects through opening 853 of support member 800 and reaches for ratcheting engagement the teeth 744 of the annular rack 742 mounted on the intermediate member 700. The support case 800 also carries a pin 860 mounted externally of support member 800 by a flexible arm 862, which is secured to support member 800 by a button 863 and extends downwardly from the button 863 to allow the pin 860 to project through opening 864 of support case 800 to engage annular recess 865 of the intermediate member 700. A handle 866 projects outwardly from the pin 860 to permit manual actuation of the pin 860.

Description of the Operation of Embodiment III

In use, the cardiac pump 600 of FIGS. 12, 13, and 14, and 10, is placed on the patient's chest either on the anterior chest wall in the fourth or fifth intercostal space or in the subxyphoideal region within skin incision 109, in the manner described above with respect to the cardiac pump 1 of FIGS. 1–10, with the stem tip 104 partially buried within the chest wall structure 107.

The operator then ratchets the lever 854 laterally, while keeping the base 7 of the support case 601 pressing steadily against the patient's chest. This action causes dog 851 to drive the teeth 744 on rack 742 to rotate the intermediate member 700. Since the operator is preventing rotation of the stem member 800, by his grip on handle 145, and since intermediate member 700 is prevented from advancing, by pin 860 projecting through opening 864 and engaging annular recess 865 of the intermediate member 700, the rotation of the intermediate member 700 will cause threads 641 to interact with threads 603 of the stem member 600 to force the stem member 601 to advance the stem tip 104 through the chest wall structure 107 until the stem tip 104 penetrates the chest cavity 110. The gradual and controlled slow advancement will finally result in penetration of the stem tip 104 into the chest cavity 110. Once the passage of a relatively broad stem end 104 is completed and relatively narrow stem 602 is engaged in the chest hole formed by stem end 104, the operator will have an immediate tactile signal of front and side clearance of the stem 602 in the hole formed in the chest wall. Upon receipt of this signal, the operator will cease to actuate the lever 854 and will screw in the air bottle 129, causing needle point 141 of needle 140 to rupture the seal 135 and allowing compressed air from the air bottle 129 to inflate the balloon 105. As the balloon 105 reaches full inflation, the air pressure within the stem member 601 will increase and will drive pin 605 inward, against the action of spring 609, allowing ball 610 to be released from receptacle 612 thus freeing pin 605. The operator will then unlock the intermediate member 700 from the support case 800 by pulling handle 864 of pin 860 to disengage pin 860 from the annular recess 865 of the intermediate member 700 to permit the operator to commence the cardiac pumping by alternately pressing and releasing the handle bar 145 of handle 111. If the balloon 105 should become deflated during the pumping operation, the air pressure within the stem member 601 will fall, allowing spring 609 to urge freed pin 605 laterally outward to project through one of the openings 870 of the support case 800 to lock the stem member 601 to the support case 800 and, hence, to prevent further pumping and possible damage to the heart 69.

Embodiment IV

Figure 16:
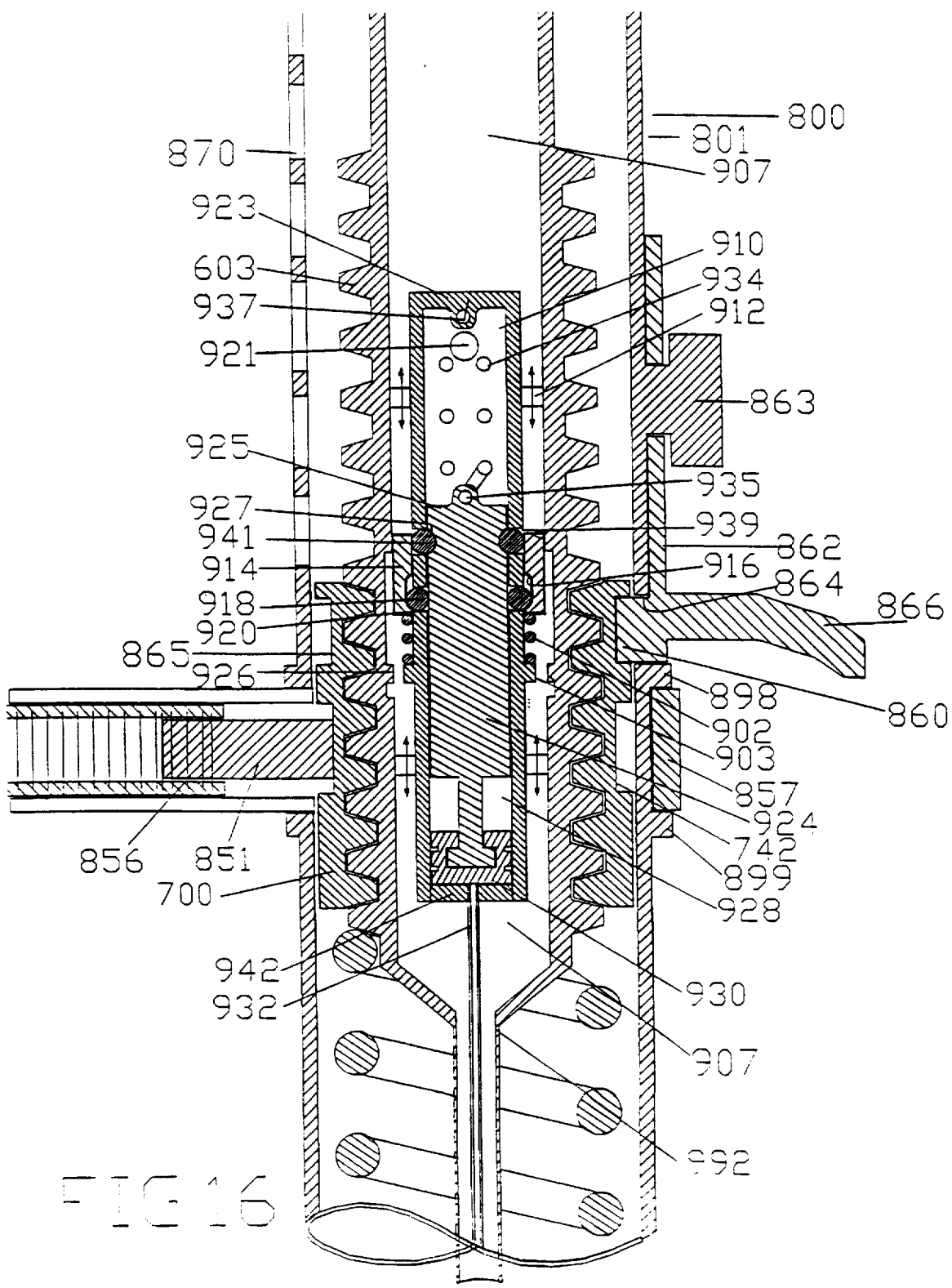
FIG. 16 is an enlarged detail view of the mid-portion of the cardiac pump of FIG. 15.
Figure 17:
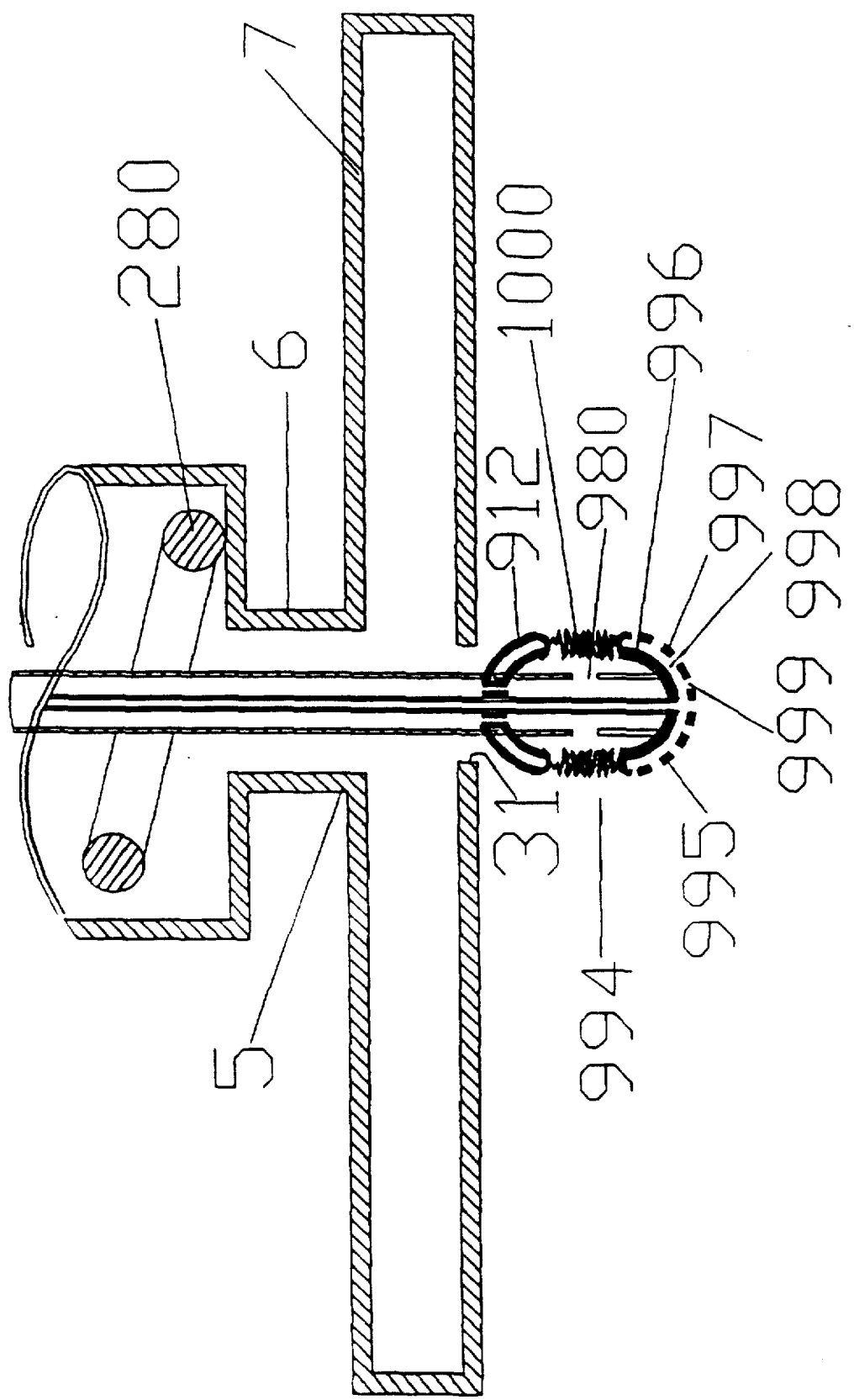
FIG. 17 is an enlarged vertical section through the stem tip of the cardiac pump of FIG. 15.

FIGS. 15, 16, and 17, show another alternative form, indicated generally at 900, of the cardiac pump 1 of FIGS. 1–10. The stem member 901 of cardiac pump 900 is different from those previously described, although the support case 800 and intermediate member 700 are identical with those of the cardiac pump 600 of FIGS. 12–14. The stem member 901 is composed of handle 111, body 913 and stem 992, having a stem tip 994. Body 913 of stem member 901 of pump 900 is divided into three chambers: upper chamber 917, central chamber 919 and lower chamber 907.

Upper chamber 917 is identical to chamber 517 of the cardiac pump 500 of FIG. 11. Diaphragm 918 separates chambers 917 and 919 and has a central opening 142, surrounded by hollow needle 140 with pointed end 141, identical to the one described in the embodiment of FIGS. 1–10.

Chamber 919 contains a pin 180 and a shutter 190, which are identical to the corresponding components of the cardiac pump 1 of FIGS. 1–10, and has a diaphragm 920 formed with a central opening 199, which is normally blocked by shutter 190, and separating the central chamber 919 from the lower chamber 907. Lower chamber 907 contain a cylindrical vacuum chamber 910, which is mounted axially within chamber 907 by a pair of support arms 912 extending between the vacuum chamber 910 and the body 913 of the stem member 901, as best seen in FIG. 16. A sealing cylinder 914 encircles the middle of the vacuum chamber 910 and is normally urged upward by spring 902, bearing against flange 903, which projects radially outward from the vacuum chamber 910. Another flange 926 projects radially inward from the body 913 of the stem member 901 to limit downward movement of the sealing cylinder 914.

The sealing cylinder 914 is fonncd with an inwardly facing annular recess 916. In the rest position of the pump 900, balls 918 are seated in recess 916 and in windows 920 of vacuum chamber 910. The locking piston 924 is axially slideable within the vacuum chamber 910 and carries a sealing cap 930 at its lower end with an annular recess 928 formed immediately above the sealing cap 930. Lower end of chamber 907 of stem member 913 projects in outer stem 992 which slides through hole 31 of flat base 7 of support case 800 to reach stem end 994 firmly supporting both hollow convex apex 995 and solid base 912 of stem end 994.

Inner stem 932 projects from distal end 942 of vacuum chamber 910 and extends concentrically inside hollow outer stem 992, downward to reach and communicate with hollow convex apex 995.

Hollow convex apex 995 has a solid inner wall 996 and an outer wall 997 separated by a space 998 therebetween. Inner stem 932 penetrates inner wall 996 and communicates the space 998 with the lower end 942 of the vacuum chamber 910 within the body 913 of the stem member 901. The outer wall 997 is formed with a plurality of openings 999. Finally, a balloon 1000 is mounted between the adjacent edges of the concave base 912 and the convex apex 995 and windows 980 are formed in the lower portion of outer stem 992 communicating the interior of the balloon 105 with the interior of body 913 of the stem member 901. Lever 854 with annexed structure and pin 860 with annexed structure are the same as the one described for FIG. 12 to 14.

Description of the Operation of Embodiment IV

In use, the compressed air bottle 129 is screwed into upper chamber 917, causing needle point 141 of needle 140 to rupture the seal 135 and allowing compressed air from the air bottle 129 to enter chamber 919 and to displace pin 180 inward, unlocking the stem member 901 from the support case 800. The operator then ratchets lever 854, as described for cardiac pump 600 of FIG. 12–14, causing advancement of the stem member 901 with respect to the support case 800, until shutter 190 is displaced inward by body 801 of the support case 800, causing air to pass through opening 199 into chamber 907 surrounding the vacuum chamber 910. This air pressure drives the scaling cylinder 914 downward, against the urging of spring 902, and allowing balls 941 to move out of the annular recess 927 to unlock piston 924 from the vacuum chamber 910. However, spnrng 934 is unable, at this time, to move piston 924 upward, since such action will cause the sealing cap 930, carried by the lower end of piston 924 to create a vacuum within the vacuum chamber 910 below piston 924, since the chest wall structure 107 prevents air from entering stem tip 994 and passing through inner stem 932 into the vacuum chamber 910. This vacuum will resist the upward urging of spring 934.

However, as soon as the stem tip 994 enters the chest cavity 110, air from within the chest cavity 110 can enter stem tip 994 and flow through inner stem 932 to relieve this vacuum and to allow spring 934 to move piston 924 to its upward position, wherein balls 918 can pass into the annular recess 928, adjacent the lower end of piston 924, to unlock sealing cylinder 914 from piston 924. Upon disengagement of sealing cylinder 914 from piston 924, sealing cylinder 914 will be forced downward by compressed air already present in chamber 907 against the action of spring 902 which urges sealing cylinder upward. Compressed air, by displacing sealing cylinder 914 downward will bypass the sealing cylinder 914 and will flow through outer stem 992 and windows 980 of stem end 994 to inflate the balloon 1000. The operator may then apply periodic pressure to the handle bar 145 to perform the pumping operation. If the balloon 1000 should accidentally deflate during the pumping operation, the air pressure within the stem member 901 will fall, allowing spring 186 to urge pin 180 laterally outward to project through one of the openings 870 of the support case 800 to lock the stem member 901 to the support case 800 and, hence, to prevent further pumping and possible damage to the heart 69.

Embodiment V

Figure 28:
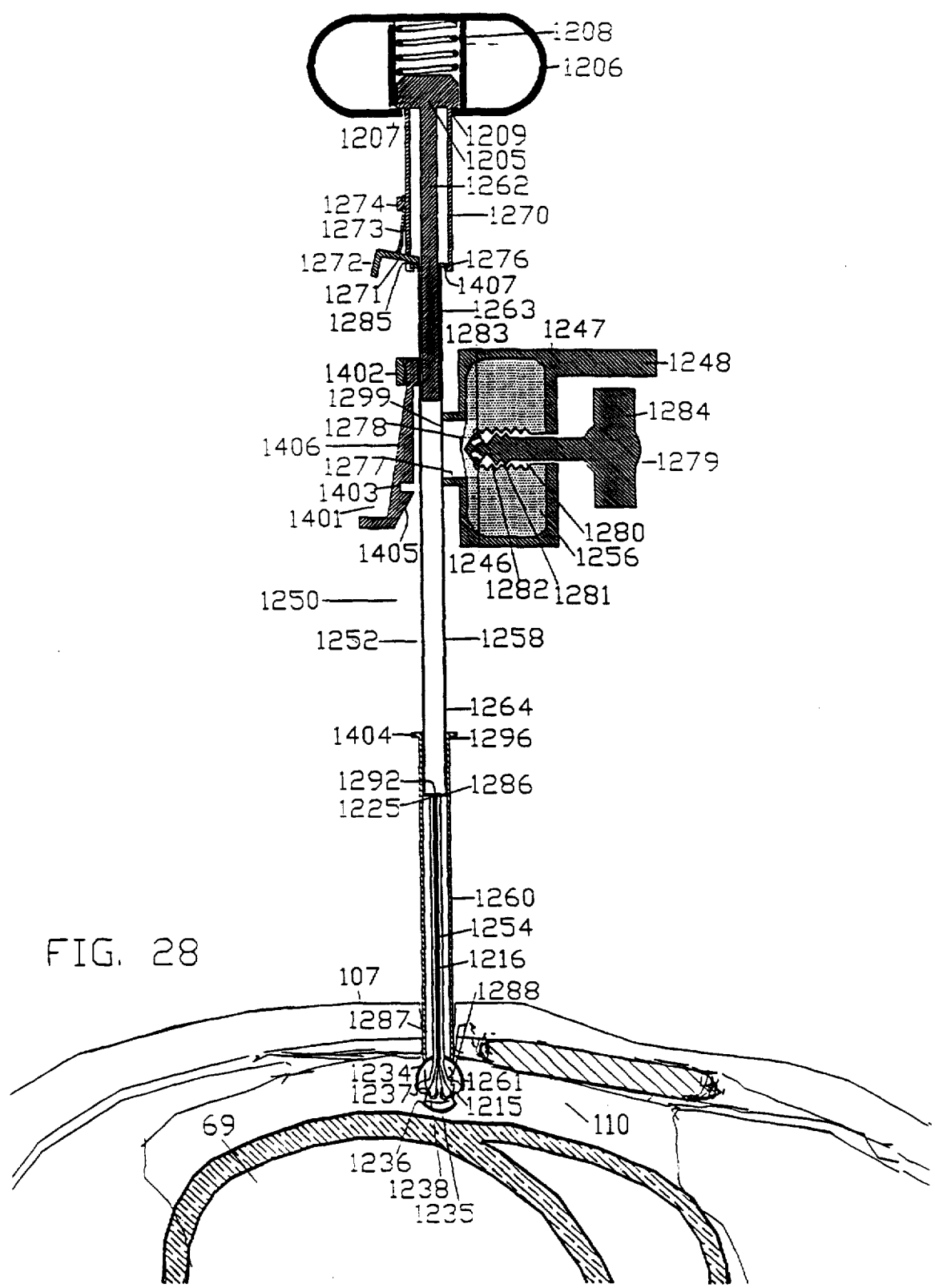
FIG. 28 is a cross-sectional view of an alternative form of the device of FIG. 1 shown after stem tip penetration of the chest cavity.
Figure 29:
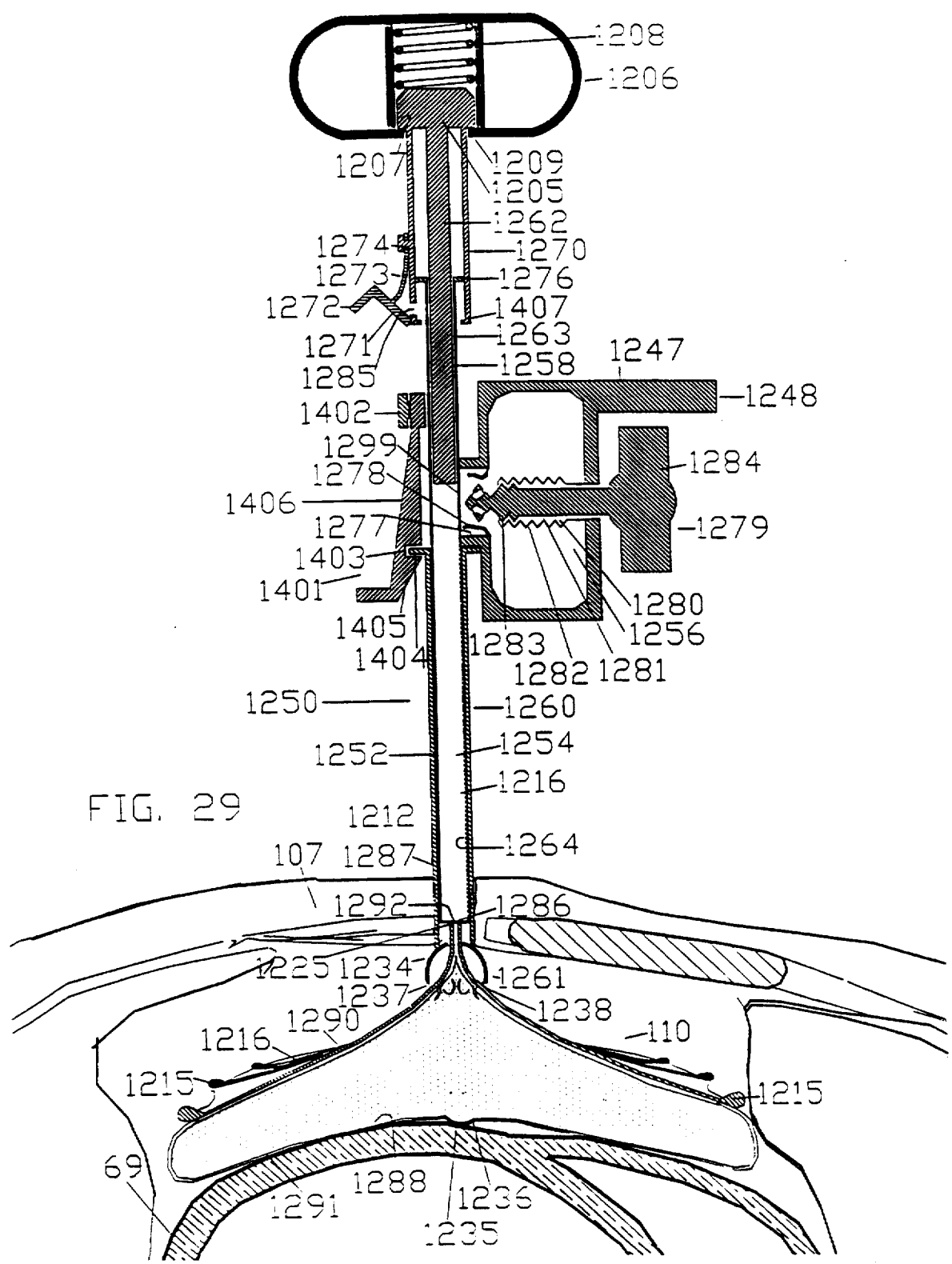
FIG. 29 is a cross-sectional view of the device of FIG. 28 shown after full expansion of the expandable member.

FIGS. 28 and 29 show yet an alternative form of device 1 of FIG. 1. As shown in FIG. 28, which is a cross-sectional view of the device, the device generally indicated at 1250 is composed of three main components: stem member 1252, expandable member 1254 and pneumatic container 1256. Stem member 1252 is composed of upper segment or rod 1262, intermediate stem segment 1258 and lower stem segment 1260. Stem member 1252 is provided proximally with handle 1206. Within handle recess 1207 of handle 1206 is slidably mounted proximal end 1205 of upper stem segment or rod 1262. Proximal end 1205 of rod 1262 is of general cylindrical shape as upper segment stem or rod 1262 but of larger diameter. Spring or resilient means 1208 urges stem member 1252 downward. Circular lid or arrest 1209 in handle 1206 does not permit exit of stem member 1252 from handle 1206 by engaging proximal end 1205 of upper stem segment 1262.

Externally and concentric to the upper portion of upper stem segment or rod 1262 of stem member 1252 is mounted external arrest cylinder 1270. External arrest cylinder 1270 is provided with arrest tab 1272. Flexible arm 1273 of arrest tab 1272 is fastened to external arrest cylinder 1270 via pin 1274. External arrest cylinder 1270 has arrest lid 1407 engaging flange 1276 of intermediate stem segment 1258 to prevent exit of upper stem segment 1262 from intermediate stem segment 1258.

Arrest tab 1272 has the function of disabling the advancement of rod 1258 in case of malfunction or the device during the cardiac compression as it will be explained below. Also, when stem member 1252 is advanced into the chest cavity by downward pressure on handle 1206 arrest tab 1272 will not permit upward displacement of intermediate stem segment 1258 via tooth 1271 engaging circular arrest or flange 1276 of upper portion 1263 of intermediate stem segment 1258 through opening 1285 of external arrest cylinder 1270 as it will be apparent from the description below.

Intermediate stem segment 1258 is of general cylindrical hollow shape. It receives in its upper portion 1263 rod 1262 airtightly slideable in it, while its lower portion 1264 is slideable within hollow lower stem segment 1260. Pneumatic container or bottle 1256 is connected with intermediate stem segment 1258 via conduit 1277. Pneumatic bottle or container 1256, contains compressed air or suitable gas as $CO_2$. Conduit 1277 is in open communication with hollow intermediate stem member 1258 via opening 1299 and is airtightly sealed via sealing membrane 1278. Perforating screw 1279 is housed in recess 1280 of pneumatic container 1256, said perforating screw having thread 1281 mating with corresponding thread 1282 on recess 1280 of pneumatic container 1256, screw tip 1283 being in contact with sealing membrane 1278. Screw 1279 has handle 1284. Screw tip 1283 has holes 1246 to allow passage of air after screw 1279 has penetrated membrane 1278. Pneumatic container or bottle 1256 is housed within housing 1247. Handle 1248 projects outwardly from housing 1247 for easy handling by the operator. Distal end 1286 of intermediate stem segment 1258 is engaged as above mentioned in a slideable fashion within hollow lower stem segment 1260. Expandable member 1254, firmly connected to distal end 1286 of intermediate stem member 1258, comprises inflatable member 1288 and support ribs 1216 preferably, although not necessarily made of resilient material such as steel. All Support ribs 1216 are connected at their respective proximal ends 1225 to distal end 1286 of intermediate stem segment 1258. Inflatable member or balloon 1288 of expandable member 1254 is connected and in flow communication with intermediate stem segment 1258 via opening 1292.

Stem tip or distal end 1261 of stem member 1252 is firmly connected to distal end 1287 of hollow lower stem segment 1260 of stem member 1252 and is of greater width than contiguous lower stem segment 1260. Stem tip 1261 is of general spheroid or ovoid shape or of elliptic cross-section. Stem tip 1261 is composed of two parts: proximal part 1234 shaped as an inverted cup firmly attached as above described to distal end 1287 of lower stem segment 1260 of stem member 1252, and distal part or convex apex 1235 having circular edge 1236 adapted to fit together with circular edge 1237 of circular opening 1238 of proximal part 1234 of stem tip 1261 to form together the above mentioned spheroid shaped stem tip 1261. Convex apex 1235 is firmly attached to base or inferior surface 1291 of inflatable member or balloon 1288 described below. Support ribs 1216 are firmly attached to superior surface 1290 of inflatable member 1288 and approximately equidistantly spaced. Superior surface 1290 of balloon 1288 interconnects therefore continuous ribs 1216 in a web fashion. Balloon 1288 of expandable member 1261 is preferably made of substantially inextensible and airtight material. However balloon 1288 can also be made of stretchable, compliant airtight material. Apex 1235 of stem tip 1261, as above described, is firmly attached to base or inferior surface 1291 of balloon 1288. Inflatable member or balloon 1288 of expandable member 1254 is connected and in flow communication with intermediate stem segment 1258 via opening 1292.

Stem tip or distal end 1261 of stem member 1252 is firmly connected to distal end 1287 of hollow lower stem segment 1260 of stem member 1252 and is of greater width than contiguous lower stem segment 1260. Stem tip 1261 is of general spheroid or ovoid shape or of elliptic cross-section. Stem tip 1261 is composed of two parts: proximal part 1234 shaped as an inverted cup firmly attached as above described to distal end 1287 of lower stem segment 1260 of stem member 1252, and distal part or convex apex 1235 having circular edge 1236 adapted to fit together with circular edge 1237 of circular opening 1238 of proximal part 1234 of stem tip 1261 to form together the above mentioned spheroid shaped stem tip 1261. Convex apex 1235 is firmly attached to base or inferior surface 1291 of inflatable member or balloon 1288 described below. Support ribs 1216 are firmly attached to superior surface 1290 of inflatable member 1288 and approximately equidistantly spaced. Superior surface 1290 of balloon 1288 interconnects therefore continuous ribs 1216 in a web fashion. Balloon 1288 of expandable member 1261 is preferably made of substantially inextensible and airtight material. However balloon 1288 can also be made of stretchable, compliant airtight material. Apex 1235 of stem tip 1261 as above described, is firmly attached to base or inferior surface 1291 of balloon 1288. Base 1291 of balloon 1288 provides in use the contact surface with the heart when expandable member 1254 is expanded.

As shown in FIG. 28, when expandable member 1254 is in a contracted status, balloon 1288 and support ribs 1216 are retained in their entire length within lower stem segment 1260. Support ribs 1216 are forced to bunch together very close one to another against their resiliency which urge them to diverge outwardly one from another in correspondence of their distal segments. Balloon 1288 is contracted or folded within hollow lower stem segment 1262 along with ribs 1216.

Locking means 1401 is fastened to intermediate segment 1258 of stem member 1252 via pin 1402 and provided with resilient arm 1406 having a slant contact surface 1405 for facilitating engagement of flange 1404 of lower stem segment 1260 in recess 1403 of locking means 1401, as it will be apparent from the description below.

In use, as shown in FIG. 28, hollow stem tip 1261 is inserted into the skin preferably in the left parasternal region in a skin area corresponding to the intrathoracic anatomical area designated "sine pleura," after a small skin incision is made to allow entry of distal tip 1261 of stem member 1252 into the subcutaneous tissue.

Stem member 1252 is further advanced through the thickness of chest wall 107 by means for blunt dissection until entry of stem end or tip 1261 is gained into chest cavity 110. Arrest tab 1272 will not allow downward displacement of upper stem member segment or rod 1262 as a result of engagement of tooth 1271 with circular arrest or flange 1276 of intermediate member segment 1258. Being distal end 1261 of stem member 1252 of a greater width than distal contiguous segment 1287 of hollow lower stem segment 1260, distal end or stem tip 1261 of stem member 1252 allows an operator of the device, upon penetration of distal stem end or tip 1261 into the chest cavity 110, to tactily sense entry of the distal stem end or stem tip 1261 into the chest cavity by the sudden fall of resistance to forward and sideways movement of said distal stem end 1261, said resistance to forward and sideways movements being encountered during passage of said stem tip 1261 through chest wall 107. When the operator has ascertained penetration of distal end 1261 of stem member 1252 into chest cavity 110, he or she advances slideable intermediate stem member 1258 relatively to the hollow lower stem segment 1260 by holding still hollow lower stem segment 1260 relatively to the patient with one hand, and acting upon handle 1248 with his or her other hand so as to move intermediate stem segment 1258 downwardly relatively to lower stem segment 1260, toward chest cavity 110. Intermediate stem member 1258 therefore will be advanced to a full advanced position, i.e., until conduit 1277 of container 1256 will engage flange 1404 of proximal end 1296 of lower stem segment 1260. Upon full advancement of intermediate stem member 1258 into lower stem segment 1260, locking means 1401 will lock stem intermediate member 1258 to lower stem segment 1260 via engagement of recess 1403 with flange 1404.

Being distal end 1286 of intermediate stem member 1258 connected to proximal ends 1225 of ribs 1216, the forward movement of intermediate stem member 1258 will result with ejection and exit of ribs 1216 through opening 1238 of proximal part 1234 of stem tip 1261. Upon ejection of distal segments of support ribs 1215 from the stem tip 1261, support ribs 1216 will diverge one from another, due, as already described, to their outward resiliency. Such an outward expansion of ribs 1216 begins with the distal segments of the ribs and proceeds with contiguous segments. The outward resiliency is a critically important feature in placing an expandable member into the chest cavity, because it allows self-expansion of the expandable member very early upon entry of the blunt stem tip 1261 and by such a feature it prevents the need for displacement of the anterior wall of the heart when the expandable member is still contracted, having to advance by its entire antero-posterior length before opening up to expand in order to exit first from the chest wall. Advancement of a contracted expandable member toward the heart until its passage through the chest wall is completed, or almost completed, is dangerous and risky and should be avoided by any device because the heart is in contact with the chest wall and, as a matter of fact, the external lining of the heart, i.e., its pericardium is attached to the inner aspect of the chest wall via sterno-pericardial ligaments. The presence of the sterno-pericardial ligaments adds the requirement of additional pressure to be exerted upon the heart with a contracted expandable member and requires an antero-posterior displacement of the anterior wall of the heart approximately equal to the radius of the heart contacting surface of the expanded expandable member if the ribs are not made outwardly resilient.

The operator will screw in perforating screw 1279 which will perforate, via screw tip 1283, sealing membrane 1278 allowing passage of compressed air or gas from pneumatic container 1256 into inflatable member 1288 via conduit 1277 along hollow intermediate stem segment 1258. Inflatable member 1288 will fully expand, and, by expanding, will provide, via its inferior surface or base 1291, a contact surface to heart 69 for the purpose of direct compression of the heart. Indeed, in order to compress decompress the heart, the operator will press downward on handle 1206 which in turn will displace downward intermediate member 1258 via rod 1262. Fully expanded balloon or inflatable member 1288 will compress heart 69 while ribs 1216 will provide balloon 1288 with lateral and posterior support so as to require a reduced expanding pressure within the inflatable member 1288 allowing a softer contact with the external surface of the heart. In case of accidental perforation of balloon 1288 at any stage of the operation pressure within hollow intermediate stem segment 1258 will drop disabling advancement of rod 1262 no longer upwardly held by compressed air or gas. This is a very important safety feature which can also be applied to all types of embodiments A.

Embodiment VI

Figure 30:
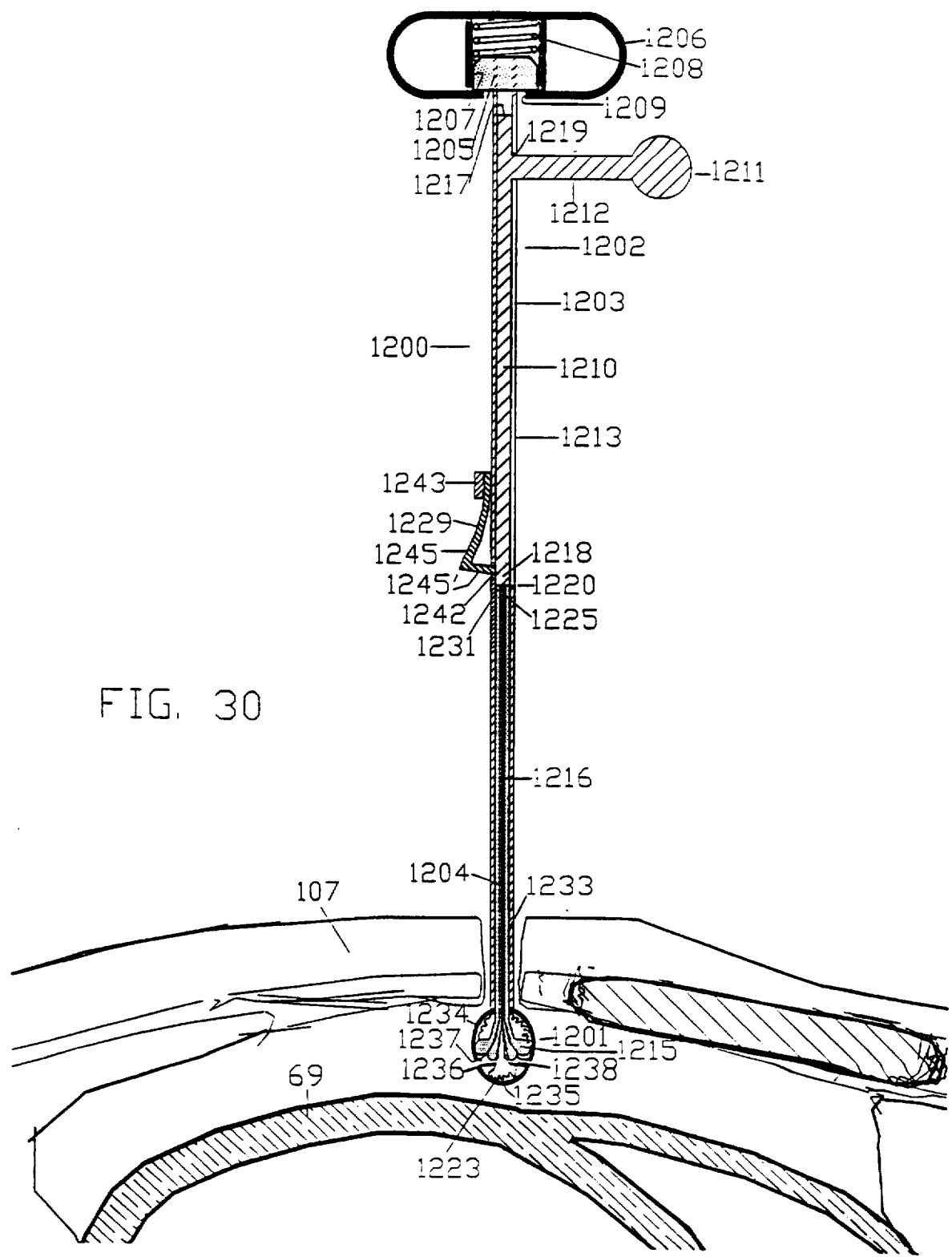
FIG. 30 is a cross-sectional view of an alternative form of the device of FIG. 1.
Figure 31:
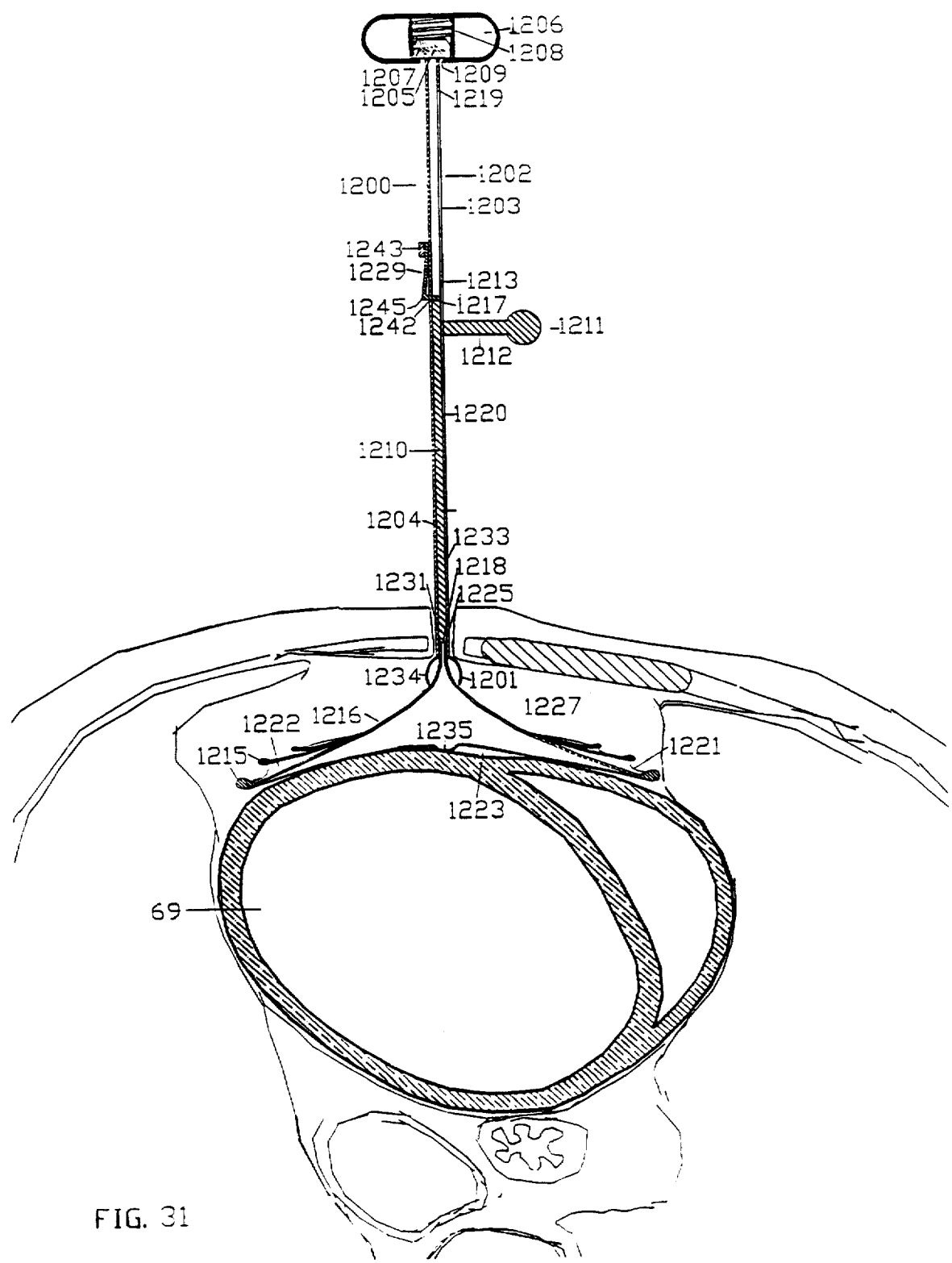
FIG. 31 is a cross-sectional view of the device of FIG. 30 shown after full expansion of the expandable member and at an early stage of compression of the heart.
Figure 32:
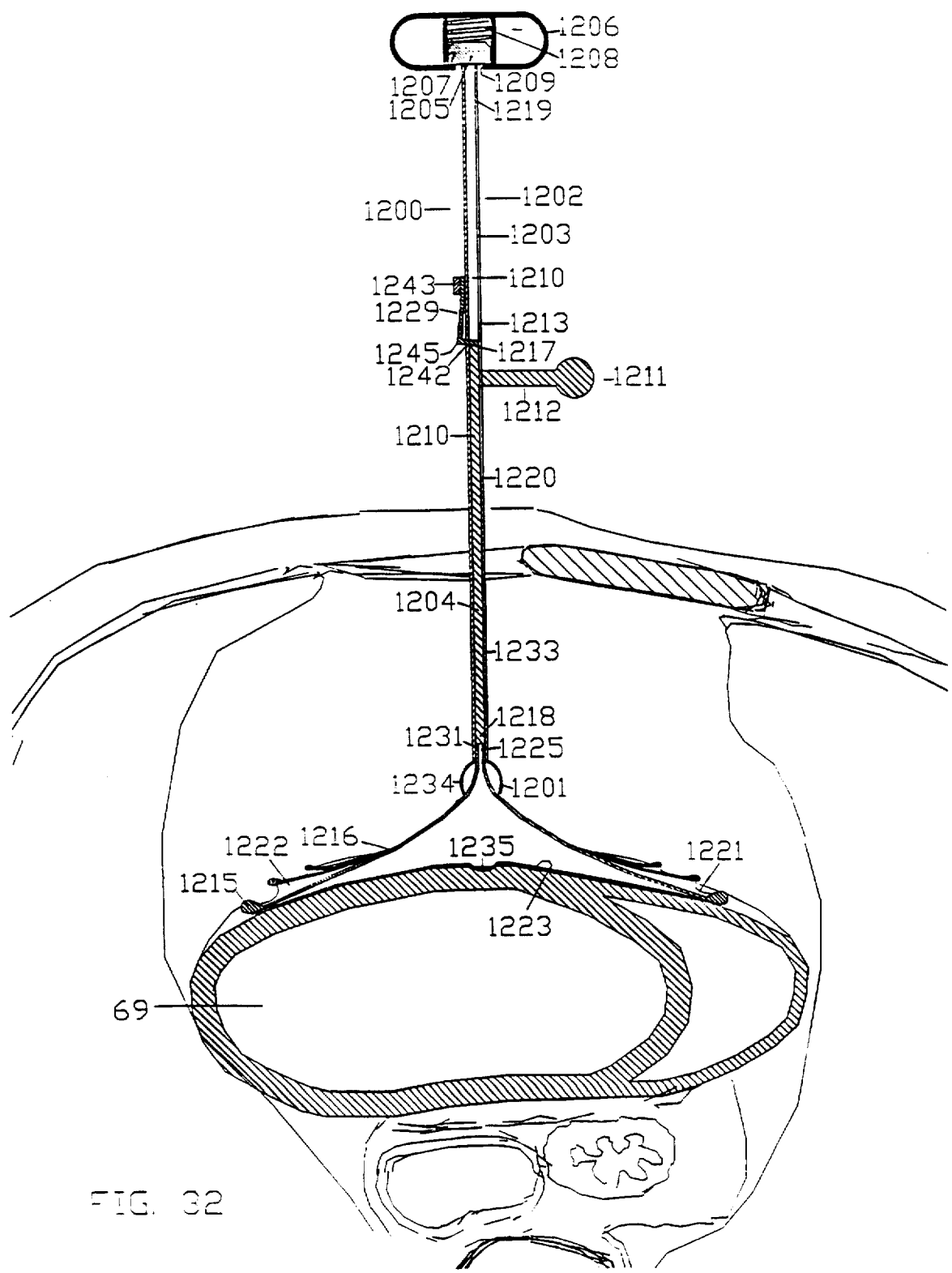
FIG. 32 is a cross-sectional view of the device of FIG. 30 shown after full expansion of the expandable member accomplishing full compression of the heart.

Embodiment VI has numerous similarities and numerous parts which are identical to device 1250 of FIGS. 28 and 29. Reference numbers illustrating the same parts have been therefore maintained. FIGS. 30, 31, and 32, show an embodiment, indicated generally at 1200, of the cardiac pump 1 of FIGS. 1 to 10. The device includes a different type of expandable member carried by the blunt stem tip of a stem member.

As shown in FIG. 30, the device, generally indicated at 1200, is composed of two main components, stem member 1202 and expandable member 1204. Stem member 1202, of general cylindrical shape, comprises hollow stem 1203 having a proximal end 1205 and a distal end or stem tip 1201. Proximal end 1205 of stem member 1202, of general cylindrical shape as hollow stem 1203 but of larger diameter, is mounted in slideable fashion within recess 1207 of handle 1206. Spring or resilient means 1208 urges downward stem member 1202 Circular lid or arrest 1209 in handle 1206 does not permit exit of stem member 1202 from handle 1206. Within hollow stem 1203 is slidably mounted rod 1210. Proximal end 1231 of expandable member 1204 is firmly attached to distal end 1218 of rod 1210 in a folded or contracted status prior to use. Hollow stem 1203 is formed with longitudinal slit 1213 for handle arm 1212 of handle 1211, longitudinal slit 1213 having proximal end 1219 and distal end 1220. Locking means or tab 1245 having flexible arm 1229 is fastened via pin 1243 to hollow stem 1203 with tooth 1245' engaging opening 1242 in hollow stem 1203.

Stem end or tip 1201, firmly attached to distal segment 1233 of hollow stem 1203 of stem member 1202 is of greater width than continuous distal segment 1233. Stem tip 1202 is of general spheroid, elliptical cross-section or ovoid shape. Stem tip 1201 is composed of two parts: proximal cart 1234 shaped as an inverted cup and firmly attached as above described to hollow stem 1203 of stem member 1202, and distal part or convex apex 1235 with circular edge 1236 of apex 1235 adapted to fit together with circular edge 1237 of circular opening 1238 of proximal cup 1234 to form together the above mentioned spheroid shaped stem tip 1201. Convex apex 1235 is firmly attached to base membrane 1223 as it will be apparent from the description below. As for embodiment V of FIG. 28 and 29, expandable member 1204 comprises a body formed with a number of ribs 1216, made of resilient material such as steel. All ribs 1216 are connected at their respective proximal ends 1225 to distal end 1218 of a rod 1210, slideable, as already described, within hollow stem 1203 of stem member 1202. Proximal end 1219 of slit 1213 of hollow stem 1203 arrests upward displacement of rod 1210 via engagement of arm 1212 of handle 1211 with proximal end 1219 of slit 1213. Arrest of rod 1210 prevents that distal ends 1215 of ribs 1216, connected to rod 1210, lose their alignment with stem tip 1201 by moving backward, i.e., proximally in respect to hollow stem 1203.

Contiguous ribs 1216 are interconnected via webs 1222, of grossly triangular shape as seen in FIGS., 31 and 32 and made of fabrics or plastic or other suitable material substantially inextensible. A base sheet or membrane 1223 also made of fabrics or plastic or other suitable substantially inextensible material is attached to distal blunt ends 1215 of ribs 1216 and to distal or outer margin or edge 1221 of webs 1222 to form a base for contact with heart 69 when expandable member 1204 is fully expanded. As shown in FIG. 29, when expandable member 1204 is in a contracted status, all ribs 1216 are retained in their entire length within hollow stem 1202 and forced to bunch together very close one to another, against their resiliency which urges them to diverge outwardly one from another in correspondence of their distal segments.

In use, as shown in FIG. 30, as for all the devices previously described, hollow stem tip 1201 is inserted into the skin preferably in the left parasternal region in a skin area in correspondence of the anatomical area designated "sine pleura," after a small skin incision is made to allow entry of distal tip 1201 of stem member 1202 into the subcutaneous tissue.

Stem member 1202 is further advanced by blunt dissection through the thickness of chest wall 107 until entry is gained into chest cavity 110 by blunt dissection. Being distal end 1201 of hollow stem 1203 of a greater width than distal contiguous segment 1233 of hollow stem 1203 distal end or stem tip 1201 of stem member 1202 allows an operator of the device, upon entry of distal stem end or blunt tip 1201 into the chest cavity 110, to tactily sense entry of the blunt distal stem end 1201 into the chest cavity by the sudden fall of resistance to forward and sideways movement of said distal stem end 1201 said resistance to forward and sideways movements being present during passage of said stem tip 1201 through chest wall 107.

When the operator has ascertained penetration of distal end 1201 of stem member 1202 into chest cavity 110, he or she advances slideable rod 1210 relatively to hollow stem 1203 by holding still, relatively to the patient, with one hand, hollow stem 1203 by its distal segment, and acting upon handle 1211 with his or her other hand so as to move rod 1210 downwardly, toward chest cavity 110. Rod handle 1211 will be advanced to a fully advanced position, i.e., until handle ann 1212 of handle 1211 will engage distal end 1220 of slit 1213 of hollow stem 1203. Being distal end 1213 of rod 1210 connected to proximal ends 1225 of ribs 1216, the downward movement or rod 1210 will result with election end exit of ribs 1216 through opening 1238 of proximal part, or cup, of stem tip 1201. Upon ejection of distal segments 1215 of ribs 1216 from stem tip 1201 ribs 1216 will diverge outwardly one from another due, as alrcady described, as a result of their resiliency. Webs 1222, of fabrics or plastic or other suitable material, will retain ribs 1216 from diverging beyond a desired decree of divergence. Ribs 1216 and webs 1222, upon full expansion, will form a bell-shaped member with base sheet 1223 facing heart 69, and top surface 1227 facing stem 1203. Base membrane 1223, being attached to distal ends 1215 of ribs 1216 and to distal webs margins 1221 of webs 1222, form a substantially inextensible base for contact with heart 69 when expandable member 1204 is fully expanded. Releasable locking means 1245 will lock rod 1210 via entry of tooth 1245' into opening 1242 of stem member 1202 in a fully advanced position by engaging proximal end 1217 of slideable rod 1210, for the time of compression and decompression of the heart. The operator as shown in FIG. 30 will compress and decompress hearth 69 by pressing on handle 1206. Contraction of spring or resilient means 1208 will prevent injuries to the heart if excessive pressure is applied after compression of the heart against the thoracic spine. When the resuscitation operation has been completed the operator will unlock rod 1210 via disengaging tooth 1245' from proximal end 1217 of rod 1210. He or she then will retract rod 1210 by pulling up handle 1211. Expandable member 1204 will contract and will fold within hollow stem 1203 permitting so the extraction of stem tip 1201 and the penetrated segment of stem 1203 from chest cavity 110.

Embodiment VII

FIGS. 33 and 34 show vet an alternative form of device 1 of FIGS. 1 to 10. FIG. 33 is a cross-sectional view of the device generally indicated at 1300. Device 1300 is composed of two main components stem member 1302 and expandable member 1304. Stem member 1302 is composed of proximal end 1303, shaft 1305 and stem end 1306. Stem shaft 1305 is composed of three concentric cylindrical stems, outer 1308, intermediate 1309 and inner 1310. Stem member 1302 is provided proximally with handle 1206 in all similar to the two previously described device 1200 and 1250. Within handle 1206 recess 1207 of handle 1206 is slidably mounted proximal end 1205 of upper stem member segment 1310. Proximal end 1205 of upper stem segment 1310 is of general cylindrical shape as upper segment of stem member 1302 but of larger diameter. Spring or resilient means 1208 urges downward stem member 1302. Circular lid or arrest 1209 in handle 1206 does not permit the exit of stem member 1302 from handle 1206 via engaging proximal end 1205 of tipper stem member segment 1307.

Outer stem 1308 and intermediate stem 1309 of shaft 1305 of stem member 1302 arc hollow while iruer stem 1310 can be either solid or hollow. Handle wheels 1313, 1314, 1315, are respectively connected to each of the three cylindrical stems, outer 1308, intermediate 1309, and inner 1310. Each handle wheel 1313, 1314, 1315, is formed with respective seating 1316, 1317, 1318, for locking means or pin 1319. While seating 1318 of inner stem 1310 is visible in FIG. 33, seating 1316 and 1317 cannot be visualized because not aligned with seating 1318 with the device at rest prior to expansion of expandable member 1304 as it can be better understood from the description below. Locking means 1319 composed of pin 1320 and arm or handle 1321 engaged within seating 1318.

Expandable member 1304 is composed of three or more identical bluntly tipped rods 1330, 1331, 1332, connected by membrane 1343, as seen in FIG. 34. Blunt rods 1330, 1331, 1332, are firmly attached to, or in continuity respectively with stem ends 1330' 1331' 1332' of outer stem 1308, intermediate stem 1309 and inner stem 1310, being positioned at an angle preferably obtuse, in order to facilitate the insertion of expandable member 1304 into chest cavity 110 by the operator as it will be apparent from the description of the operation. Rods 1330, 1331, 1332, remain superimposedly overlapped until expansion of the expandable member is actuated by the operator. Rods 1330, 1331, 1332, have blunt ends 1342 for the purpose of blunt dissection of the chest wall and for avoiding injuries to the intrathoracic organs upon chest cavity penetration. In order to facilitate penetration by blunt dissection through the chest wall, rods 1330, 1331, and 1332, may be curved outwardly in continuity with the stem, with convexity facing the chest cavity so as to enter the chest cavity almost parallel to the anterior wall of the heart.

In operation, as shown in FIG. 30, the operator after making a superficial incision in the skin as for all the devices previously described, in the left parasternal region in a skin area in correspondence of the anatomical area designated "sine pleura," the operator inserts blunt ends 1342 of rods 1330, 1331, 1332, of expandable member 1304 into the subcutaneous tissue and advances them by means of blunt dissection through to the thickness of the chest wall. Blunt dissection of the chest wall will be carried out with rods 1330, 1331, and 1332, with an approach nearly perpendicular to the anterior chest wall until occurred blunt penetration of blunt ends 1342 of rods 1330, 1331, 1332, into the chest cavity occurs. During penetration through the chest wall, stem member 1302 will therefore be tilted from its initial perpendicular position relatively to the anterior chest wall. As soon as the operator senses the occurred penetration into the chest cavity by blunts ends 1342, he or she will gradually reposition stem member 1302 to reach a right angle in respect to the anterior chest wall while gradually advancing blunted tips of rods 1330, 1331, and 1332, inside the chest cavity along a plane which is substantially parallel to the anterior wall of the heart and is in close proximity of the inner aspect of the anterior chest wall. Once rods 1330, 1331, and 1332, are fully entered into the chest cavity and consequently stem member 1302 is repositioned approximately perpendicularly in respect to the anterior chest wall, the operator will rotate sequentially handle wheels 1313, 1314, 1315, in order to space distal ends of rods 1330, 1331, and 1332, and fully expand expandable member 1304 as shown in FIG. 34 which is a view from below of the fully expanded expandable member. Indeed rods 1330, 1331, 1332, being sideways rotated will distend connecting membrane 1343. Locking means 1319 will be inserted in corresponding aligned seating 1316, 1317, 1318, locking respective rods 1330, 1331, 1332, in a fully outwardly expanded position by locking wheels 1313, 1314, and 1315, all together. As for the device previously described, compression of the heart will be accomplished by downward pressure on handle 1206. Membrane 1343, fully distended by spread rods 1330, 1331, 1332, will provide an adequate contact surface area for the purpose of compressing the heart.

The device will be easily removed by extracting pin 1320 from seatings 1315, 1316, and 1317, and by rotating rods 1330, 1331, 1332, to their original position, by acting upon wheels 1313, 1314, 1315, so as to contract expandable member 1343 and allow its extraction from chest cavity 107.

All the disclosed expandable member may have a number of different shapes, and the heart compressing surface of the expandable member may also have a number of shapes to adapt to the surface of the heart, including a concave shape, flat, convex and can also be deformable for such adaptation to the heart.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

TYPE A EMBODIMENTS

FIGS. 18 to 25 illustrate a group of devices which, while retaining the same mechanisms of gaining entry into the chest cavity in front of the heart, differ in the way of compressing and decompressing the arrested heart. All the devices of type B share with the previously described devices of type A, a most important feature: safe entry of a stem provided with a blunt tip carrying an expandable member into the thoracic cavity. By entering the chest cavity with a blunt tip, following gradual and controlled advancement of such a blunt tip through the chest wall, with largely automatized provisions for the instantaneous arrest of advancement immediately upon entry into chest cavity by the blunt tip the underlying intrathoracic structures are exposed to no risk of injuries deriving from the insertion of the expandable member into the chest cavity. To the contrary, entry into the thoracic cavity with any pointed, sharp tipped device carries the potential and the probability, regardless of any precautionary measures, for resulting in high incidence of major and fatal injuries to the underlying structure, above all the heart, including coronary arteries and myocardium, defeating so the purpose of successful resuscitation.

Device 1002 of FIGS. 18 to 21 is an alternative form of device 1 represented in FIGS. 1 to 10. Device 1002 retains the same safety mechanisms of gaining entry into the chest cavity in front of the heart as device 1 of FIG. 1 to 10, including the blunt penetrating tip, while it differs in the way of compressing and decompressing the arrested heart.

Device 1002 is basically similar to device 1 of FIGS. 1 to 10 with few structural differences. The corresponding parts have retained the same numbers.

Figure 18:
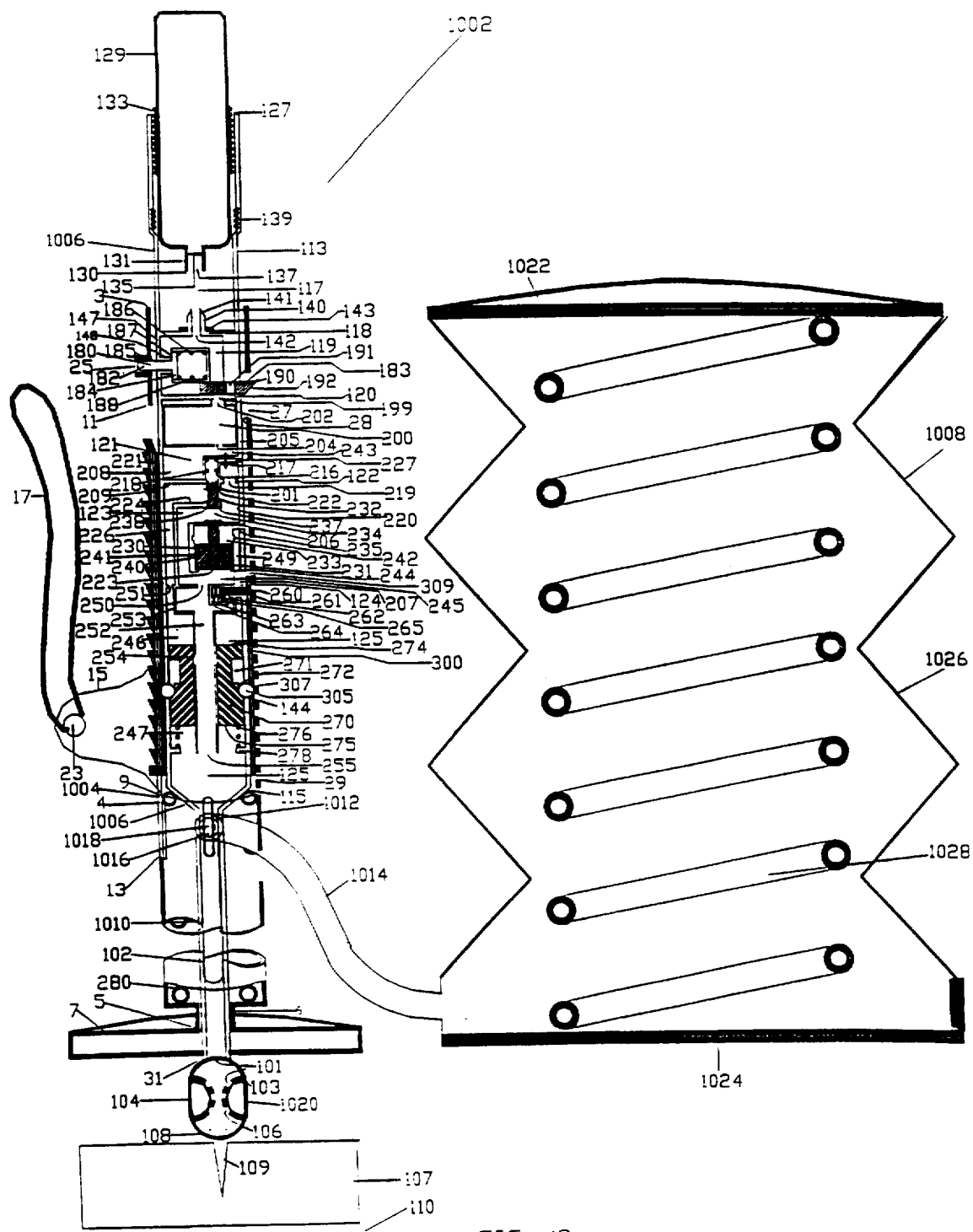
FIG. 18 shows a vertical section of an alternative form of the device as it is prior to use.
Figure 19:
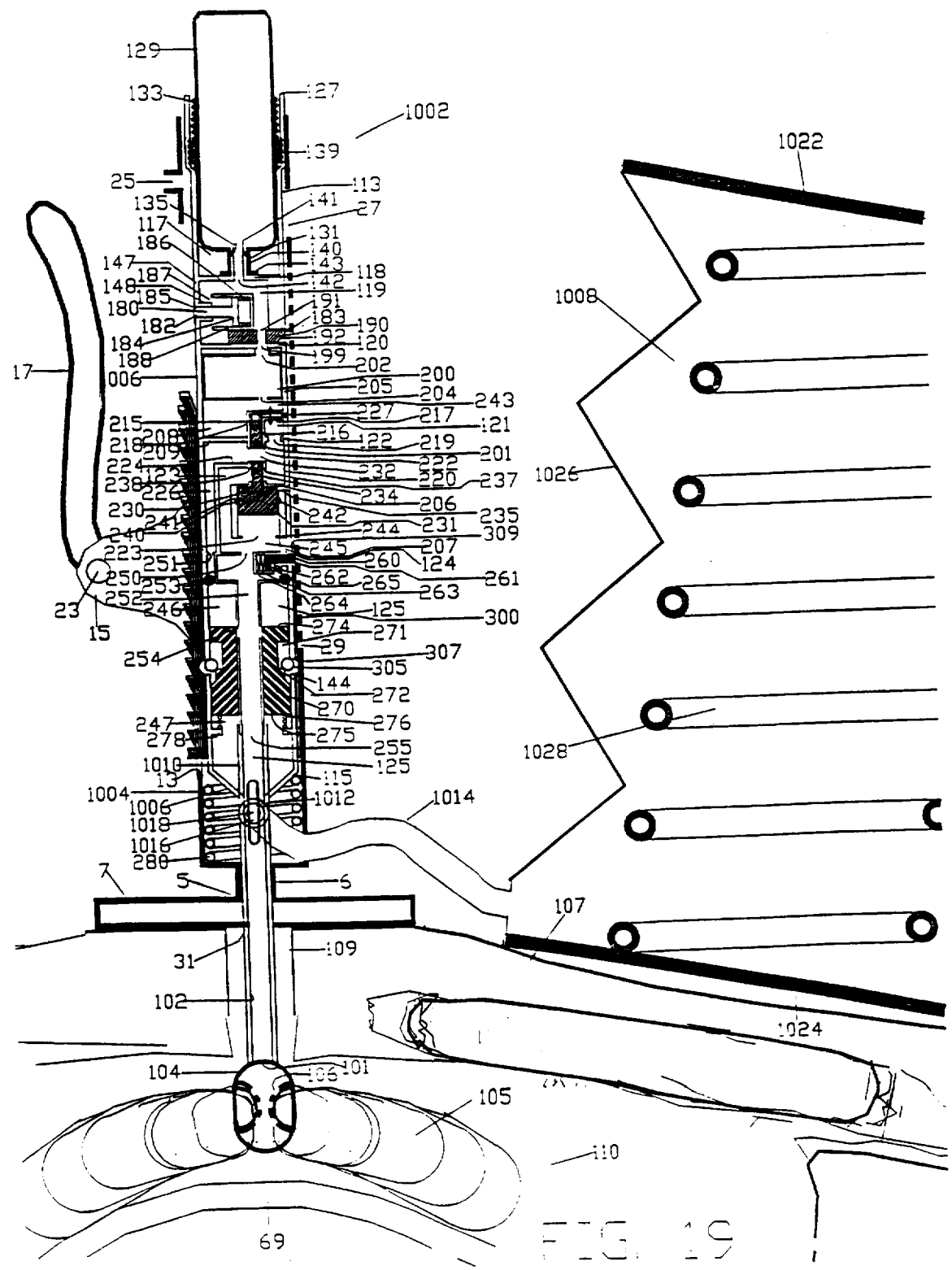
FIG. 19 is a vertical section of device of FIG. 18 showing the stem tip of the cardiac pump of FIG. 18 at the instant it enters the patient's chest cavity.

Device 1002, as shown in FIGS. 18 and 19, is composed of four main components: support member generally indicated at 1004, stem member or stem unit generally indicated at 1006, an intermediate member generally indicated at 300, and an inflating-deflating means or device generally indicated at 1008.

The support member 1004 is the same as support member 2 except that, as better shown in FIGS. 18 and 19, it has, at its surface, on its distal segment 5, slit 1010, in order to permit the insertion of distal end 1012 of hose 1014 of inflating-deflating device 1008 on window 1016 of stem 102 of stem unit 1006.

Stem member or unit member 1006 is basically similar to stem or unit member 100 of FIGS. 1 to 10 with few important differences.

Handle 111 of FIG. 1 with T bar 145 is no longer present.

Shut-off valve 210 (better) illustrated in FIG. 3 and 4, is no longer present.

Opening 197, shown in FIG. 4 in diaphragm 120 and opening 209 (FIG. 4) in diaphragm 122 are no longer present.

As shown in FIGS. 18 and 19, stem 102 is connected to hose 1004 of inflating-deflating means 1008. Three ways shut off valve 1018 is located at the connection between distal end 1012 of hose 1014 and stem 1002.

Expandable member or balloon 1020, contained in position of rest within circular groove 103 of stem end 104 as for the device of FIG. 1 to 17 is of larger size when fully expanded than balloon 105. Intermediate member 300 is identical to intermediate member 300 of device of FIGS. 1 to 10, thereof same numbers have been used for same parts.

Inflating-deflating means or device 1008 is generally cylindrical in shape with top wall 1022 bottom wall 1024 and lateral pleated walls 1026. Resilient member or spring 1028 is contained within device 1008 to maintain its lateral wall 1026 distended in its resting position.

It is obvious that manually operated inflating-deflating device 1008 may be substituted by a power operated inflating-deflating device.

Description of the Operation of Embodiment I

The device is placed on the anterior chest in the same way as the correspondent device of FIGS. 1 to 10, and the following operations are exactly the same as the ones described for the previous device of FIGS. 1 to 10, with few important functional differences.

Figure 20:
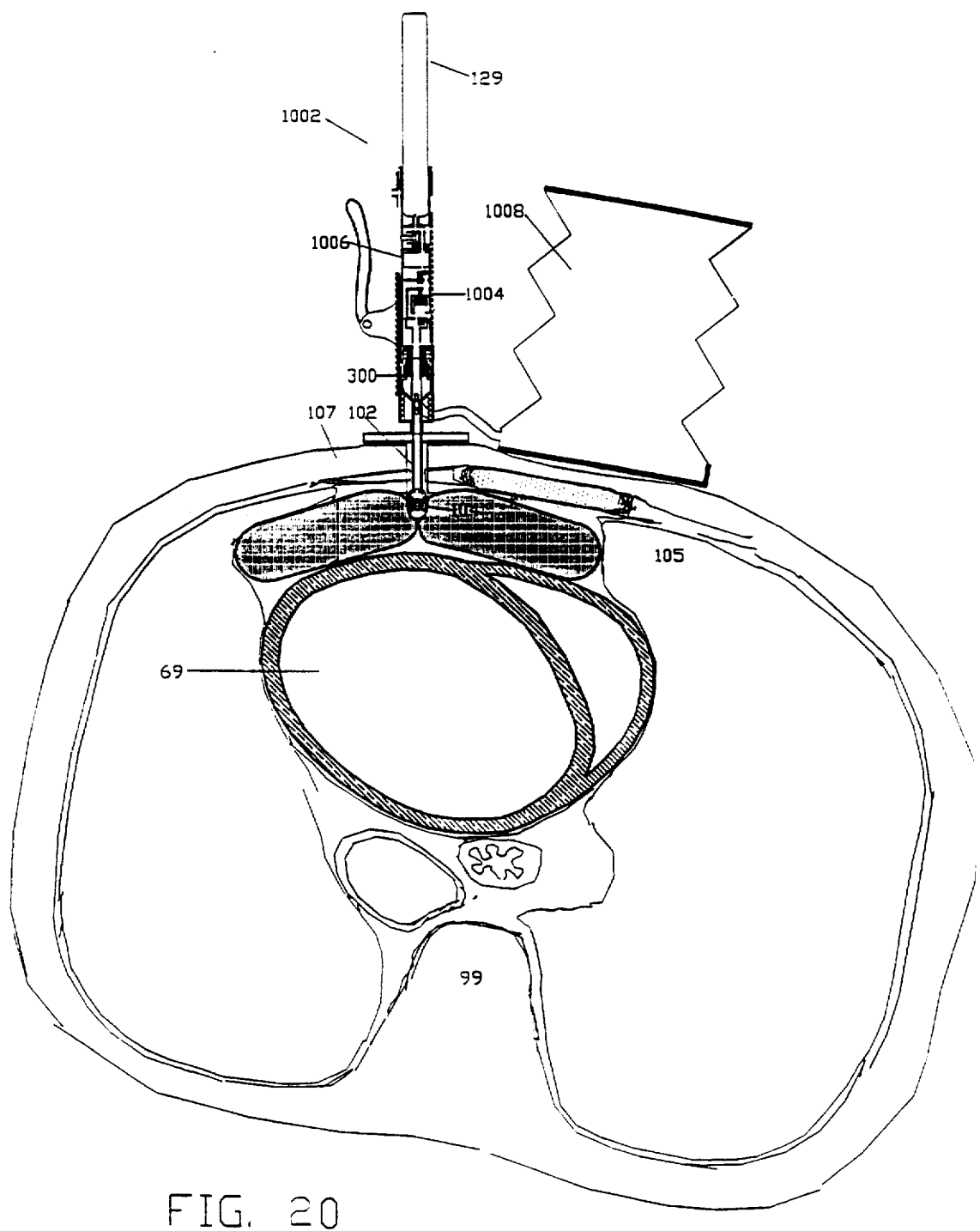
FIG. 20 is a view similar to that of FIG. 19 with the expandable member of the device within the chest cavity after the initial inflation at completion of preparation stages prior to the actual pumping of the heart.

After chest wall penetration and complete passage of blunt stem end 104 through chest wall 107, balloon 1020 will automatically inflate via the same mechanism described for device of FIGS. 1 to 10, as shown in FIGS. 19 and 20.

During advancement of stem 102 through chest wall, distal end 1012 of hose 1014, connected to stem 102, will be able to slide within slit 1010 of support member 1004.

As in correspondent device of FIGS. 1 to 10, lever 17 and intermediate member 300 will automatically disengage from stem unit 1006 upon penetration of blunt stem end 104 into chest cavity, signaling to the operator, by said disengagement, that penetration has occurred into the chest cavity.

The disengagement of the stem member 1006 from intermediate member 300 results in a sudden upward displacement of stem unit 1006 in respect to support case 1004 due to the action of spring 280. Said upward displacement of stem unit 1006 is however minimal, being limited by engagement of pin 261 into the most distally located hole 29 formed in the side wall of support case 1004. Pin 261 is allowed to engage to hole 29 because is no longer retained in its retracted position by side wall of intermediate member 300, which, contrary to stem unit 1006, is prevented from sliding upward in respect to support case 1004 by dog 21 of lever 17 that is anchored to support case 1004. Pin 261 therefore blocks the advancement of blunt stem end 104 with its balloon 1020 in respect to support case 1004 to a distance automatically determined by the device and selected for that specific chest wall thickness that stem 102 of stem unit 1004 penetrates at that particular time.

This automatic arrest of blunt stem end 104 of stem 102 of stem member or unit 1006 is an important safety feature required to prevent that inadverted advancement of stem tip 104 with deflated balloon 1020 might result in damage to the heart, despite bluntness of stem end 104. In device of FIGS. 1 to 10 the locking of stem unit 100 to support case 2 by pin 261 is released by the act of opening the shut of T-valve 180 and consequent entering of high pressure gas into the system with resulting full inflation of balloon 105 and sufficient pressure upon the head 262 of pin 261 to withdraw pin 261 from engagement into hole 29 of support case 2, to allow advancement and then withdrawal of stem unit 100 in respect to support case 2 to effect pumping of the heart. On the contrary, in device of FIGS. 18 to 21, pin 261 is required to remain engaged to hole 29 of support case 1004 to keep stem unit 1006 locked to support case 1004, consequently no high pressure gas will enter the system so that pin 261 is not withdrawn and disengaged from support case 1004.

After automatic disengagement of lever 17 and intermediate member 300 from stem unit 1006, and automatic locking of stem unit 1006 to support case 1004, the operator, made aware of the occurred penetration into chest cavity, will act on three ways shut off valve 1018, opening the passage between hose 1014 and stem 102 and closing passage between stem 102 and chamber 125.

At this point, the operator is ready to perform the cardiac compressiondecompression. The operator, by pressing upon top wall 1022 of inflating-deflating device 1008, inflates balloon 1020, as shown in FIG. 21.

Figure 21:
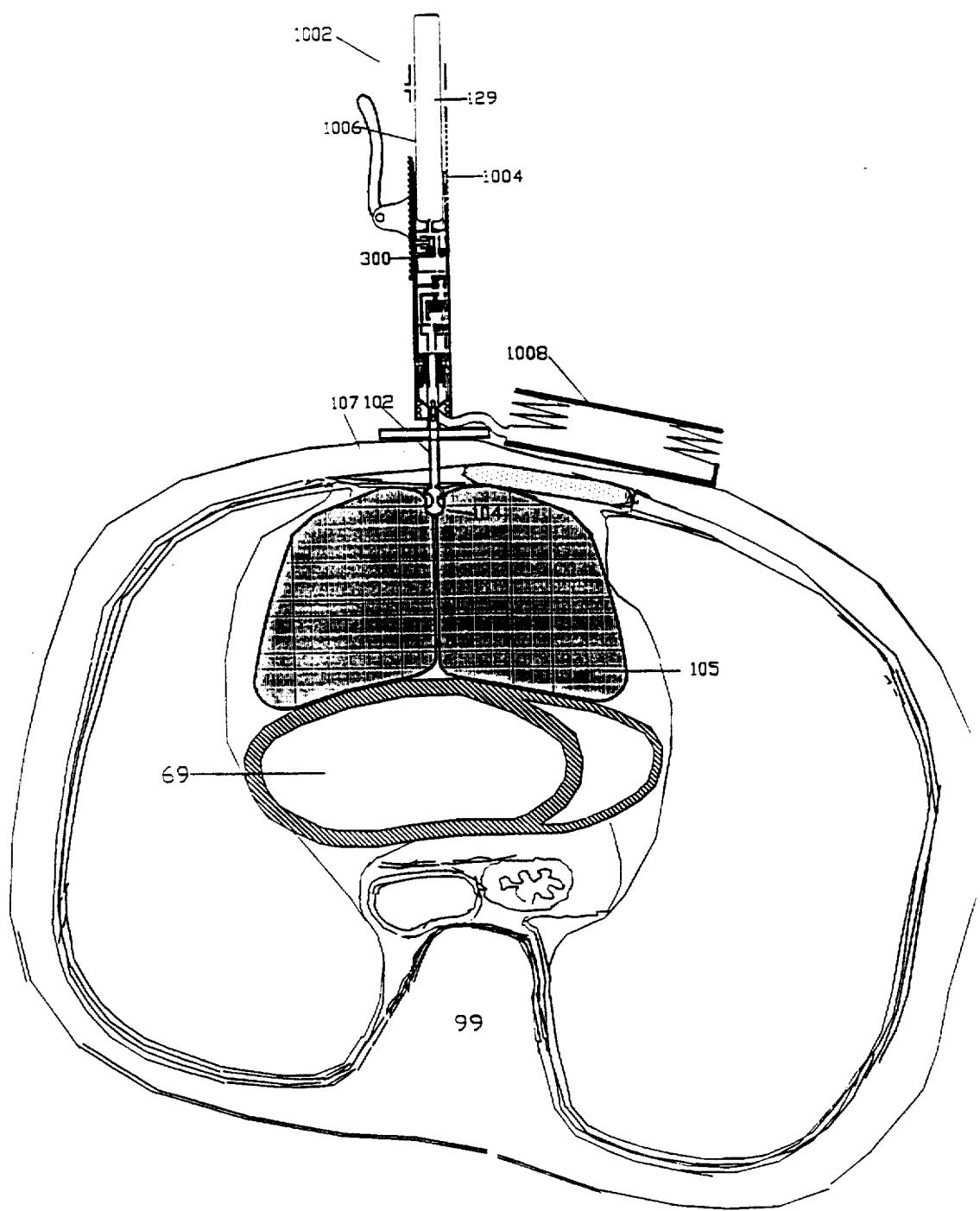
FIG. 21 shows the device of FIG. 18 with the expandable member fully inflated and the heart consequently fully compressed against the vertebral column.

Inflation of balloon 1020 will result in its expansion and compression of the heart between the thoracic spine and the balloon 1020 itself, as shown in FIG. 21.

By releasing pressure upon top wall 1022 of inflating-deflating device 1008, the operator will deflate balloon 1020. Deflation of balloon 1020 will result in its contraction and, consequently, in the decompression of the heart.

By alternatively pressing upon inflating-deflating device 1008 and releasing such pressure, the operator will alternatively compress and decompress the heart.

Being stem tip 104 indirectly locked to support member 1006 as a consequence of actuation of pin 261, as described above, upon entry of stem tip 104 into the chest cavity while stem tip 104 is still adjacent to the inner surface of chest wall 107, and being support case 1006 impeded to advance toward the chest cavity by its base 7, stem tip 104 is prevented to advance toward the chest cavity and, at the same time, after the initial expansion of expandable member 1020, is prevented as well to withdraw from the chest cavity by the expandable member expanded within the chest cavity. Stem tip 104 remains, consequently, firmly anchored to its position in contact with inner surface of chest wall 107.

With the predicament that no definite type of expandable member, with regard to its geometric and physical properties, is to be considered critical, or even significant or relevant for the successful implementation of cardiac massage with any of the devices described as type B in this disclosure, except for its property of being expandable so to be passed through the chest wall while still in a contracted state into the chest cavity where it can be expanded, a description is made below of a sample of possible expandable member, as represented in FIGS. 20 and 21, with the assertion that by no means the expandable member described below is to be considered as the only embodiment conceived in this disclosure. Other embodiments have been considered, differing from the one described below by shape, by site of attachment to the stem tip, by progression of expansion and by other properties. Being expandable member 1020 secured to stem tip 104, and, as just stated above, being stem tip 104 firmly anchored to its position in contact with inner surface of chest wall 107, expansion of said expandable member 1020 as it is represented in FIGS. 20 and 21 and exclusively for the purpose of illustration, will rather occur anteriorly in direction of the chest cavity and will not occur posteriorly toward chest wall 107. Also, anterior expansion of the expandable member 1020 will not occur, in this particular embodiment, in correspondence of its center where expandable member 1020 is attached to blunt stem tip 104, with resulting anterior umbilication of the expanded member in correspondence of blunt stem tip 104. This umbilication of the expanded expandable member 1020 in correspondence of blunt stem tip 104 prevents blunt stem tip 104 from ever coming to contact with the heart during the compression-decompression cycle, safeguarding the heart from possible occurrence of blunt injuries. Umbilication of the expandable member both in systolic and diastolic phase also tends to shape the anterior surface of the expandable member 1020 to a configuration generally and approximately resembling a cup with the periphery of expandable member 1020 more protruded toward the chest cavity than its central area. By such a configuration, expandable member 1020, when adjacent to the heart, will embraces it, and, by being secured to stem tip 104, which in turn is firmly anchored to the inner aspect of the chest wall in a designated area adjacent to the heart where the pleura is absent, it will be able to guide the heart by directing it, during the phase of compression, toward the thoracic spine.

Embodiment II

Figure 22:
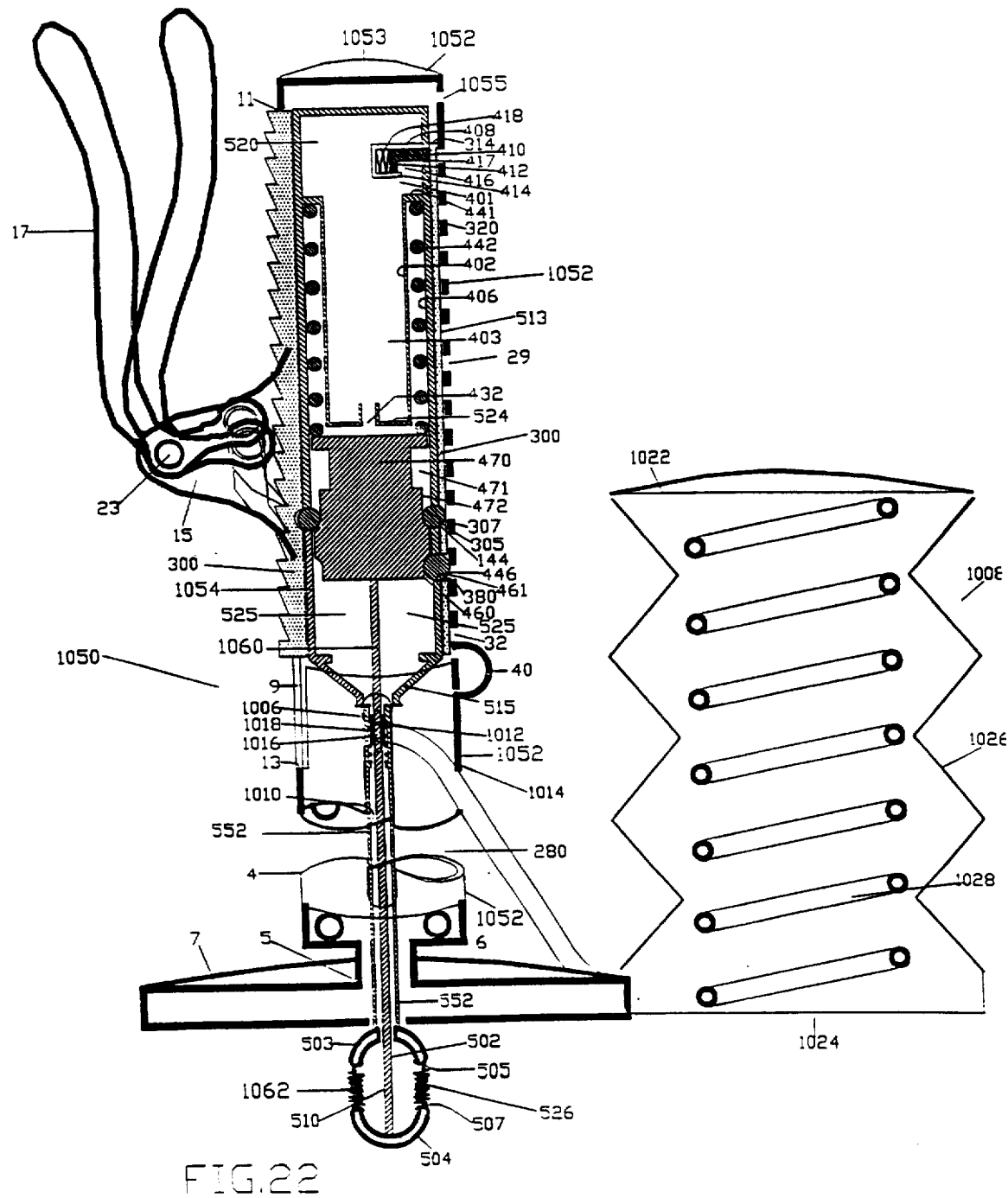
FIG. 22 is a vertical section through an alternative form of the device of FIG. 18 as it is prior to use.
Figure 23:
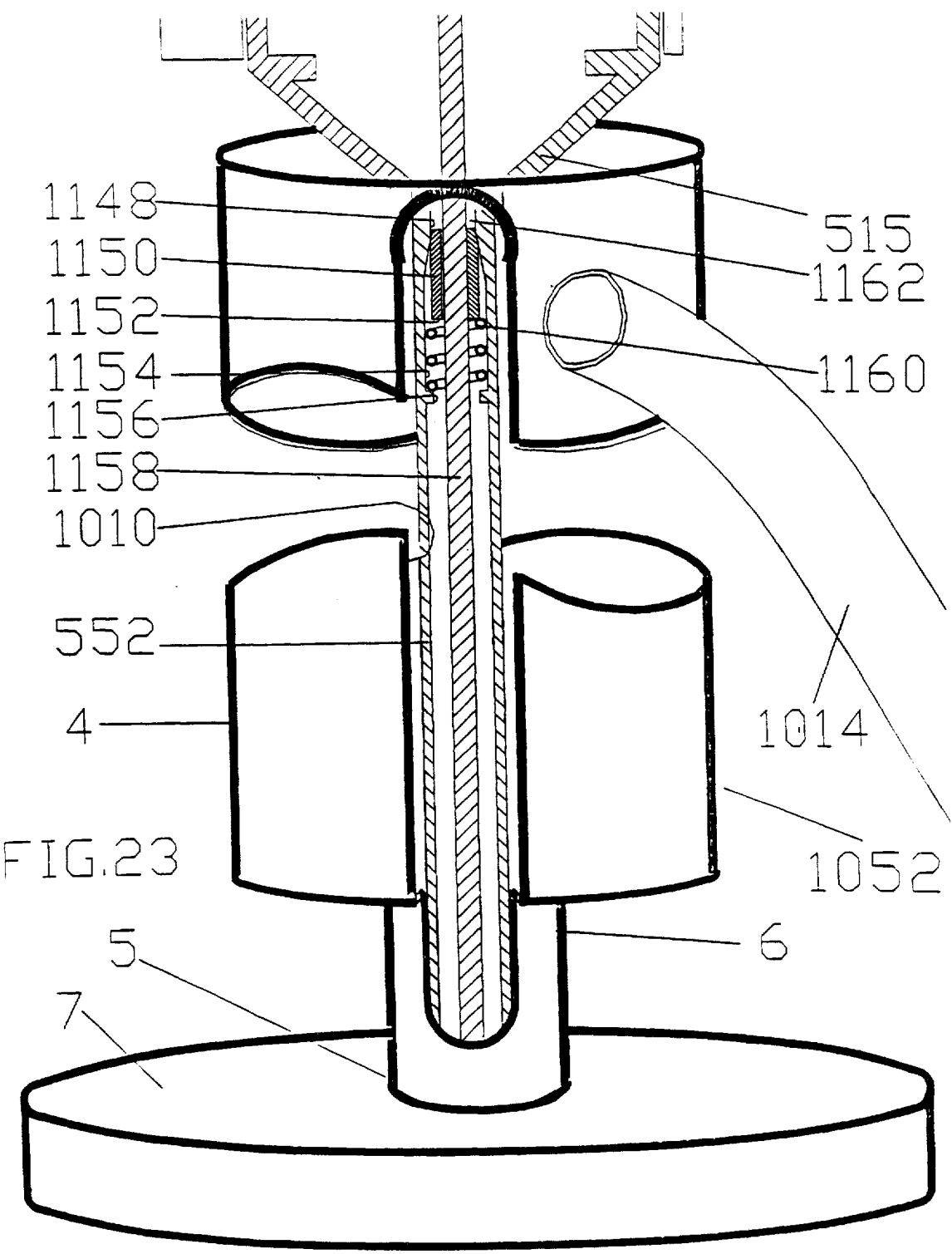
FIG. 23 is a vertical section of the lower segment of the body of the device shown in FIG. 18.

FIGS. 22 and 23 show an alternative form, generally indicated at 1050, of device 500 illustrated in FIG. 11.

Device 1050 retains the same safety mechanisms of gaining entry into the chest cavity in front of the heart as device 500 of FIG. 11, including the blunt penetrating tip, while it differs in the way of compressing and decompressing the arrested heart.

Structure of device 1050 is therefore similar to device 500, except for the following differences. Corresponding parts have maintained the same numbering.

Device 1050, as shown in FIG. 22, is composed of four main components: support member generally indicated at 1052, stem member or unit generally indicated at 1054, an intermediate member generally indicated at 300, and an inflating-deflating means or device generally indicated at 1008.

The support member 1052 is the same as support member 2 of FIG. 11 except that, as shown in FIG. 22, it is closed by top wall 1053. It also has, at its surface, on its distal segment 5, slit 1010, in order to permit the insertion of distal end 1012 of hose 1014 of inflating-deflating device 1008 on window 1016 of outer stem 552 of stem member 1054 as it will be described below.

Stem member or unit member 1054 is structurally similar to stem member 501 of FIG. 11, but devoid of many of its components.

In particular gas-fluids container 129 with its handle 111, the entire chamber 517 with its side walls and all its content, diaphragm 518, chamber 519 with its side walls and all its content, including pin 180 are no longer present.

Central opening 400 in diaphragm 518 is no longer present.

Chamber 521 is devoid of pipe 430 and inner stem 502.

Opening 432 in diaphragm 524 is preserved.

Inner stem 502 which was slidably mounted within piston 470 of FIG. 11 is no longer present and is replaced by solid rod 1060.

Outer stem 552 is connected to hose 1014 of inflating-deflating means 1008 at window 1016. Three ways shut off valve 1018 is located at the connection between hose end 1012 of hose 1014 and outer stem 552.

As shown in FIG. 23, in a segment of outer stem 552 proximal to insertion of hose 1014, a cylinder 1012 is slidably mounted within outer stem 552 and around rod 1060, said cylinder having a cone shaped proximal end 1162 and a distal end 1152 for the seating of compression spring 1160 acting from flange 1156.

Expandable member or balloon 1062, contained in position of rest between convex tip base 503 and convex apex 507 of stem end or tip 526 as for the device of FIG. 11 is of larger size when fully expanded than balloon 506.

Intermediate member 300 is identical to intermediate member of device of FIG. 11, thereof same numbers have been used for same parts.

Inflating-deflating means or device 1008 with connected hose 1014 and shut offvalve 1018 it is the same device of FIGS. 18 to 21 and same numbering has been maintained.

Description of the Operation of Embodiment II

Device 1050 is placed on the chest in the same way as the previous device, and the following steps are exactly the same as the ones described for the previous device 500 of FIG. 11, with few important functional differences.

After chest wall penetration and complete passage of blunt stem end or tip 526 through chest wall 107, lever 17 is felt by the operator to disengage from stem unit 1054 and no further advancement of stem tip 526 will occur within the chest cavity. The operator will act on three ways shut off valve 1018 opening the passage between hose 1014 and outer stem 552 and closing passage between outer stem 552 and chamber 525. Cylinder 1150, located proximally to insertion of hose 1014 to outer stem 552, will prevent retrograde pathway of gas or fluid contained within device 1008, so that the content of device 1008 can flow to and from expandable member 1062. At this point, the operator is ready to perform the cardiac compression-decompression. The operator, by pressing upon top wall 1022 of inflating-deflating device 1008 inflates balloon 1062, as shown for the device 1002 in FIG. 21.

Inflation of balloon 1062 will result in its expansion and compression of the heart between the thoracic spine and the balloon 1062 itself, as shown for the device 1002 in FIG. 21.

By releasing pressure upon top wall 1022 of inflating-deflating device 1008, the operator will deflate balloon 1062. Deflation of balloon 1062 will result in its contraction and, consequently, in the decompression of the heart, as shown for device 1002 in FIG. 20.

By alternatively pressing upon inflating-dellating device 1062 and releasing such pressure, the operator will alternatively compress and decompress the heart.

Embodiment III

Figure 24:
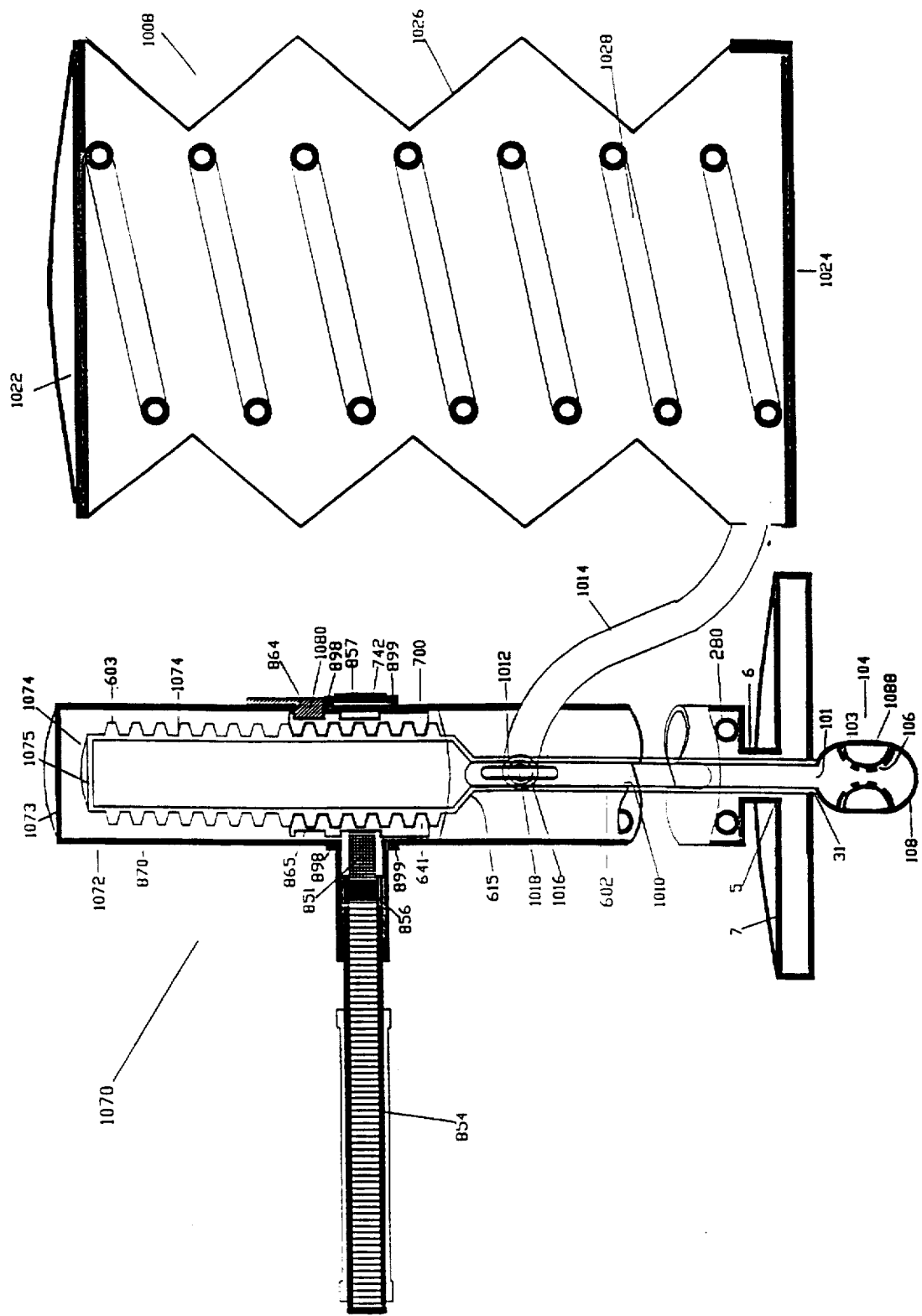
FIG. 24 is a vertical section of yet an alternative form of the device of FIG. 18 shown as it is prior to use.

FIG. 24 shows an alternative form, generally indicated at 1070, of device 600 illustrated in FIG. 12.

Device 1070 retains the same safety mechanisms of gaining entry into the chest cavity in front of the heart as device 600 of FIG. 12, including the blunt penetrating tip, while it differs in the way of compressing and decompressing the arrested heart.

Structure of device 1070 is therefore similar to device 600, except for the following differences.

Corresponding parts have maintained the same numbering.

Device 1070, as shown in FIG. 24, is composed of four main components: support member generally indicated at 1072, stem member or unit generally indicated at 1074, an intermediate member generally indicated at 700 and an inflating-deflating means or device generally indicated at 1008.

The support member 1072 is the same as support member or case 800 of device 600 of FIG. 12, except that, as shown in FIG. 24, it is closed at its top by top wall 1073. It also has, at its surface, on its distal portion slit 1076, in order to permit the insertion of distal end 1012 of hose 1014 of inflating-deflating device 1008 on window 1016 of stem 602 of stem unit or member 1074. Pin 1020 substitutes pin 860 of FIG. 12. It is composed of head 1082 and arm 1084.

Pin 1080 substitutes pin 860 of device 600 of FIG. 12. Pin 1080 is secured to support case 1072 through opening 864 to engage in annular recess 865 of intermediate member 700. Arm 862 of pin 860 described in FIG. 12 for manual displacement is no longer present.

Stem member or unit 1074 is structurally similar to stem or unit member 601 of FIG. 12, but devoid of some of its components.

In particular gas-fluids container 129 with its handle 111, the entire chamber 617 with its side walls and all its content, opening 142 in diaphragm 618, and pin 605 in chamber 621 are no longer present.

Stem member 1074 is closed at its proximal end by top wall 1075.

As for the device 1002 described in FIGS. 18 to 21 and device 1050 described in FIGS. 22 and 23, distal portion 1012 of hose 1014 of inflating-deflating means 1008 is connected to correspondent stem 602 at window 1016. Three ways shut off valve 1018 located at connection between distal portion 1012 of hose 1014 and stem 602 is the same structurally and functionally to the one described for the devices 1002 of FIGS. 18 to 21.

Expandable member or balloon 1088, contained in position of rest within circular groove 103 of stem end 102 is, when expanded, of larger size than balloon 105 of device 600 of FIG. 12. Intermediate member 700 is identical to intermediate member 700 of device of FIG. 12, thereof same numbers have been used for same parts.

Inflating-deflating means or device 1008 is the same one structurally and functionally described for devices 1002 and 1050 respectively of FIG. 18 and FIG. 22.

Description of the Operation of Embodiment III

Device 1070 is placed on the chest in the same way as device 600, and the following operations are exactly the same as the operations described for device 600 of FIG. 12, with few important functional differences.

After chest wall penetration and complete passage of stem end or tip 108 through chest wall 107, the operator will tactually sense a sudden looseness of the device engaged in the chest wall, due to the side clearance of the stem 602 in respect to the surrounding chest wall tissue just penetrated by stem end 108 of much larger diameter than stem 602, as already described for device 600 of FIG. 12.

Upon tactually sensing the completed penetration of stem end or tip 108 into the chest cavity, the operator will act on three ways shut off valve 1018, opening the passage between hose 1014 and stem 602 and closing passage between stem 602 and chamber 125.

At this point, the operator is ready to perform the cardiac compressiondecompression. As for devices 1002 and 1050, the operator, by pressing upon top wall 1022 of inflating-deflating device 1088, inflates balloon or expandable member 1088 as shown for device 1002 of FIG. 21. Inflation of balloon 1088 will result in its expansion and compression of the heart between the thoracic spine and the balloon 1080 itself, as shown for device 1002 of FIG. 21.

By releasing pressure upon top wall 1022 of inflating-deflating device 1008, the operator will deflate balloon 1088. Deflation of balloon 1088 will result in its contraction and, consequently, in the decompression of the heart.

By alternatively pressing upon inflating-deflating device 1008 and releasing such pressure, the operator will alternatively compress and decompress the heart.

Embodiment IV

Figure 25:
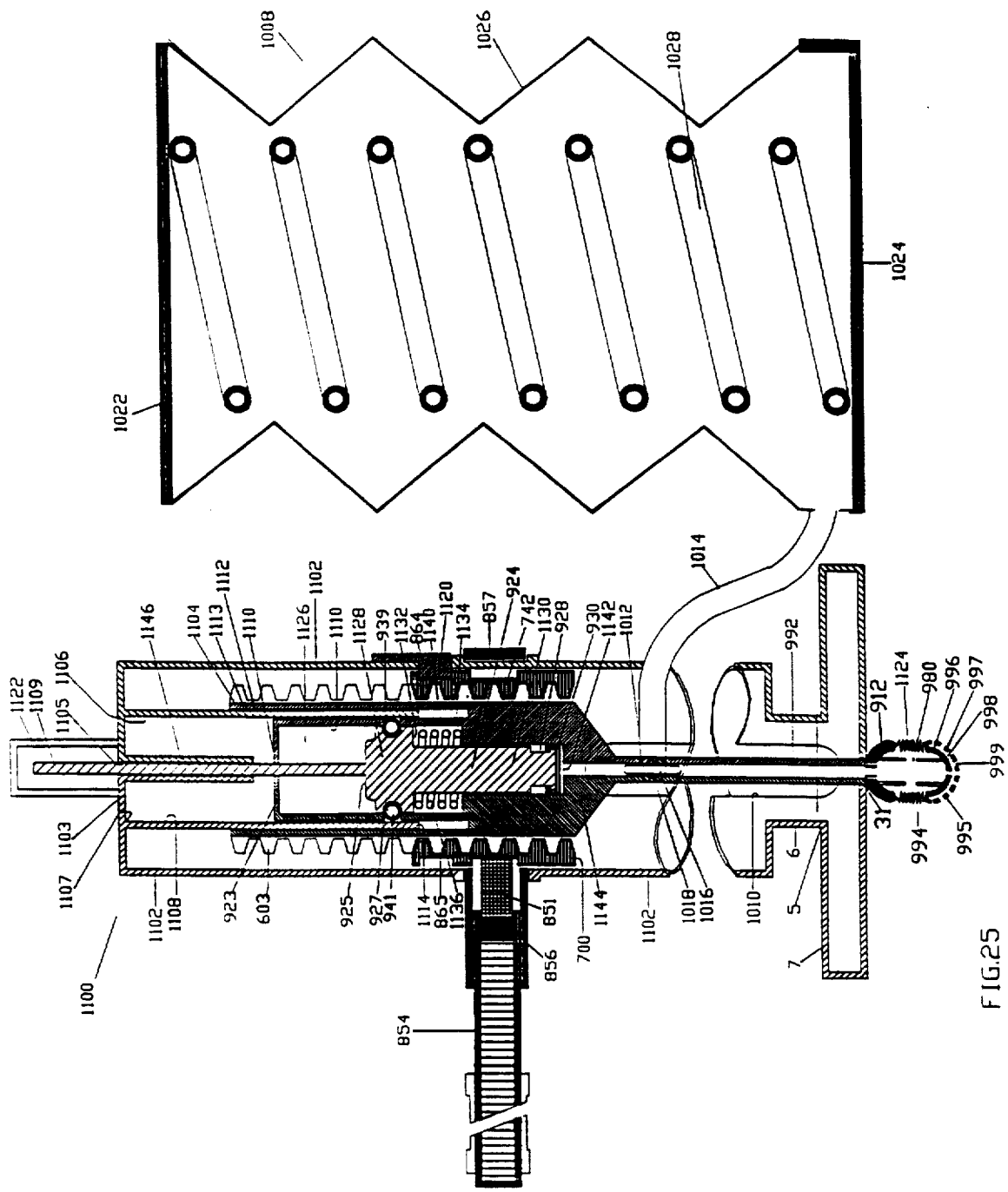
FIG. 25 is a vertical section of yet an alternative form of the device of FIG. 18 shown as it is prior to use.
Figure 26:
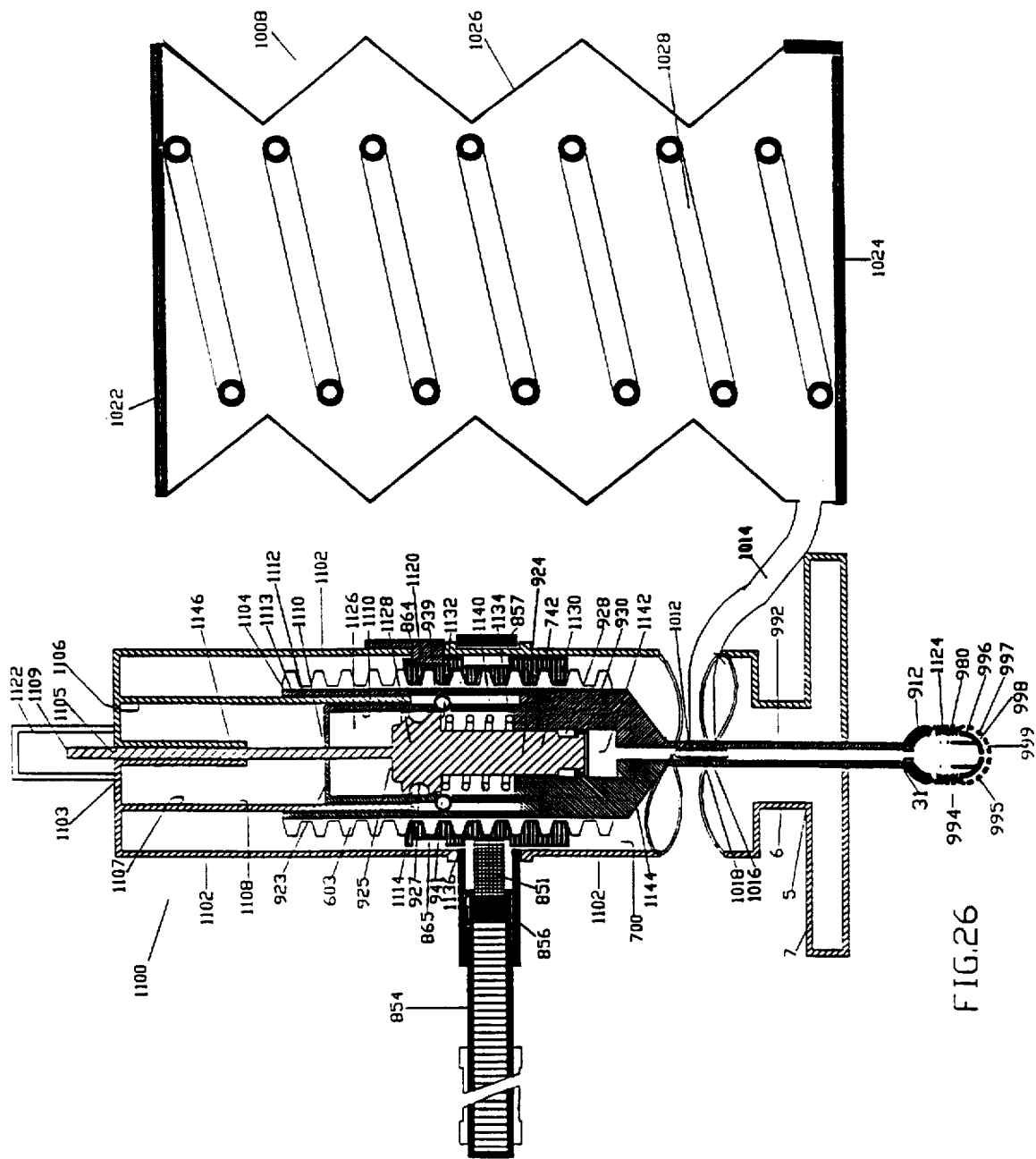
FIG. 26 is a vertical section of the device of FIG. 25 after arming.
Figure 27:
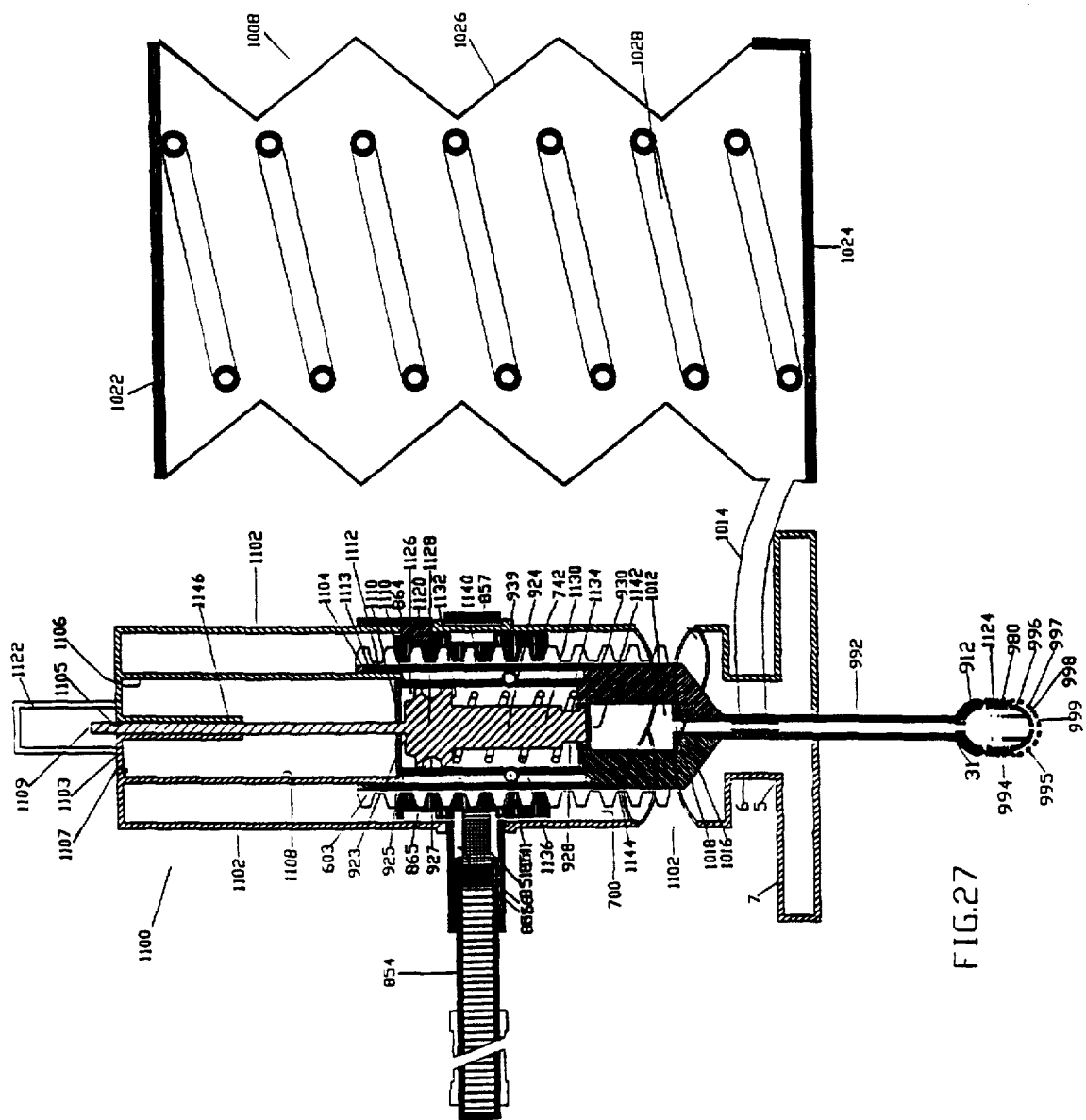
FIG. 27 is a vertical section of the device of FIG. 25 after penetration of blunt tip into chest cavity.

FIG. 25 shows an alternative form, generally indicated at 1100, of device 900 illustrated in FIGS. 15 to 17.

Device 1100 retains the same safety mechanisms of gaining entry into the chest cavity in front of the heart as device 900 of FIGS. 15 to 17, including the blunt penetrating tip, while it differs in the way of compressing and decompressing the arrested heart.

Device 1100, while maintaining some of the characteristics of device 900 of FIGS. 15 to 17, has some important structural differences. Corresponding parts have maintained the same numbering. Device 1100, as shown in FIG. 25, is composed of four main components: support member generally indicated at 1102, stem member or stem unit generally indicated at 1104, an intermediate member generally indicated at 700, and an inflating-deflating means or device generally indicated at 1008.

The support member 1102, of generally cylindrical hollow shape is the same as support member 800 of device 900 of FIGS. 15 to 17, except for the differences outlined below. As shown in FIG. 25, support member 1102 is closed is at its proximal end by top wall 1103. Opening 1105 is formed in top wall 1103. Sight chamber 1122 is mounted atop top wall 1103, surrounding opening 1105 of top wall 1103 of support member 1102 and upper segment of rod 1109 exiting through opening 1105.

A coaxially positioned hollow cylinder 1106 is circularly connected with its upper rim 1107 to the inner surface of top wall 1103 of support case 1102 while is open at its distal end 1104. Side wall 1108 of cylinder 1106 is interposed between an inner cylinder 1110, corresponding in some respects to cylinder or vacuum chamber 910 of device 900 of FIGS. 15 to 17, and an outer cylinder 1113 with cylindrical side wall 1112.

Distal end 1114 of hollow cylinder 1106 reaches a level distal to location of balls 941 described below.

Support member 1102 has, at its surface, on its distal segment 6, a slit 1010, in order to permit the insertion of distal end 1012 of hose 1014 of inflating-deflating device 1008 on window 1016 of outer stem 992 of stem unit 1104.

Pin 1120 substitutes pin 860 of device 900 of FIGS. 15 and 16. Pin 1120 is secured to support case 1102 through opening 864 to engage in annular recess 865 of intermediate member 700. Arm 866 of pin 860 described in FIGS. 15 and 16 for manual displacement is no longer present. Tubular guide 1146, projecting from the inner surface of top wall 1103, surrounds in a slideable fashion rod 1109 which stems out, as it will be described below, from upper face of piston 924. Intermediate member 700 is identical to intermediate member 700 of device of FIG. 12, thereof same numbers have been used for same parts. Lever 854 and annexed structures are identical to the same lever described for the device of FIGS. 15 and 16.

Stem member or unit member 1104 is structurally similar to stem member 901 of FIGS. 15 to 17, but devoid of some of its components, while some components are modified or added.

In particular gas-fluids container 129 with its handle 111, the entire chamber 917 with its side walls and all its content, diaphragm 918, the entire chamber 919 with its side walls and with all its content including pin 180 and shutter 190 and diaphragm 920 are no longer present.

Annular recesses 1121 and 1122 formed in the inside aspect of side wall of body 913 of stem unit 901 of device 900 of FIGS. 15 to 17 are no longer present.

Slideable sealing cylinder 914, spring 902, balls 918 and windows 920 formed in cylinder 910 are no longer present. Proximal support arm 912 of cylinder 910 are also removed. Stem member or stem unit 1104 is of general cylindrical shape, being its upper segment composed of two coaxially positioned cylinders, outer cylinder 1113 and inuer cylinder 1110, which grossly corresponds to vacuum chamber or cylinder 910 of FIGS. 15 and 16. Coaxially positioned inner cylinder 1110 and cylindrical side wall 1112 of outer cylinder 1113 are connected one to the other at their distal end by anterior segment 1144 of stem member 1104. Said inner cylinder 1110 and said cylindrical side wall 1112 of outer cylinder 1113 are separated in their proximal segment by space 1140. As mentioned above, inner cylinder 1110 and cylindrical side wall 1112 of outer cylinder 1113 of stem member 1104 are slidably mounted on side wall 1108 of hollow cylinder 1106 of support member 1102, which, by occupying space 1140, is interposed between the two. Distal end 1114 of hollow cylinder 1106 extends beyond the location of balls 941 when the device is its starting position. Anterior segment 1144 of stem member 1104 contains chamber 1142 which is posteriorly in continuity with chamber 1126 of cylinder 1110 and anteriorly communicates with the inside of stem 992. Within contiguous chambers 1126 and 1142 is slidably mounted piston 924, being 1130 its anterior segment and 1128 its posterior segment. Compression spring 1136 is mounted between face 1132 of posterior piston segment 1128 and flange 1134 of solid anterior segment 1144 of stem member 1104. Rod 1109 stems out of posterior face 925 of piston 924 projecting posteriorly. Rod 1109 exits through center opening of top wall 923 of chamber 1126 and continuing through tubular guide 1146 up to sight chamber 1122. Sealing cap 930 is mounted atop distal end of anterior piston segment 1130 to maintain air tightness. Balls 941 seat in recess 927 of piston 924 and are engaged in windows 939 of side wall of cylinder 1110 and are impeded to exit from recess 927 by side walls 1108 of cylinder 1106. Thread 603, mounted at the outer surface of stem member 1104 as for the device of FIG. 15 and 16, is matable to correspondent thread of intermediate member 700. Outer stem 992 is connected to distal end 1012 of hose 1014 of inflating-deflating means 1008 at window 1016. Three ways shut off valve 1018 is located at the connection between hose end 1012 of hose 1014 and outer stem 992.

Expandable member or balloon 1124, interposed and connected to hollow convex apex 995 and solid base 912 of stem end or tip 994 is of larger size when fully expanded than balloon 1000 of correspondent device 900 of FIGS. 15 to 17.

Inflating-deflating means or device 1008 with connected hose 1014 and shut off valve 1018 is the same device of FIGS. 18 to 21 and same numbering has been maintained.

Description of the Operation of Embodiment IV

Device 1100 is placed on the chest in the same way as device 900, the operator then ratchets lever 854, as described for cardiac pump 900 of FIGS. 15 to 17, causing advancement of the stem member 901 with respect to the support case 1102 into the thickness of the chest wall. Upon a preestablished advancement of the stem member by approximately 1 centimeter within the chest wall so that stem tip 994 is well buried inside the chest wall, to seal openings 999 from air entry, balls 941 which seat in annular recess 927 of piston 924 and are engaged in windows 939 of cylinder 1110 which is carried forward jointly to the stem unit 1104 to which is anchored by distal supports 920, will align with distal end 1114 of hollow cylinder 1106 which, as described above, protrudes from the top wall 1103 of support case 1102 and is connected to it.

With downward displacement of stem unit 1104 and consequently of inner cylinder 1110, which is part of it, in respect to side wall 1108 of cylinder 1106, balls 941, carried within window 939 of walls of inner cylinder 1110, will gradually advance to align first with level of distal end or edge 1114 of side wall 1108 of cylinder 1106, then, by moving further downward, said balls will pass the level of the distal edge 1114. As soon as balls 941 pass the level of edge 1114 of side wall 1108 of cylinder 1106, they will no longer be retained, within annular recess 927 of piston 924 and window 939 of inner cylinder 1110, by distal end 1114 of hollow cylinder 1006. Exit of balls 941 from their seating in annular recess 927 of piston 924 though window 939 of inner cylinder 1110 into space 1120 will be accelerated by compressed compression spring 1136, which, by urging piston 924 upwardly, will force dislodgment of said balls 941 out of their seat in annular recess 927 of piston 924, being said balls 941, as described above, no longer forced to be retained in their seat by side wall 1108 of cylinder 1106.

Upon dislodgment of locking balls 941 from annular recess 927 of piston 924, piston will no longer be retained in its starting advanced position, and compressed compression spring 1136, which urges piston 924 upwardly, will be able to upwardly displace piston 924. However, being the interior of cylinder 1110, and, more specifically, being anterior chamber 1142 in open flow communication with openings 999 of stem tip 994 via stem 992, and being said openings sealed by tissues burying being stem tip 994 within the thickness of the chest wall, piston 924, which airtightly slides within cylinder 1110, will create a vacuum in chamber 1142 when upwardly displaced. Said vacuum will oppose to full withdrawal of piston 924 urged by spring 1136, resulting in a partial upward displacement of piston 924. From this moment on, piston 924 will be unimpeded to move further upward upon vanishing of the vacuum present in chamber 1142 in front of piston 924. Vanishing of vacuum in chamber 1142 in front of piston 924 will occur upon gaining access to the chest cavity by stem tip 994. Upon gaining access to the chest cavity, openings 999 of stem tip 994 will lose the sealing put up by the tissue layers of the chest wall, and, being said openings 999 of stem tip 994 in flow communication with chamber 1142, will place said chamber 1142 in flow communication with the chest cavity, with resulting vanishing of the vacuum in chamber 1142.

The sequence resulting in readiness by piston 924 to move upward upon vanishing of the vacuum in front of it is an arming operation, which is made possible in an automatic fashion, by the presence of hollow cylinder 11106.

Access into the chest cavity by stem tip 994 will be signaled to the operator by the full upward displacement of piston 924. Upon occurred penetration into chest cavity of stem tip 994 and consequent vanishing of vacuum in chamber 1142, piston 924, as described above, will be allowed to fully displace upward. Full upward displacement of piston 924 will be revealed to the operator for instance by upward displacement of rod 1109 which, being fixed to posterior end 925 of piston 924 and by exiting inner or vacuum cylinder 1110 through the center opening formed in top wall 923 of cylinder 1110, then exiting through opening 1105 of top wall 1103 of intermediate member 1102, will move upward, jointly with said piston.

As soon as the operator of the device will be made aware of the occurred penetration into the chest cavity by the upward displacement of rod 1109 and piston 924, the operator will act on three ways shut off valve 1108, opening the passage between hose 1104 and outer stem 992 and closing passage between stem 992 and chamber 907.

At this point, the operator is ready to perform the cardiac compressiondecompression. The operator, by pressing upon top wall 1022 of inflating-deflating device 1008, inflates balloon 1124, as for the device 1002 shown in FIG. 21.

Inflation of balloon 1124 will result in its expansion and compression of the heart between the thoracic spine and the balloon 1124 itself, as previously shown in FIG. 21. By releasing pressure upon top wall 1022 of inflating-deflating device 1008, the operator will deflate balloon 1124.

Embodiment V

FIG. 35 shows a cross-sectional view of a detail of an alternative form of device 1070 of FIG. 24. The device, generally indicated at 1500, is basically the same as device 1070 of FIG. 24, except for few important differences, such as stem end 1502. Stem tip 1502 is composed of two parts: proximal part 1504 shaped as an inverted cup firmly attached to distal end 1506 of stem 602 of stem member 1074, and distal part or convex apex 1506. Convex apex 1506 is firmly attached to inner hollow stem 1508 which is slideable in airtight fashion within hollow stem 602 and has proximal opening 1522. Convex apex has circular edge 1510 adapted to fit together with circular edge 1512 of circular opening 1514 of proximal cart 1504 of stem tip 1502 to form together a spheroidly-shaped stem tip 1502. Inner hollow stem 1508 has at least one distal opening 1516 within stem end 1502 in flow communication with expandable member or balloon 1520 partially or fully contained in a contracted status within stem end 1502. Hollow inner stem 1502 also provides lateral stability to expandable member 1520 upon expansion of balloon 1520 in operation and also provides the device with means of direction totally lacking in the cited Prisk reference, and allow the operator to have full control on the direction to be given to the expandable member in respect to the position of the heart.

The device is operated as device 1070 of FIG. 24. After a small superficial incision is made, which could be as small as one centimeter in length, to allow that the blunt end of the device wins the skin resistance, in a location preferably in the left parastemal region in a skin area corresponding to the intrathoracic anatomical area designated "sine pleura," the blunt tip of the device is engaged in the skin incision and advanced by blunt dissection through the thickness of the chest wall as for device 1070 of FIG. 24. The choice of the area sine pleura prevents the insurgence of pneumothorax, i.e., collapsing of the lung, which inevitably occurs every time the pleural cavity is inadvertedly entered. With regard to the occurrence of pneumothorax, due to the fact that the area "sine pleura" is a substantially restricted area, the choice of such area is only meaningful if the opening passage through the chest wall is significantly small, such as it can be achieved with all the embodiments described in this invention. Being the width of this area in the order of less than two centimeter, it is critical that the heart contacting pumping member which has to be passed through the chest wall to enter the chest cavity is contracted to a comparably small size, i.e., less than 2 centimeter or 1.5 centimeter.

Blunt stem end 1502 is further advanced through the thickness of chest wall 107 by blunt dissection until it enters the chest cavity by blunt dissection.

Upon entry into the chest cavity the operator will be alert of the occurred entry of stem end 1502 as for device 1070 of FIG. 24. Balloon 1520 will be inflated by the operator acting upon pneumatic source or inflating-deflating device 1070 of FIG. 24, not shown in FIG. 35, as described for device 1070 of FIG. 24. Air or suitable gas such as $CO_2$ will flow into hollow inner stem through opecing 1522 and will exit through distal opening 1516 to enter balloon 1520 resulting in its inflation. As balloon 1520 begins to inflate, as seen in FIG. 36, hollow inner stem 1508, being slideable within hollow stem 1508, will be dragged forward with convex apex 1506 to which is firmly attached, being convex apex 1516 of stem end or tip 1502 being finrly attached to the heart contacting surface. Although the depth of advancement of hollow inner stem 1508 can be variable depending upon the individual anatomical variabilities, and the balloon may not be required to be fully inflated before it achieves the goal of compressing the heart, the presence of the guiding or inner hollow stem 1508 will guarantce that the balloon inflates only toward the direction given by the operator. This offer the advantage of using one size balloon for all individual to achieve identical results in terms or compression results. Due to the capability offered by this device to aim the balloon precisely toward the heart and overcoming therefore even the slightest individual anatomical differences regarding position, the compression results can be optimized by monitoring blood pressure and pulse of the patient having cardiac compression decompression.

The compression pressure exerted upon the heart can be quantified to absolute precision with proper instruments so that no incidents due to excess of compression pressure can occur. As above described it should also be emphasized that guiding stem 1508 only moves passively dragged by the inflating heart contacting member, therefore it never constitutes a threat for injuring the heart in the event the balloon accidentally deflates.

The above disclosed slideable guiding stem can be applied to all embodiments where the heart contacting member is an inflatable deflatable type.

The guiding stem can also be used for stabilization of the expandable member of all types of embodiments of type A and to retract the center or umbilical area of the expandable member of such embodiments.

FIG. 37 shows balloon or expandable member or inflatable-deflatable member 1520 inflated to the required pressure to achieve cardiac compression.

Balloon 1520 can be made of polyethylene or suitable material used for angioplasty. It is preferable that the balloon be made of non compliant or substantially non compliant material, however it can also be made of stretchable material if stretchable material can achieve the same results. The preferred general shape of balloon 1520 is grossly cylindrical. The diameter of the cylinder should be adequate to offer a sufficient area of contact with the heart to result with heart compression. The surface contacting the heart is deformable to adapt to the anatomy of the anterior aspect of the heart to perfectly mate with the anterior aspect of the heart. Due to the guidance of guiding stem 1508, there is no need to give any particular shape to the heart contacting surface of the heart compressing member to prevent that the healt compressing member accidentally misses the heart, because the guiding stem assures that the heart compressing member is properly positioned on the heart.

What is claimed is:

1. A method of direct cardiac massage, said method comprisirng:

advancing a cardiac massage device in a posterior direction through a thoracostomy in a patient's chest wall to engage a heart surface; and compressing the heart surface using the cardiac massage device.

2. A method as in claim 1, further comprising expanding an expandable member on the cardiac massage device after the expandable member has advanced through the chest wall.

3. A method as in claim 2, wherein the expandable member is moved to alternately compress the heart against the thoracic spine and release such compression to effect pumping of the heart.

4. A method for direct cardiac massage, said method comprising:

advancing a cardiac massage device through an intercostal space to engage a heart surface; and compressing the heart surface using the cardiac massage device.

5. A method as in claim 4, further comprising expanding an expandable member on the cardiac massage device after the expandable member has advanced through the chest wall.

6. A method as in claim 6, wherein the expandable member is moved to alternately compress the heart against the thoracic spine and release such compression to effect pumping of the heart.

7. A method for direct cardiac massage, said method comprising:

advancing a cardiac massage device through the trigonum sine pleura of a patient's chest wall to engage a heart surface; and compressing the heart using the cardiac massage device.

8. A method as in claim 7, further comprising expanding an expandable member on the cardiac massage device after the expandable member has advanced through the chest wall.

9. A method as in claim 8, wherein the expandable member is moved to alternately compress the heart against the thoracic spine and release such compression to effect pumping of the heart.

* * * * *